(12) United States Patent
Yoshioka et al.

(10) Patent No.: US 8,574,882 B2
(45) Date of Patent: Nov. 5, 2013

(54) THERMOSTABLE 1,5-ANHYDROGLUCITOL DEHYDROGENASE, AND METHOD FOR MEASUREMENT OF 1,5-ANHYDROGLUCITOL BY USING THE SAME

(75) Inventors: Hideki Yoshioka, Takasaki (JP); Shuhei Tsukamoto, Takasaki (JP); Minoru Masuda, Takasaki (JP); Reiko Machida, Takasaki (JP); Yoshihiko Umegae, Takasaki (JP); Masahiko Yabuuchi, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 156 days.

(21) Appl. No.: 12/999,992

(22) PCT Filed: Jun. 18, 2009

(86) PCT No.: PCT/JP2009/061074
§ 371 (c)(1),
(2), (4) Date: Mar. 21, 2011

(87) PCT Pub. No.: WO2009/154247
PCT Pub. Date: Dec. 23, 2009

(65) Prior Publication Data
US 2012/0094320 A1 Apr. 19, 2012

(30) Foreign Application Priority Data

Jun. 19, 2008 (JP) .................................. 2008-159927

(51) Int. Cl.
| | | |
|---|---|---|
| C12N 9/02 | (2006.01) | |
| C12N 15/00 | (2006.01) | |
| C12N 1/20 | (2006.01) | |
| C12Q 1/32 | (2006.01) | |
| C12Q 1/00 | (2006.01) | |
| C12P 21/06 | (2006.01) | |
| C12P 19/34 | (2006.01) | |
| C07H 21/04 | (2006.01) | |
| C07K 1/00 | (2006.01) | |

(52) U.S. Cl.
USPC ........... 435/189; 435/26; 435/69.1; 435/91.1; 435/320.1; 435/252.33; 536/23.2; 536/23.1; 530/350; 205/777.5

(58) Field of Classification Search
USPC ......... 435/189, 26, 69.1, 91.1, 320.1, 252.33; 536/23.2, 23.1; 530/350; 205/777.5
See application file for complete search history.

(56) References Cited

U.S. PATENT DOCUMENTS 4,810,640 A 3/1989 Nakamura et al.

FOREIGN PATENT DOCUMENTS

| | | |
|---|---|---|
| EP | 0392404 A2 | 10/1990 |
| EP | 0846773 A1 | 6/1998 |
| JP | A-62-079780 | 4/1987 |
| JP | A-02-268679 | 11/1990 |
| JP | A-03-047094 | 2/1991 |
| JP | B2-03-024200 | 4/1991 |
| JP | B2-05-041238 | 6/1993 |
| JP | A-07-067697 | 3/1995 |
| JP | 2872983 | 1/1999 |
| JP | A-11-018762 | 1/1999 |
| JP | B2-03-024200 | 1/1999 |
| JP | A-2000-135079 | 5/2000 |
| JP | A-2000-316570 | 11/2000 |
| JP | A-2002-186497 | 7/2002 |
| JP | 3819094 | 6/2006 |
| WO | WO-A-2008/072702 | 6/2008 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*

(Continued)

Primary Examiner — Ganapathirama Raghu
(74) Attorney, Agent, or Firm — Leason Ellis LLP.

(57) ABSTRACT

A protein comprising an amino acid sequence having at least one mutation selected from a Gly-4 to Ala mutation, a Glu-6 to His mutation, a Ser-14 to Thr mutation, an Ala-37 to Thr or Arg mutation, a Pro-50 to Gln mutation, a Glu-67 to Gly mutation, an Asp-80 to Tyr mutation, a Val-93 to Met mutation, an Arg-156 to Pro mutation, a Leu-164 to Met mutation, an Asn-202 to Asp mutation, a Thr-235 to Ala mutation, an Asn-348 to Tyr mutation, a Gly-362 to Arg mutation and a Val-473 to Ala mutation in the amino acid sequence depicted in SEQ II NO:4. (2) A thermostable protein which comprises an amino acid sequence derived from the amino acid sequence having at least one variation described in (1) and having 1,5-anhydroglucitol dehydrogenase activity. These proteins act specifically on 1,5-anhydroglucitol (1,5-AG), have thermal stability and exhibit excellent storage stability.

11 Claims, 9 Drawing Sheets

(56) References Cited

OTHER PUBLICATIONS

Yoshida et al., A Novel NAD-Dependent Dehydrogenase, Highly Specific for 1,5-Anhydro-D-Glucitol, from *Trichoderma longibrachiatum* Strain 11-3, Applied and Environmental Microbiology, May 2003, pp. 2603-2607, vol. 69, No. 5.
International Search Report for the corresponding PCT application No. PCT/JP2009/061074.
European Search Report mailed May 22, 2013 for the corresponding European Application No. 09766695.2.
Homology Search attached with the European Search Report mailed May 22, 2013 for the corresponding European Application No. 09766695.2.

\* cited by examiner

THERMOSTABLE 1,5-ANHYDROGLUCITOL DEHYDROGENASE, AND METHOD FOR MEASUREMENT OF 1,5-ANHYDROGLUCITOL BY USING THE SAME

CROSS-REFERENCE TO RELATED PATENT APPLICATIONS

This application is a U.S. National Phase Application under 35 U.S.C. §371 of International Patent Application No. PCT/JP2009/061074, filed Jun. 18, 2009, and claims the benefit of Japanese Patent Application No. 2008-159927, filed Jun. 19, 2008, all of which are incorporated by reference herein. The International Application was published in Japanese on Dec. 23, 2009 as International Publication No, WO 2009/154247 under PCT Article 21(2).

FIELD OF THE INVENTION

The present invention relates to a thermostable 1,5-anhydroglucitol dehydrogenase useful in an enzymatic assay method for 1,5-anhydroglucitol, a gene encoding the thermostable 1,5-anhydroglucitol dehydrogenase, a recombinant vector, a transformant, a method for producing the thermostable 1,5-anhydroglucitol dehydrogenase, an enzymatic assay method for 1,5-anhydroglucitol using the thermostable 1,5-anhydroglucitol dehydrogenase, and a kit used in the assay method.

BACKGROUND OF THE INVENTION 1,5-anhydroglucitol (hereinafter, referred to as 1,5-AG) is present in human body fluids such as serum, plasma and urine and largely varies in amount in body fluids due to a certain kind of disease, particularly, diabetes mellitus. Therefore, assay values of 1,5-AG in body fluids serve as a useful diagnostic index and have been an important test item in clinical test in recent years.

As a method for quantifying this 1,5-AG, a method described in, for example, PATENT DOCUMENT 1 is in the mainstream which comprises allowing pyranose oxidase to act on 1,5-AG and subjecting the formed hydrogen peroxide to colorimetry in a peroxidase chromogenic system. This method has been practiced using a general-purpose automatic analyzer.

For example, a method described in PATENT DOCUMENT 2 is known as an alternative assay method, which comprises allowing a 1,5-AG-phosphorylating enzyme to act on 1,5-AG in the presence of a phosphate group donor and subjecting the obtained 1,5-AG-6-phosphate to colorimetry using 1,5-AG-6-phosphate dehydrogenase.

Moreover, a method for assaying 1,5-AG using 1,5-AG dehydrogenase has also been reported in PATENT DOCUMENTS 3 to 5. *Agrobacterium tumefaciens*-derived dehydrogenase described in PATENT DOCUMENTS 4 and 5, *Cytophaga bacterium*-derived dehydrogenase described in PATENT DOCUMENT 6, *Rahnella aquatilis*-, *Enterobacter cloacae*- or *Serratia marcescens*-derived dehydrogenase described in PATENT DOCUMENT 7, dehydrogenase derived from fungi such as *Eupenicillium crustaceum, Hansenula california, Pichia carsonii* and *Pichia pseudopolymorpha* described in PATENT DOCUMENT 8, *Trichoderma longibrachiatum*-derived dehydrogenase described in PATENT DOCUMENT 9, and the like have been reported as dehydrogenases acting on 1,5-AG.

CITATION LIST

Patent Documents
PATENT DOCUMENT 1: JP 5-41238 B
PATENT DOCUMENT 2: JP 2002-186497 A
PATENT DOCUMENT 3: JP 3-24200 B
PATENT DOCUMENT 4: Japanese Patent No. 2872983
PATENT DOCUMENT 5: Japanese Patent No. 3819094
PATENT DOCUMENT 6: JP 7-67697 A
PATENT DOCUMENT 7: JP 11-18762 A
PATENT DOCUMENT 8: JP 2-268679 A
PATENT DOCUMENT 9: JP 2000-135079 A

DISCLOSURE OF THE INVENTION

Problems to be Solved by the Invention

In a conventional assay method using pyranose oxidase, this enzyme strongly acts not only on 1,5-AG but on glucose. Therefore, a complicated assay system containing a glucose-digesting enzyme or the like is required for digesting coexisting glucose in advance and completely.

Moreover, a method involving colorimetry using 1,5-AG-6-phosphate dehydrogenase also inevitably requires allowing a glucose-digesting enzyme, a 1,5-AG-phosphorylating enzyme, and so on to coexist in an assay system and is therefore complicated.

On the other hand, an assay method using 1,5-AG dehydrogenase is a convenient method, because this enzyme minimizes a load of glucose digestion because of its high specificity for 1,5-AG and acts on 1,5-AG in the absence of an electron carrier to directly reduce a reductive chromogenic agent. However, the stability of the 1,5-AG dehydrogenase itself is less than sufficient, and practical 1,5-AG assay reagents or 1,5-AG assay sensors for automatic analyzers have not been developed. Thus, improvement in the stability of the enzyme has been a challenge to practical use.

An object of the present invention is to provide a novel 1,5-AG dehydrogenase that specifically acts on 1,5-AG and is excellent in stability and a method for producing the same, and to provide an assay method applicable to the assay of 1,5-AG in clinical samples.

Means for Solving the Problems

Conventional 1,5-AG dehydrogenases were difficult to practically apply, because they require NAD(P) as a coenzyme and are insufficiently stable to heat. On the other hand, in contrast to this, *Pseudomonas*-derived 1,5-AG dehydrogenase described in PATENT DOCUMENT 3 is independent of a coenzyme. Therefore, the present inventors have believed that this enzyme is applicable to clinical assay methods for 1,5-AG by imparting thermostability thereto by modification to enhance storage stability, and have thus conducted studies mainly on the enzyme. Specifically, the present inventors have diligent studies to attain the object. As a result of: obtaining a 1,5-AG dehydrogenase-encoding gene from a 1,5-AG dehydrogenase-producing bacterium *Pseudomonas* sp. NK-85001 (International Patent Organism Depositary, National Institute of Advanced Industrial Science and Technology Accession No. FERM BP-01037) described in PATENT DOCUMENT 3; subjecting the gene to random mutagenesis or the like to prepare a variant gene library; obtaining a thermostable 1,5-AG dehydrogenase-producing variant strain from the library; and further modifying the 1,5-AG dehydrogenase for enhancing the storage stability of the enzyme by imparting thermostability variation thereto, the present inventors have found that the storage stability is significantly improved by introducing amino acid substitution in the amino acid sequence of the original enzyme. Based on these findings, the present invention has been completed.

SUMMARY OF THE INVENTION

Specifically, the present invention relates to the following [1] to [12]:

[1] A protein shown in the following (1) or (2):

(1) a protein comprising an amino acid sequence represented by SEQ ID NO: 4 having at least one variation selected from variations of an amino acid residue at position 4 changed from a glycine residue to an alanine residue, an amino acid residue at position 6 changed from a glutamine residue to a histidine residue, an amino acid residue at position 14 changed from a serine residue to a threonine residue, an amino acid residue at position 37 changed from an alanine residue to a threonine residue or an arginine residue, an amino acid residue at position 50 changed from a proline residue to a glutamine residue, an amino acid residue at position 67 changed from a glutamic acid residue to a glycine residue, an amino acid residue at position 80 changed from an asparagine residue to a tyrosine residue, an amino acid residue at position 93 changed from a valine residue to a methionine residue, an amino acid residue at position 156 changed from an arginine residue to a proline residue, an amino acid residue at position 164 changed from a leucine residue to a methionine residue, an amino acid residue at position 202 changed from an asparagine residue to an aspartic acid residue, an amino acid residue at position 235 changed from a threonine residue to an alanine residue, an amino acid residue at position 348 changed from an asparagine residue to a tyrosine residue, an amino acid residue at position 362 changed from a glycine residue to an arginine residue, and an amino acid residue at position 473 changed from a valine residue to an alanine residue; and (2) a thermostable protein which comprises an amino acid sequence derived from the amino acid sequence having at least one variation described in (1) by addition, deletion or substitution of one or more amino acid residues other than the varied amino acid residue and has 1,5-anhydroglucitol dehydrogenase activity.

[2] The protein according to [1], wherein the protein maintains 8% or more of its 1,5-anhydroglucitol dehydrogenase activity after heating at 45° C. for 10 minutes.

[3] The protein according to [1] or [2], wherein the protein is selected from the following proteins:

1) a protein comprising an amino acid sequence represented by SEQ ID NO: 1 which has all the variations described in (1) of [1] except for the variation at position 6, wherein the variation of the amino acid residue at position 37 is to an arginine residue;

2) a protein comprising an amino acid sequence represented by SEQ ID NO: 1 having an arginine residue in place of a proline residue at position 156;

3) a protein comprising an amino acid sequence represented by SEQ ID NO: 1 having an arginine residue in place of a proline residue at position 156 and a valine residue in place of an alanine residue at position 473;

4) a protein comprising an amino acid sequence represented by SEQ ID NO: 1 having a glutamic acid residue in place of a glycine residue at position 67, an arginine residue in place of a proline residue at position 156, and a valine residue in place of an alanine residue at position 473;

5) a protein comprising an amino acid sequence represented by SEQ ID NO: 1 having a glutamic acid residue in place of a glycine residue at position 67, an asparagine residue in place of a tyrosine residue at position 80, an arginine residue in place of a proline residue at position 156, and a valine residue in place of an alanine residue at position 473;

6) a protein comprising an amino acid sequence represented by SEQ ID NO: 1 having a glutamic acid residue in place of a glycine residue at position 67, an asparagine residue in place of a tyrosine residue at position 80, an asparagine residue in place of an aspartic acid residue at position 202, and a valine residue in place of an alanine residue at position 473;

7) a protein comprising an amino acid sequence represented by SEQ ID NO: 1 having a glutamic acid residue in place of a glycine residue at position 67, an asparagine residue in place of a tyrosine residue at position 80, an arginine residue in place of a proline residue at position 156, and an asparagine residue in place of an aspartic acid residue at position 202;

8) a protein comprising an amino acid sequence represented by SEQ ID NO: 1 having a glutamic acid residue in place of a glycine residue at position 67, an arginine residue in place of a proline residue at position 156, an asparagine residue in place of an aspartic acid residue at position 202, and a valine residue in place of an alanine residue at position 473;

9) an amino acid sequence represented by SEQ ID NO: 1 having a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473;

10) a protein comprising an amino acid sequence represented by SEQ ID NO: 1 having a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473;

11) a protein comprising an amino acid sequence represented by SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473;

12) a protein comprising an amino acid sequence represented by SEQ ID NO: 1 having a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

13) a protein comprising an amino acid sequence represented by SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, an asparagine residue in place of a tyrosine residue at position 348, and a valine residue in place of an alanine residue at position 473;

14) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, and a valine residue in place of an alanine residue at position 473;

15) a protein comprising an amino acid sequence represented by SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

16) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

17) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

18) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473;

19) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, and a valine residue in place of an alanine residue at position 473;

20) a protein comprising an amino acid sequence represented by SEQ ID NO: 1 having a glycine residue in place of an alanine residue at position 4, a histidine residue in place of a glutamine residue at position 6, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473; and 21) a protein comprising an amino acid sequence represented by SEQ ID NO: 1 having a glycine residue in place of an alanine residue at position 4, a serine residue in place of a threonine residue at position 14, an alanine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473.

[4] A gene comprising a DNA shown in the following (1) or (2):

(1) a DNA encoding a protein according to any of [1] to [3]; and (2) a DNA which hybridizes under stringent conditions to a DNA comprising a nucleotide sequence complementary to the DNA encoding a protein according to any of [1] to [3] and encodes a thermostable protein having 1,5-anhydroglucitol dehydrogenase activity.

[5] A recombinant vector containing a gene according to [4].

[6] A transformant comprising a recombinant vector according to [5].

[7] The transformant according to [6], wherein a host for the transformant is *E. coli*.

[8] A method for producing a thermostable 1,5-anhydroglucitol dehydrogenase, comprising culturing a transformant according to [6] or [7] and collecting a protein according to any of [1] to [3] from the cultures.

[9] A method for assaying 1,5-anhydroglucitol using a thermostable protein having 1,5-anhydroglucitol dehydrogenase activity according to any of [1] to [3].

[10] The method for assaying 1,5-anhydroglucitol according to [9], wherein the assay of 1,5-anhydroglucitol is performed in the presence of albumin.

[11] The method for assaying 1,5-anhydroglucitol according to [9], wherein the assay method is an electrochemical measurement method using a phenothiazine compound as a redox mediator and silver-silver chloride electrodes as a reference electrode and/or a counter electrode. [12] A kit for assaying 1,5-anhydroglucitol, comprising a protein according to any of [1] to [3].

Advantages of the Invention

A thermostable 1,5-AG dehydrogenase of the present invention is an enzyme that specifically acts on 1,5-AG, exhibits excellent storage stability because of having thermostability, and is exceedingly useful in 1,5-AG quantification reagents or convenient and practical 1,5-AG assay using an enzyme sensor introduced commercially. Moreover, a method for assaying 1,5-AG using the thermostable 1,5-AG dehydrogenase is a highly sensitive and stable method and can be put in practical use. Furthermore, a kit for assaying 1,5-AG containing the thermostable 1,5-AG dehydrogenase has enhanced storage stability and can be used in clinical practice.

BRIEF DESCRIPTION OF THE DRAWINGS

FIG. 3-1 is a diagram showing the distribution of variations in each of the thermostable 1,5-AG dehydrogenases Ver. 1.0 to Ver. 5.1;

FIG. 3-2 is a diagram showing the distribution of variations in each of the thermostable 1,5-AG dehydrogenases Ver. 6.0 to Ver. 9.0;

FIG. 3-3 is a diagram showing the distribution of variations in each of the thermostable 1,5-AG dehydrogenases Ver. 10.0 to Ver. 12.0;

DESCRIPTION OF EMBODIMENTS

Figure 1:
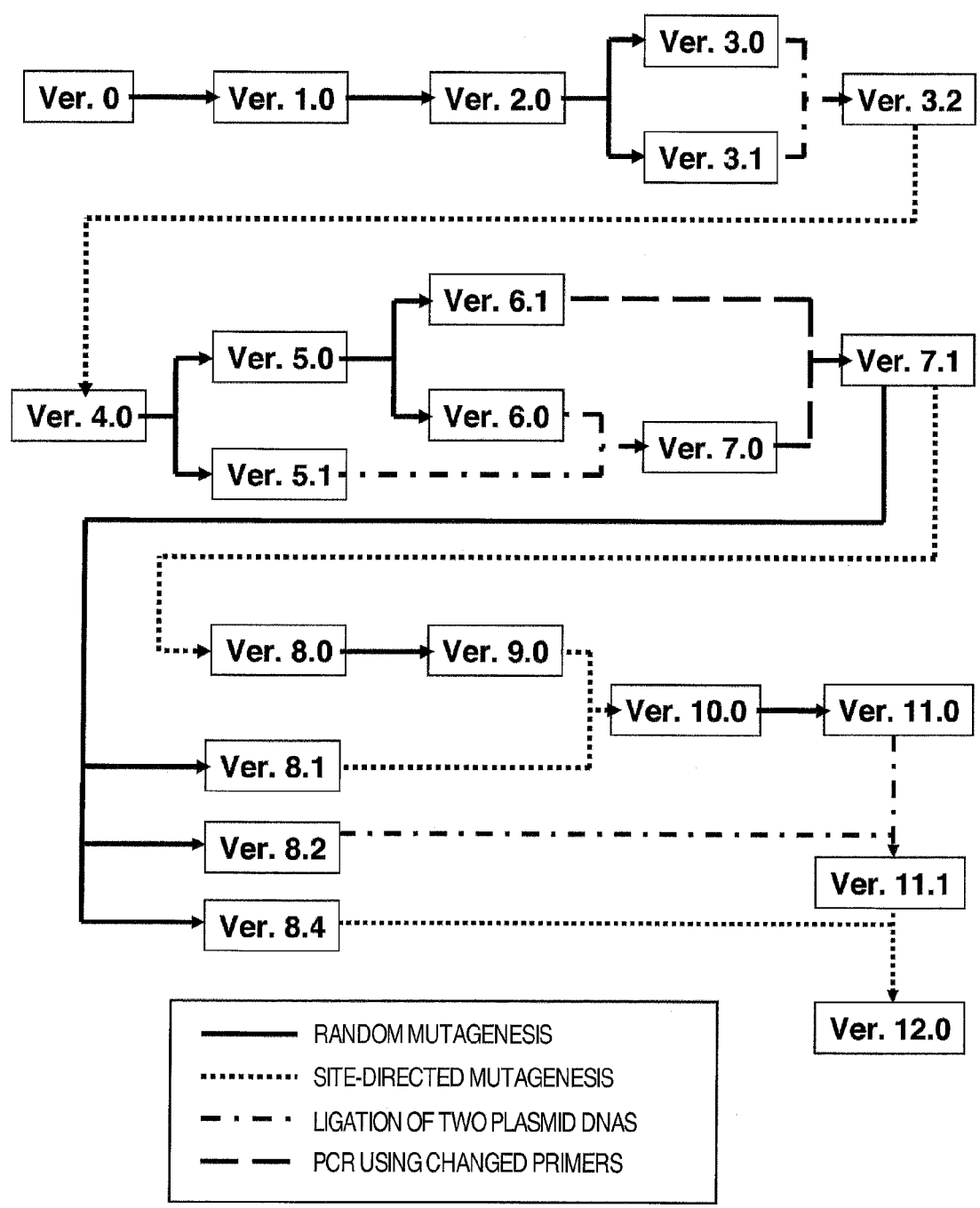
FIG. 1 is a flow chart representing a system diagram for preparing 1,5-AG dehydrogenases Ver. 0 to Ver. 12.0.

A thermostable 1,5-AG dehydrogenase of the present invention is a protein shown in the following (1) or (2):

(1) a protein comprising an amino acid sequence represented by SEQ ID NO: 4 having at least one variation selected from variations of an amino acid residue at position 4 changed from a glycine residue to an alanine residue, an amino acid residue at position 6 changed from a glutamine residue to a histidine residue, an amino acid residue at position 14 changed from a serine residue to a threonine residue, an amino acid residue at position 37 changed from an alanine residue to a threonine residue or an arginine residue, an amino acid residue at position 50 changed from a proline residue to a glutamine residue, an amino acid residue at position 67 changed from a glutamic acid residue to a glycine residue, an amino acid residue at position 80 changed from an asparagine residue to a tyrosine residue, an amino acid residue at position 93 changed from a valine residue to a methionine residue, an amino acid residue at position 156 changed from an arginine residue to a proline residue, an amino acid residue at position 164 changed from a leucine residue to a methionine residue, an amino acid residue at position 202 changed from an asparagine residue to an aspartic acid residue, an amino acid residue at position 235 changed from a threonine residue to an alanine residue, an amino acid residue at position 348 changed from an asparagine residue to a tyrosine residue, an amino acid residue at position 362 changed from a glycine residue to an arginine residue, and an amino acid residue at position 473 changed from a valine residue to an alanine residue; and (2) a thermostable protein which comprises an amino acid sequence derived from the amino acid sequence having at least one variation described in (1) by addition, deletion or substitution of one or more amino acid residues other than the varied amino acid residue and has 1,5-anhydroglucitol dehydrogenase activity.

In this context, the amino acid sequence represented by SEQ ID NO: 4 corresponds to the amino acid sequence of 1,5-AG dehydrogenase obtained from a 1,5-AG dehydrogenase-producing bacterium *Pseudomonas* sp, NK-85001 (International Patent Organism Depositary, National Institute of Advanced Industrial Science and Technology Accession No, FERM BP-01037) described in PATENT DOCUMENT 1 Furthermore, the thermostable 1,5-AG dehydrogenase of the present invention corresponds to, as described above in (1), a protein comprising an amino acid sequence represented by SEQ ID NO: 4 having at least one variation selected from a variation from a glycine residue at position 4 to an alanine residue, a variation of an amino acid residue at position 6 from a glutamine residue to a histidine residue, a variation from a serine residue at position 14 to a threonine residue, a variation from an alanine residue at position 37 to a threonine residue or an arginine residue, a variation from a proline residue at position 50 to a glutamine residue, a variation from a glutamic acid residue at position 67 to a glycine residue, a variation from an asparagine residue at position 80 to a tyrosine residue, a variation from a valine residue at position 93 to a methionine residue, a variation from an arginine residue at position 156 to a proline residue, a variation from a leucine residue at position 164 to a methionine residue, a variation from an asparagine residue at position 202 to an aspartic acid residue, a variation from a threonine residue at position 235 to an alanine residue, a variation from an asparagine residue at position 348 to a tyrosine residue, a variation from a glycine residue at position 362 to an arginine residue, and a variation from a valine residue at position 473 to an alanine residue.

Furthermore, the thermostable 1,5-AG dehydrogenase of the present invention corresponds to, as described above in (2), a thermostable protein which comprises an amino acid sequence derived from the amino acid sequence having at least one variation described in (1) by addition, deletion or substitution of one or more amino acid residues other than the varied amino acid residue and has 1,5-anhydroglucitol dehydrogenase activity. Examples of such a protein include thermostable proteins which comprise an amino acid sequence derived therefrom by addition, deletion or substitution of preferably approximately 1 to 20, particularly preferably approximately 2 to 10 amino acids and have a 1,5-AG dehydrogenase activity.

In the present invention, the thermostable 1,5-AG dehydrogenase or the thermostable protein having a 1,5-AG dehydrogenase activity refers to those maintaining 8% or more of its 1,5-AG dehydrogenase activity after heating at 45° C. for 10 minutes, preferably those maintaining 30% or more of the activity after heating at 45° C. for 10 minutes, more preferably those maintaining 50% or more of the activity after heating at 50° C. for 10 minutes, even more preferably those maintaining 60% or more of the activity after heating at 55° C. for 10 minutes, further preferably those maintaining 70% or more of the activity after heating at 60° C. for 10 minutes.

The thermostable 1,5-AG dehydrogenase of the present invention is preferably, for example, the following proteins, as shown later in FIGS. 3-1, 3-2 and 3-3:

1) a protein comprising an amino acid sequence represented by SEQ ID NO: 1 which has all the variations described in (1) except for the variation at position 6, wherein the variation of the amino acid residue at position 37 is to an arginine residue (hereinafter, this protein is also referred to as Ver. 12.0);

2) a protein comprising an amino acid sequence represented by SEQ ID NO: 1 having an arginine residue in place of a proline residue at position 156 (hereinafter, this protein is also referred to as Ver. 11.1);

3) a protein comprising an amino acid sequence represented by SEQ ID NO: 1 having an arginine residue in place of a proline residue at position 156 and a valine residue in place of an alanine residue at position 473 (hereinafter, this protein is also referred to as Ver. 11.0);

4) a protein comprising an amino acid sequence represented by SEQ ID NO: 1 having a glutamic acid residue in place of a glycine residue at position 67, an arginine residue in place of a proline residue at position 156, and a valine residue in place of an alanine residue at position 473 (hereinafter, this protein is also referred to as Ver. 10.0);

5) a protein comprising an amino acid sequence represented by SEQ ID NO: 1 having a glutamic acid residue in place of a glycine residue at position 67, an asparagine residue in place of a tyrosine residue at position 80, an arginine residue in place of a proline residue at position 156, and a valine residue in place of an alanine residue at position 473 (hereinafter, this protein is also referred to as Ver. 9.0);

6) a protein comprising an amino acid sequence represented by SEQ ID NO: 1 having a glutamic acid residue in place of a glycine residue at position 67, an asparagine residue in place of a tyrosine residue at position 80, an asparagine residue in place of an aspartic acid residue at position 202, and a valine residue in place of an alanine residue at position 473 (hereinafter, this protein is also referred to as Ver. 8.4);

7) a protein comprising an amino acid sequence represented by SEQ ID NO: 1 having a glutamic acid residue in place of a glycine residue at position 67, an asparagine residue in place of a tyrosine residue at position 80, an arginine residue in place of a proline residue at position 156, and an asparagine residue in place of an aspartic acid residue at position 202 (hereinafter, this protein is also referred to as Ver. 8.2);

8) a protein comprising an amino acid sequence represented by SEQ ID NO: 1 having a glutamic acid residue in place of a glycine residue at position 67, an arginine residue in place of a proline residue at position 156, an asparagine residue in place of an aspartic acid residue at position 202, and a valine residue in place of an alanine residue at position 473 (hereinafter, this protein is also referred to as Vet 8.1);

9) an amino acid sequence represented by SEQ ID NO: 1 having a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473 (hereinafter, this protein is also referred to as Ver. 8.0);

10) a protein comprising an amino acid sequence represented by SEQ ID NO: 1 having a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473 (hereinafter, this protein is also referred to as Ver. 7.1);

11) a protein comprising an amino acid sequence represented by SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473 (hereinafter, this protein is also referred to as Ver. 7.0);

12) a protein comprising an amino acid sequence represented by SEQ ID NO: 1 having a threonine residue in place of an arginine residue at position 37, a glutamic acid residue in place of a glycine residue at position 67, an asparagine residue in place of a tyrosine residue at position 80, an arginine residue in place of a praline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473 (hereinafter, this protein is also referred to as Vet 6.1);

13) a protein comprising an amino acid sequence represented by SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, an asparagine residue in place of a tyrosine residue at position 348, and a valine residue in place of an alanine residue at position 473 (hereinafter, this protein is also referred to as Ver. 6.0);

14) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, and a valine residue in place of an alanine residue at position 473 (hereinafter, this protein is also referred to as Ver. 5.1);

15) a protein comprising an amino acid sequence represented by SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473 (hereinafter, this protein is also referred to as Ver. 5.0);

16) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473 (hereinafter, this protein is also referred to as Ver. 4.0);

17) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473 (hereinafter, this protein is also referred to as Ver. 3.2);

18) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473 (hereinafter, this protein is also referred to as Vet 3.1);

19) a protein comprising an amino acid sequence represented by SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, and a valine residue in place of an alanine residue at position 473 (hereinafter, this protein is also referred to as Ver. 3.0);

20) a protein comprising an amino acid sequence represented by SEQ ID NO: 1 having a glycine residue in place of an alanine residue at position 4, a histidine residue in place of a glutamine residue at position 6, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473 (hereinafter, this protein is also referred to as Ver. 2.0); and 21) a protein comprising an amino acid sequence represented by SEQ ID NO: 1 having a glycine residue in place of an alanine residue at position 4, a serine residue in place of a threonine residue at position 14, an alanine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473 (hereinafter, this protein is also referred to as Ver. 1.0).

Moreover, a thermostable protein which comprises an amino acid sequence derived from each of these amino acid sequences of 1) to 21) by addition, deletion or substitution of one or more, preferably approximately 1 to 20, particularly preferably approximately 2 to 10 amino acid residues other than an amino acid residue corresponding to the varied amino acid residue in the amino acid sequence represented by SEQ ID NO: 4 and has a 1,5-AG dehydrogenase activity is also encompassed in the present invention as a preferable thermostable 1,5-AG dehydrogenase.

On the other hand, the protein comprising an amino acid sequence having at least one variation described in (1) as the thermostable protein of the present invention having a 1,5-AG dehydrogenase activity can be defined, based on the amino acid sequence represented by SEQ ID NO: 1, as a protein comprising the amino acid sequence represented by SEQ ID NO: 1 or as a protein comprising an amino acid sequence represented by SEQ ID NO: 1 maintaining at least one of an alanine residue at position 4, a glutamine residue at position 6, a threonine residue at position 14, an arginine residue at position 37, a glutamine residue at position 50, a glycine residue at position 67, a tyrosine residue at position 80, a methionine residue at position 93, a proline residue at position 156, a methionine residue at position 164, an aspartic acid residue at position 202, an alanine residue at position 235, a tyrosine residue at position 348, an arginine residue at position 362 and an alanine residue at position 473. Moreover, the protein described in (2) can be defined as a thermostable protein which comprises an amino acid sequence derived therefrom by addition, deletion or substitution of one or more amino acids other than the maintained amino acid and has 1,5-anhydroglucitol dehydrogenase activity.

Moreover, the thermostable 1,5-AG dehydrogenase of the present invention may be fused at its N- or C-terminus with an additional protein or a peptide by a usual method without inhibiting the 1,5-AG dehydrogenase activity. In this context, examples of the additional protein or the peptide include, but not limited to, glutathione S-transferase (GST) and histidine tag (His-Tag).

The present invention also encompasses a gene comprising a DNA encoding the thermostable 1,5-AG dehydrogenase or a DNA which hybridizes under stringent conditions to a DNA comprising a nucleotide sequence complementary to the DNA encoding the thermostable 1,5-AG dehydrogenase and encodes a thermostable protein having a 1,5-AG dehydrogenase activity.

Examples of the DNA encoding the thermostable 1,5-AG dehydrogenase of the present invention include a DNA having a nucleotide sequence represented by SEQ ID NO: 2 encoding the thermostable 1,5-AG dehydrogenase comprising the amino acid sequence represented by SEQ ID NO: 1. However, all genes are encompassed in the present invention without particular limitations as long as they are genes encoding the amino acid sequences of thermostable 1,5-AG dehydrogenases.

A method for obtaining the thermostable 1,5-AG dehydrogenase of the present invention is not particularly limited and is achieved by, for example, a method comprising introducing a variation to a 1,5-AG dehydrogenase-encoding gene, followed by screening.

The introduction of a variation in a 1,5-AG dehydrogenase-encoding gene refers to the procedure of imparting thermostability to 1,5-AG dehydrogenase by substitution or the like of approximately 1 to 10 bases in the nucleotide sequence of a gene encoding the original 1,5-AG dehydrogenase having no thermostability by other bases. The thermostability can be further improved by repeating this procedure.

Any gene derived from an animal, a plant, or a microbe having 1,5-AG dehydrogenase can be used as the original gene to which a variation is introduced. In consideration of industrial production, those derived from a microbe are preferable. The microbe is preferably a *Pseudomonas* bacterium such as *Pseudomonas* sp. NK-85001 (International Patent Organism Depositary, National Institute of Advanced Industrial Science and Technology Accession No, FERM BP-01037; hereinafter, also referred to as a parent strain) described in PATENT DOCUMENT 3.

Examples of the amino acid sequence of the 1,5-AG dehydrogenase of the parent strain include a sequence represented by SEQ ID NO: 4. Examples of the gene encoding the enzyme include a DNA having a nucleotide sequence represented by SEQ ID NO: 3. However, all genes are encompassed in the present invention without particular limitations as long as they are genes encoding the amino acid sequences of 1,5-AG dehydrogenases.

The "nucleotide sequence hybridizing under stringent conditions" means a DNA obtained using a colony hybridization or plaque hybridization method or the like with the nucleotide sequence of a certain DNA as a probe. In this context, the "stringent conditions" refer to conditions under which so-called specific hybrids are formed without forming non-specific hybrids. Specifically, the conditions are conditions under which, for example, highly homologous DNAs or DNAs having at least approximately 50% or more, preferably approximately 60% or more, more preferably approximately 80% or more homology in their nucleotide sequences are hybridized to each other without causing hybridization between DNAs having lower homology or hybridization conditions involving approximately 0.1 to 2×SSC solution (the composition of 1×SSC solution is composed of 150 mM sodium chloride and 15 mM sodium citrate) and a temperature about 65° C. The homology is calculated using nucleotide sequence analysis software, for example, EMBOSS.

Moreover, the gene according to the present invention is meant to encompass not only DNAs but also their mRNAs and cDNAs. Thus, the gene of the present invention encompasses all of these DNAs, mRNAs and cDNAs.

In the present invention, the complementary sequence refers to a nucleotide sequence formed according to base pairing rules (adenine/thymine and cytosine/guanine) relative to the nucleotide sequence encoding the 1,5-AG dehydrogenase.

Hereinafter, a method for obtaining the 1,5-AG dehydrogenase-encoding gene represented by SEQ ID NO: 3 from the *Pseudomonas* sp. NK-85001 strain (parent strain) and a method for introducing a variation to the gene will be described. However, the present invention is not limited to them.

[1] Extraction of Genomic DNA

The extraction of genomic DNA from microbial cells (microbes) can be performed by application of a method known in the art and can be performed conveniently using a commercially available DNA extraction kit. Examples of the commercially available DNA extraction kit include Puregene DNA Isolation Kit (manufactured by Gentra Systems, Inc.), GFX Genomic Blood DNA Purification Kit (manufactured by Amersham Biosciences Corp.) and MagPrep Bacterial Genomic DNA Kit (manufactured by Novagen, Inc.).

[2] Preparation of 1,5-AG Dehydrogenase-Encoding DNA

Since the amino acid sequence of 1,5-AG dehydrogenase of the *Pseudomonas* sp. NK-85001 strain is unknown, primers were designed from some amino acid sequences homologous to enzymes that are similar in effect to the 1,5-AG dehydrogenase and have an amino acid sequence known in the art, with conservative regions of these amino acid sequences as an index.

From the sequence of *Agrobacterium tumefaciens* NT1130 strain (see JP 2000-316570 A) having an already known amino acid sequence, the amino acid sequences of several kinds, at least two or more kinds, preferably approximately 3 to 5 kinds of enzymes similar thereto are compared by homology search to select a common sequence or a highly homology sequence site. Based on the selected amino acid sequence, for example, an amino acid sequence represented by SEQ ID NO: 5 or 6, oligonucleotides are designed. PCR is performed with the designed oligonucleotides as primers to obtain a partial fragment of a 1,5-AG dehydrogenase-encoding DNA. Examples of such primers include a nucleotide sequence (SEQ ID NO: 7 or 8) corresponding to the amino acid sequence represented by SEQ ID NO: 5 or 6. The PCR reaction can utilize a PCR amplification apparatus known in the art, for example, a thermal cycler. The PCR cycle is preferably performed approximately 10 to 100 times, preferably approximately 20 to 50 times, with denaturation→annealing→extension as one cycle.

The DNA fragment obtained in PCR is subcloned into appropriate cloning vectors, for example, pGEM-T Easy Vector (manufactured by Promega Corp.). Alternatively, this fragment is directly electrophoresed on an agarose gel; then, the band of the amplified DNA is excised; and DNA is extracted and sequenced. When the fragment is subcloned into pGEM-T Easy Vector, the vectors are then introduced to, for example, *E. coli* JM109 strains to obtain transformants of these strains. These transformed strains are cultured in a medium containing an appropriate antibiotic (e.g., ampicillin or chloramphenicol), and microbial cells are collected from the cultures.

From the collected microbial cells, plasmid DNA is extracted by a standard method using, for example, QIAprep Spin Miniprep Kit (manufactured by QIAGEN). This extracted plasmid DNA can be sequenced to obtain a DNA fragment containing the partial sequence of the 1,5-AG dehydrogenase-encoding DNA of the present invention.

The obtained DNA fragment can be sequenced by application of a method known in the art, for example, a dideoxy chain termination method. Moreover, the nucleotide sequence may be analyzed automatically using, for example, ABI PRISM 3100 Genetic Analyzer (manufactured by Applied Biosystems, Inc.) which uses a capillary electrophoresis system and a multicolor fluorescence technique in detection.

In this way, the DNA fragment containing the partial sequence of the 1,5-AG dehydrogenase-encoding DNA can be sequenced, and its nucleotide sequence can be determined as, for example, a nucleotide sequence corresponding to positions 19 to 1434 in the nucleotide sequence of SEQ ID NO: 3. Subsequently, the nucleotide sequence is translated into an amino acid sequence, which is then analyzed. As a result, the translated amino acid sequence can correspond to amino acids at positions 7 to 480 in the amino acid sequence represented by SEQ ID NO: 4.

Examples of a method for obtaining a DNA fragment containing the whole sequence of the 1,5-AG dehydrogenase-encoding DNA include a method comprising preparing a chromosomal DNA library of the parent strain and isolating chromosomal DNA containing the 1,5-AG dehydrogenase-encoding DNA by southern hybridization with the partial fragment of the 1,5-AG dehydrogenase-encoding DNA (e.g., the nucleotide sequence corresponding to positions 19 to 1434 of SEQ ID NO: 3; the same holds true for the description below) as a probe.

The chromosomal DNA thus extracted from the parent strain is digested with an appropriate restriction enzyme, for example, HindIII or NcoI and electrophoresed on an agarose gel. Then, this fragment is transferred to a nylon membrane (Hybond N+, manufactured by Amersham Biosciences Corp.) and subjected to southern hybridization with the partial fragment of the 1,5-AG dehydrogenase-encoding DNA as a probe.

When the restriction enzyme-digested fragment of the *Pseudomonas* (e.g., *Pseudomonas* sp. NK-85001 strain)-derived chromosomal DNA containing the partial fragment of the 1,5-AG dehydrogenase-encoding DNA obtained by these procedures is within 7 kb, this restriction enzyme-digested fragment is self-ligated. In this way, circular DNA containing the partial fragment of the 1,5-AG dehydrogenase-encoding DNA can be obtained.

Next, the circular DNA thus obtained is used as a template to perform inverse PCR using primers designed based on the determined partial fragment of the 1,5-AG dehydrogenase-encoding DNA. For example, sites corresponding to nucleotide sequences represented by positions 81 to 102 and positions 1286 to 1307 of SEQ ID NO: 3 are selected, and their nucleotide sequences or complementary sequences thereof, for example, SEQ ID NO: 9 or 10, can be designed as such primers.

The DNA fragment thus obtained by inverse PCR is a fragment containing both the terminal regions of the 1,5-AG dehydrogenase-encoding DNA. This fragment is electrophoresed on an agarose gel, and DNA is then excised from the gel, extracted, and directly sequenced. Alternatively, the fragment is subcloned into appropriate cloning vectors, for example, pGEM-T Easy Vector (manufactured by Promega Corp.) and used in the transformation of *E. coli* JM109 strains, and DNA inserted in this plasmid can be sequenced to thereby determine a DNA encoding the *Pseudomonas* sp. NK-85001 strain (parent strain)-derived original 1,5-AG dehydrogenase having no thermostability.

Examples of the restriction enzyme-cleaved fragment containing the 1,5-AG dehydrogenase-encoding DNA hybridized by southern hybridization can include a DNA fragment of approximately 4 kb in size obtained by cleaving *Pseudomonas* sp. NK-85001 strain-derived chromosomal DNA with a restriction enzyme HindIII and a DNA fragment of approximately 5 kb in size obtained by cleaving the fragment with a restriction enzyme NcoI. As a result of sequencing this DNA fragment, the presence of an open reading frame was confirmed, demonstrating that its structural gene region is composed of 1491 base pairs encoding a 497-amino acid sequence from amino acid Nos. 1 to 497 in an amino acid sequence represented by SEQ ID NO: 11 in SEQUENCE LISTING.

[3] Preparation of Recombinant DNA

Next, based on the N-terminal and C-terminal sequence-encoding nucleotide sequences of the open reading frame of the 1,5-AG dehydrogenase-encoding gene represented by SEQ ID NO: 11, oligonucleotides are designed. PCR is performed with the designed oligonucleotides as primers and the extracted genomic DNA as a template to obtain a 1,5-AG dehydrogenase-encoding DNA. Examples of such primers include primers having a nucleotide sequence represented by SEQ ID NO: 12 or 13. The primer having a nucleotide sequence represented by SEQ ID NO: 12 adds the sequences of NcoI and EcoRI restriction sites to upstream of the sequence encoding the N-terminal sequence of the 1,5-AG dehydrogenase, while the primer having a nucleotide sequence represented by SEQ ID NO: 13 adds the sequence of a BamHI restriction site to downstream of the sequence encoding the C-terminal sequence of the 1,5-AG dehydrogenase. The sequences of the restriction sites are not limited to them and are preferably selected appropriately according to the relationship with the sequences of restriction sites contained in a multicloning site carried by vectors described later.

The DNA fragment obtained by PCR can be treated with restriction enzymes, for example, EcoRI and BamHI, and ligated to expression vectors also treated with these restriction enzymes to obtain expression vectors. The expression vectors can be introduced into microbes, for example, *E. coli*, by a method known in the art to clone the gene.

The gene introduction to microbes such as *E. coli* and the expression of the gene can be performed by any usual method of genetic engineering experiments. Since information about vectors of various microbes such as *E. coli* and foreign gene introduction/expression methods are described in many experimental manuals (e.g., Sambrook, J., Russell, D. W., Molecular Cloning A Laboratory Manual, 3rd Edition, CSHL Press, 2001), vector selection, gene introduction and expression can be performed according to them.

Subsequently, a method for obtaining the thermostable 1,5-AG dehydrogenase will be described focusing on methods of EXAMPLES described later. However, the present invention is not limited to these methods.

The introduction of a variation to the gene encoding the original 1,5-AG dehydrogenase having no thermostability will be described.

The cloned gene derived from the parent strain can be treated with any commercially available kit for mutagenesis or the like. Specifically, the kit for mutagenesis can be operated according to the protocol or the like of the kit using vectors having an insert of the 1,5-AG dehydrogenase-encoding gene to thereby randomly introduce variations in the 1,5-AG dehydrogenase-encoding gene with very high frequency while amplifying the varied gene (hereinafter, referred to as a variant gene) by PCR. Examples of such a kit for mutagenesis include, but not limited to, GeneMorph Random Mutagenesis Kit containing Mutazyme DNA polymerase (manufactured by Stratagene Corp.), GeneTailor (registered trademark) Site-Directed Mutagenesis System (manufactured by Invitrogen Corp.), Mutan (registered trademark)-Super Express Km (manufactured by TAKARA BIO INC.) and Diversity PCR Random Mutagenesis Kit (manufactured by BD Biosciences).

Moreover, to cause site-directed mutagenesis in the gene encoding the original 1,5-AG dehydrogenase having no thermostability, for example, to introduce a variation for substituting an amino acid residue at a particular site or introduce a variation for deleting a particular site, the site-directed mutagenesis can be achieved by PCR amplification using primers having these variations. Moreover, two plasmid DNAs containing 1,5-AG dehydrogenase-encoding genes differing in variation can be ligated to obtain a gene having a larger number of variations introduced therein. Moreover, a 1,5-AG dehydrogenase-encoding gene having a variation can also be amplified by PCR using primers having a variation different therefrom to thereby further introduce variations.

The PCR product of the amplified variant gene having the variations thus introduced therein using the kit for mutagenesis is preferably purified using a kit for DNA purification. Examples of the kit for purification include, but not limited to, QIAquick PCR purification Kit (manufactured by QIAGEN), SpinClean (registered trademark) PCR Purification Kit (manufactured by Mbiotech, Inc.), AMPure (registered trademark) PCR Product Cleanup Kit (manufactured by PerkinElmer Inc.), JETFLEX Genomic DNA Purification Kit (manufactured by GENOMED GmbH), GFX 96 PCR Purification Kit (Amersham Biosciences Corp.) and AutoSeq G-50 (Pharmacia).

The purified PCR product of the variant gene is cleaved with the above-described two kinds of restriction enzymes, for example, EcoRI and BamHI. Then, DNA purification from the agarose gel is preferably performed. The purification can employ a commercially available kit, and, for example, but not limited to, QIAquick Gel Extraction Kit (manufactured by QIAGEN) or S.N.P.UV-Free Gel Purification Kit (manufactured by Invitrogen Corp.) can be used. The purified PCR product of the variant gene is inserted into appropriate vectors for expression, with which hosts can then be transformed to construct a variant gene library.

Examples of the vectors for expression include: bacterial plasmids (pBluescript SK+, pBluescript KS+, pUC18, pUC19, pBR322, pET16b, pET21d (+), pET32a (+), pCITE4a, pGEX-5X-1, pGEX-5X-3, pMAL-p2, pMAL-c2, pBridge Vector, pKF18k DNA, pKF19k DNA, pTrc99A (manufactured by Amersham Biosciences Corp.), pSPORT 1, Charmomid 9-36 DNA, pEU-DFR, pIVEX 2.3-MCS, pIVEX 2.4c, pIVEX 2.4b Nde, pIVEX 2.4a, etc.); phage DNAs (random phages, etc.); yeast plasmids (pG-1, etc.); vectors for mammalian cells, such as viral DNAs, for example, baculoviral, vaccinia viral and adenoviral DNAs; and SV40 and derivatives thereof. Any of other vectors can be used as long as they are replicable in hosts.

Moreover, vectors having a chaperone-encoding gene insert used for stabilizing, solubilizing and expressing foreign proteins in host cells (e.g., pG-KJE8, pGro7, pKJE7, pG-Tf2 and pTf16; all manufactured by TAKARA BIO INC.) can also be allowed to coexist in the hosts.

The vectors contain, for example, a replication origin, a selection marker and a promoter and may optionally contain an enhancer, a transcription termination sequence (terminator), a ribosome-binding site, a polyadenylation signal, and so on. The vectors preferably contain a polylinker having various restriction enzyme sites therewithin or contain a single restriction enzyme site. Examples of such restriction enzyme sites include EcoRI, BamHI, PstI, NcoI, SalI, KpnI and HindIII sites. These restriction enzyme sites are cleavable with restriction enzymes EcoRI, BamHI, PstI, NcoI, SalI, KpnI and HindIII, respectively.

The gene introduction to the vectors can be performed by application of means known in the art. Specifically, particular restriction enzyme sites (e.g., EcoRI and BamHI) in the vectors are cleaved with particular restriction enzymes (e.g., EcoRI and BamHI), and the gene of the present invention is preferably inserted to the cleavage site. Furthermore, depending on the vectors used, the gene introduction can also be performed such that the thermostable 1,5-AG dehydrogenase of the present invention is produced in a form fused at its N-terminus or C-terminus, or both, with a protein serving as an index, for example, GST or His-Tag. For example, when the pET16b is used as expression vectors, the 1,5-AG dehydrogenase of the present invention may be produced in a form fused at its N-terminus with His-Tag that can be cleaved off by degradation with particular protease. In this way, recombinant vectors containing the gene of the present invention are prepared.

[4] Creation of Transformant

Examples of the hosts include: bacteria such as *E. coli* (e.g., *E. coli* JM109 and BL21 (DE3) strains), *Corynebacterium*, *Bacillus*, *Actinomyces* such as the genus *Streptomyces*, and *Bacillus subtilis*; cells of fungi such as *Aspergillus* strains; cells of yeasts such as bakers' yeast and methanol-utilizing yeast; insect cells such as *Drosophila* S2 and *Spodoptera* Sf9; mammalian cells including cultured human cells, such as CHO, COS, BHK, 3T3 and C127; and competent cells thereof. *E. coli* competent cells are preferable.

The transformation can be performed by a method, for example, a calcium chloride/rubidium chloride method, a calcium phosphate method, DEAE-dextran-mediated transfection or electroporation. Specifically, for example, the expression vectors having the insert of the variant gene can be mixed with E. coli JM109 competent cells to obtain microbial transformants.

[5] Culture of Transformant

The microbes thus transformed with the expression vectors having the variant gene insert (hereinafter, simply referred to as transformed microbes) are preferably cultured in a medium (e.g., a microbial culture medium described below) with pH on the order of 5.0 to 8.0 at a culture temperature of approximately 20 to 40° C. for a culture time of approximately 1 to 7 days.

[6] Method for Selecting Variant Strain Producing Thermostable 1,5-AG Dehydrogenase Screening for selecting thermostable 1,5-AG dehydrogenase-producing variant strains from the gene library can be performed rapidly by small-scale culture using, for example, a 96-well deep well plate. Specifically, colonies of the variant gene library are picked up using, for example, a colony picker. The microbial cells (microbes) of the colonies are cultured in approximately 0.1 to 1.0 mL, preferably approximately 0.5 mL of a microbial culture medium or the like using, for example, a 96-well plate to obtain microbial cells. These microbial cells are treated by heating at approximately 50 to 70° C. for approximately 10 to 120 minutes, preferably approximately 30 minutes. The microbial cells thus treated are reacted with a reaction solution containing 1,5-AG and a chromogenic substrate at room temperature for approximately 10 to 240 minutes. The residual 1,5-AG dehydrogenase can be confirmed based on change such as color development from the chromogenic substrate or color degradation. In this way, thermostable 1,5-AG dehydrogenase variants whose 1,5-AG dehydrogenase activity remains even after heat treatment can be obtained.

[7] Determination of Thermostable 1,5-AG Dehydrogenase Activity

The 1,5-AG dehydrogenase activity can be determined, for example, by adding cell-free extracts prepared from the transformed microbes to a reaction solution containing 1,5-AG or L-sorbose in the presence of a chromogenic substrate and an electron carrier and incubating the mixture at preferably 4 to 50° C., particularly preferably 25 to 40° C., for preferably 1 minute to 3 hours, more preferably 1 to 30 minutes, particularly preferably 1 to 10 minutes, while measuring change in absorbance.

For information, L-sorbose can be used instead of 1,5-AG as a substrate for 1,5-AG dehydrogenase, and this is because the substrate specificity of the 1,5-AG dehydrogenase for 1,5-AG is comparable to that for L-sorbose. L-sorbose is not contained in clinical samples and therefore does not interfere with the assay of 1,5-AG in practical use.

Examples of the cell-free extracts include 1,5-AG dehydrogenase-containing supernatants of centrifugation following the disruption of the transformed microbes using, for example, ultrasonic waves or glass beads in a water medium.

The 1,5-AG dehydrogenase activity in the cell-free extracts before and after mutagenesis can be compared between before and after heat treatment at 45 to 60° C. for 10 to 30 minutes to thereby confirm a 1,5-AG dehydrogenase having thermostability improved by mutagenesis.

[8] Sequencing of Gene Encoding Thermostable LS-AG Dehydrogenase

The cells of the transformed microbes thus obtained by screening are cultured under static standing or stirring at approximately 20 to 40° C. for approximately 1 hour to 48 hours in a microbial culture medium (e.g., an LB medium) containing approximately 50 to 200 µg/mL, preferably approximately 100 µg/mL ampicillin. From the culture solution, microbial cells (microbes) can be obtained by centrifugation. From the obtained microbial cells, plasmid DNA is extracted. The plasmid DNA extraction can be performed by application of a method known in the art. Alternatively, plasmid DNA can be extracted conveniently using a commercially available DNA extraction kit. Examples of the commercially available DNA extraction kit include QIAquick Plasmid Purification Kit (manufactured by QIAGEN). This extracted plasmid DNA can be sequenced to thereby determine a total DNA encoding the thermostable 1,5-AG dehydrogenase of the present invention.

In this way, the nucleotide sequence of the DNA encoding the thermostable 1,5-AG dehydrogenase can be determined. The gene comprising the nucleotide sequence represented by SEQ ID NO: 2 is a gene comprising a nucleotide sequence represented by SEQ ID NO: 3 (gene encoding the parent strain-derived 1,5-AG dehydrogenase) having variations of guanine at position 11 to cytosine, thymine at position 40 to adenine, thymine at position 99 to cytosine, guanine at position 109 to adenine, cytosine at position 110 to guanine, adenine at position 111 to guanine, cytosine at position 149 to adenine, adenine at position 200 to guanine, adenine at position 238 to thymine, guanine at position 277 to adenine, guanine at position 467 to cytosine, cytosine at position 490 to adenine, adenine at position 604 to guanine, adenine at position 703 to guanine, adenine at position 1042 to thymine, guanine at position 1084 to adenine and thymine at position 1418 to cytosine.

Subsequently, the nucleotide sequence is translated into an amino acid sequence, which can then be analyzed to thereby determine the whole amino acid sequence of the thermostable 1,5-AG dehydrogenase represented by SEQ ID NO: 1. The amino acid sequence of the thermostable protein having a 1,5-AG dehydrogenase activity represented by SEQ ID NO: 1 is an amino acid sequence of the parent strain-derived 1,5-AG dehydrogenase represented by SEQ ID NO: 4 having an amino acid residue at position 4 changed from a glycine residue to an alanine residue, an amino acid residue at position 14 changed from a serine residue to a threonine residue, an amino acid residue at position 37 changed from an alanine residue to an arginine residue, an amino acid residue at position 50 changed from a proline residue to a glutamine residue, an amino acid residue at position 67 changed from a glutamic acid residue to a glycine residue, an amino acid residue at position 80 changed from an asparagine residue to a tyrosine residue, an amino acid residue at position 93 changed from a valine residue to a methionine residue, an amino acid residue at position 156 changed from an arginine residue to a proline residue, an amino acid residue at position 164 changed from a leucine residue to a methionine residue, an amino acid residue at position 202 changed from an asparagine residue to an aspartic acid residue, an amino acid residue at position 235 changed from a threonine residue to an alanine residue, an amino acid residue at position 348 changed from an asparagine residue to a tyrosine residue, an amino acid residue at position 362 changed from a glycine residue to an arginine residue, and a valine residue at position 473 changed to an alanine residue.

Next, a method for producing the thermostable 1,5-AG dehydrogenase from the transformed microbes containing the variant gene will be described below. However, the present invention is not particularly limited to this method.

[1] Culture of Transformed Microbes

Any medium can be used preferably as the microbial culture medium as long as it is used in usual microbial culture. Examples thereof include natural or synthetic media containing a carbon source, a nitrogen source, an inorganic salt and other nutrients, and so on.

Examples of the carbon source include: sugars or sugar alcohols such as glucose, fructose, sucrose, mannose, maltose, mannitol, xylose, galactose, starch, molasses, sorbitol and glycerin; organic acids such as acetic acid, citric acid, lactic acid, fumaric acid, maleic acid and gluconic acid; and alcohols such as ethanol and propanol. Moreover, for example, hydrocarbon such as normal paraffin can be used, if desired. These carbon sources may be used alone or as a mixture of two or more thereof.

The concentration of the carbon source in the medium is usually on the order of 0.1 to 10% by weight.

Examples of the nitrogen source include: inorganic or organic ammonium compounds such as ammonium chloride, ammonium sulfate, ammonium nitrate and ammonium acetate; inorganic nitrates such as sodium nitrate and potassium nitrate; and urea and ammonia water. Moreover, for example, a nitrogen-containing organic compound such as NZ-amine or amino acids may be used. These nitrogen sources may be used alone or as a mixture of two or more thereof.

The concentration of the nitrogen source in the medium differs depending on the nitrogen compound used and is usually on the order of 0.1 to 10% by weight.

Examples of the inorganic salt include potassium dihydrogen phosphate, dipotassium phosphate, magnesium sulfate, sodium chloride, iron (II) nitrate, manganese sulfate, zinc sulfate, cobalt sulfate and calcium carbonate. These inorganic salts may be used alone or as a mixture of two or more thereof.

The concentration of the inorganic salt in the medium differs depending on the inorganic salt used and is usually on the order of 0.01 to 1.0% by weight.

Examples of the other nutrients include meat extracts, peptone, polypeptone, yeast extracts, dry yeast, corn steep liquor, skimmed milk powder, hydrochloric acid hydrolysates of defatted soybean and extracts of animal, plant or microbial cells, or degradation products thereof.

The concentration of the nutrient in the medium differs depending on the nutrient used and is usually on the order of 0.1 to 10% by weight.

The pH of the medium is preferably on the order of 5.0 to 8.0.

Examples of a preferable microbial culture medium include LB (Luria-Bertani medium; 10 g/L tryptone, 5 g/L yeast extracts, 10 g/L sodium chloride), NZYM, Terrific Broth, SOB, 2xYT, AHC, x1776, M9, YPD, SD, YPAD and Super broth media. Moreover, the medium may contain vitamins, an antibiotic (e.g., ampicillin, chloramphenicol or tetracycline) and a gene expression-inducing material (e.g., isopropyl-(β-D-1-thiogalactopyranoside, arabinose or tetracycline), if desired. Culture conditions, for example, a temperature, medium pH and a culture time may be selected appropriately such that the amount of the thermostable 1,5-AG dehydrogenase produced is increased.

[2] Purification of 1,5-AG Dehydrogenase

As described above, the cells of the microbes (e.g., *E. coli* JM109 strains) as hosts expressing the thermostable 1,5-AG dehydrogenase can be collected from the culture solution by procedures such as centrifugation. The obtained microbial cells are suspended in various appropriate buffers and then subjected to mechanical treatment such as sonication or enzymatic treatment such as lysozyme treatment to disrupt or lyse the microbial cells. Then, cell-free extracts containing the thermostable 1,5-AG dehydrogenase can be obtained by procedures such as centrifugation. Furthermore, the thermostable 1,5-AG dehydrogenase can be purified by application of purification procedures such as salting out, various affinity chromatography techniques, ion-exchange chromatography and gel filtration chromatography combined according to the purpose.

Furthermore, when the thermostable 1,5-AG dehydrogenase is produced in the form of a fusion protein with an additional protein in the transformants, the thermostable 1,5-AG dehydrogenase can be purified with the protein as an index. For example, His-Tag-fused proteins can be purified using a commercially available kit such as His GraviTrap (GE Healthcare Biosciences) or can be purified at higher purity by combining the kit with the purification methods.

Subsequently, a method for assaying 1,5-AG using the thermostable 1,5-AG dehydrogenase of the present invention will be described.

[3] Method for Assaying 1,5-AG

The method for assaying 1,5-AG according to the present invention can employ clinical samples such as blood (total blood, serum or plasma), urine or spinal fluid and permits highly precise and accurate measurement of 1,5-AG concentrations in the clinical samples. Since 1,5-AG in blood well reflects the control state of blood sugar, the method for assaying 1,5-AG according to the present invention is useful in the diagnosis of diabetes mellitus or high postprandial blood sugar levels.

The method for assaying 1,5-AG according to the present invention is, for example, colorimetry which involves reducing a reductive chromogenic agent for color development and measuring absorbance to quantify 1,5-AG or an electrochemical method which involves converting an oxidized form of a redox mediator to a reduced form and measuring an electrochemical signal formed by returning it to the oxidized form on electrodes to quantify 1,5-AG.

The absorptiometry includes various possible methods. In the method for assaying 1,5-AG according to the present invention, a method can be used which comprises reducing a reductive chromogenic agent for color development in the presence or absence of an electron acceptor. Among others, a method is preferable which comprises directly reducing the reductive chromogenic agent for color development in the absence of an electron acceptor. Examples of the chromogenic substrate reduced for color development include 2-(4-iodophenyl)-3-(4-nitrophenyl)-5-phenyl-2H-tetrazolium chloride (INT), 3-(4,5-dimethyl-2-thiazolyl)-2,5-diphenyl-2H-tetrazolium bromide (MTT), 3,3'-[3,3'-dimethoxy-(1,1'-biphenyl)-4,4'-diyl]-bis[2-(4-nitrophenyl)-5-phenyl-2H-tetrazolium chloride] (NTB), 3,3'-[3,3'-dimethoxy-(1,1'-biphenyl)-4,4'-diyl]-bis[2,5-diphenyl-2H-tetrazolium chloride] (TB), 2-(4-iodophenyl)-3-(4-nitrophenyl)-5-(2,4-disulfophenyl)-2H-tetrazolium monosodium salt (WST-1), 2-(4-iodophenyl)-3-(2,4-dinitrophenyl)-5-(2,4-disulfophenyl)-2H-tetrazolium monosodium salt (WST-3) and 2,6-dichlorophenolindophenol (DCIP). WST-1 is preferable.

Moreover, the electron acceptor used in the method which comprises reducing a reductive chromogenic agent in the presence of the electron acceptor, followed by quantification is not particularly limited and is preferably 1-methoxy phenazine methosulfate (1-m-PMS), diaphorase, or the like. The coexistence of these electron acceptors in the reaction system can potentiate reduction reaction and may enhance assay sensitivity.

The electrochemical method also includes various possible methods. In the method for assaying 1,5-AG according to the present invention, for example, a method can be used which comprises performing measurement using a redox mediator responsible for mediating the donation or acceptance of electrons involved in oxidation-reduction reaction. Examples of the redox mediator include oxidized or reduced mediators. Oxidized mediators are preferable. Among them, osmium complexes, quinone compounds, ferrocene compounds, phenothiazine compounds, phenoxazine compounds, phenazine compounds, indophenol compounds and diphenylamine compounds are more preferable.

Examples of the osmium complexes include [Os(III)(bipyridyl)$_2$(imidazoyl)Cl]Cl$_2$ and polymers thereof.

Examples of the quinone compounds include benzoquinone, 2-methyl benzoquinone, 2,6-dimethyl benzoquinone, 2,6-dichlorobenzoquinone, 2,5-dihydroxybenzoquinone, 2-hydroxy-1,4-naphthoquinone, 2-methyl-1,4-naphthoquinone, 2,3-dimethyoxy-5-methyl-1,4-benzoquinone, pyrroloquinoline quinone (PQQ) and ubiquinone.

Examples of the ferrocene compounds include ferrocenyl PEG, ferrocenyl TMA, N,N-dimethylaminomethylferrocene and ferrocenemethanol.

Examples of the phenothiazine compounds include thionine, methylene blue, methylene green, 10-(carboxymethylaminocarbonyl)-3,7'-bis(dimethylamino)-phenothiazine sodium salt, toluidine blue, azure I, azure B, azure A, azure C, new methylene blue and benzoyl leucomethylene blue.

Examples of the phenoxazine compounds include Meldola's blue.

Examples of the phenazine compounds include phenazine methosulfate, 1-m-PMS, safranine and phenosafranine.

Examples of the indophenol compounds include DCIP.

Examples of the diphenylamine compounds include 4,4'-bis(dimethylamino)diphenylamine (BG), N-(carboxymethylaminocarbonyl)-4,4'-bis(dimethylamino)-diphenylamine sodium salt, N-methyl-N-phenyl-1,4-phenylenediamine hydrochloride and N-methyl-N-(3-methoxyphenyl)-1,4-phenylenediamine hydrochloride.

Among them, examples of a preferable redox mediator include thionine acetate, thionine chloride and methylene blue.

Additional examples of the redox mediator that may be used include ferricyanide compounds (e.g., potassium ferricyanide), ruthenium complexes or polymers thereof, bipyridine compounds (e.g., methyl viologen), triphenylmethane compounds (e.g., malachite green and TPM-PS), benzothiazoline compounds (e.g., 2-hydrazono-2,3-dihydro-3-methyl-6-benzothiazole and sulfonates thereof), cyanine compounds (e.g., gallocyanine, phthalocyanine and phycocyanin), azo compounds (e.g., magenta J-3GL, yellow C-Y9 and black C-BK4), bipyridylazo compounds (e.g., 5-Br-PSAA, 5-Br-PAPS and TAMSMB), aniline or derivatives thereof (e.g., DAPS, HALPS, ADPS, ALPS, TOOS and ALOS), polyaniline or derivatives thereof, phenol compounds (e.g., p-aminophenol), phenylenediamine compounds (e.g., variamine blue B and 2,3,5,6-tetramethyl-p-phenylenediamine), rhodamine compounds (e.g., rhodamine B), xanthene compounds (e.g., pyronin Y, pyronin B and sodium fluorescein), isoalloxazine compounds (e.g., riboflavin and FAD), indigo compounds (e.g., indigotrisulfonic acid and indigo carmine), phenanthroline compounds (e.g., sodium bathocuproine sulfonate and sodium bathophenanthroline sulfonate), sulfonephthalein compounds (e.g., methyl thymol blue), benzidine compounds (e.g., TMBZ, TMBZ/PS, DAB and anisidine blue), tetrazolium compounds (e.g., WST-1, MTT, Nitro-TB and XTT), cytochrome C or lumichrome, ferredoxins, EDTAs, L-ascorbic acid, FAD, NAD and NADP.

Examples of the electrodes used in the electrochemical method include gold, platinum, carbon, palladium, silver and silver-silver chloride electrodes.

Two or three electrodes may be used as the electrodes. When two electrodes are used, these electrodes are preferably a working electrode made of carbon and a counter electrode made of silver-silver chloride. When three electrodes are used, these electrodes are preferably working and counter electrodes made of carbon and a reference electrode made of silver-silver chloride.

Examples of the measurement method include amperometry, coulometry, a potential sweep method and cyclic voltammetry. Among them, amperometry or coulometry is preferable.

The optimum potential can be selected as a measurement potential within the range of −1.0 V to 1.0 V, and a potential in the range of −0.2 V to 0.2 V around 0 V, which is unsusceptible to biogenic substances, is preferable.

1,5-AG is a compound comprising glucose reduced at position 1 and is very similar in chemical structure to glucose. Therefore, many enzymes used in the assay of 1,5-AG also react with glucose. The blood of healthy individuals contains glucose in an amount 20 times or more larger than that of 1,5-AG. Thus, for assaying 1,5-AG using enzymes, glucose must be removed or converted by some method to prevent glucose from reacting with the enzyme for 1,5-AG assay. Moreover, when glucose derivatives formed by this conversion further react with the enzyme for 1,5-AG assay, these derivatives must also be removed or converted.

Since the thermostable 1,5-AG dehydrogenase of the present invention is also an enzyme that reacts, albeit at a low level, with glucose as described later, this step is preferably incorporated in the present invention for more accurate 1,5-AG assay.

The method for removing glucose and/or its derivatives or converting them to substances that do not interfere with assay is, for example, a method typified by an adsorption/removal method using an ion-exchange resin or an enzymatic conversion method. Although both of these methods may be performed in combination, the enzymatic conversion method is preferable.

Examples of the enzymatic conversion method include a method comprising enzymatically oxidizing or phosphorylating glucose. A preferable method comprises phosphorylating glucose with hexokinase or glucokinase. A particularly preferable method comprises phosphorylating glucose by an enzymatic cycling method performed using hexokinase or glucokinase in the presence of for example, magnesium ions, ATP, phosphoenolpyruvic acid (PEP) and pyruvate kinase (PK).

A method for assaying 1,5-AG using the thermostable 1,5-AG dehydrogenase of the present invention, wherein the assay method is performed in the presence of a protein such as albumin is also encompassed in the present invention.

The albumin is preferably bovine serum albumin. The coexistence of a protein such as albumin activates the thermostable 1,5-AG dehydrogenase, enhances assay sensitivity and suppresses the adsorption of the enzyme to assay cells or the like. As a result, the repetitive assay of 1,5-AG has been achieved.

An assay kit of the present invention is, for example, a diagnostic kit for general-purpose automatic analyzers for handling a large number of samples used in testing center or the like, a diagnostic kit for Point of Care Testing (POCT) also used in small-and-medium-sized hospitals or the like, or a kit for self-diagnosis available as a bedside or domestic diagnostic kit.

The diagnostic kit for general-purpose automatic analyzers is usually composed of two reagents (R1 and R2) of liquid type, which can also be applied to the assay kit of the present invention. For example, R1 is composed mainly of a reagent composition for treating 1,5-AG assay-interference components such as glucose to eliminate their influence from the assay, as described above, while R2 is composed mainly of a reagent composition containing the 1,5-AG dehydrogenase of the present invention. For colorimetry, the reductive chromogenic agent can be incorporated as one of the reagent compositions of R1 and R2.

The diagnostic kit for POCT can also be constituted as a kit based on the same principles as above by further compactly encapsulating the components in a specific container or drying the reagent compositions.

The bedside or domestic kit for self-diagnosis can be composed of an assay chip comprising the redox mediator and the 1,5-AG dehydrogenase of the present invention incorporated as a main reagent composition, as with a self monitoring of blood glucose (SMBG) kit based on an electrochemical measurement method, as well as a puncture device (lancet) for blood collection, a measurement device, and so on.

Hereinafter, the present invention will be described specifically with reference to EXAMPLES. However, the present invention is not limited to these EXAMPLES.

In the present invention, the symbols in sequences represent the followings: a: adenine, g: guanine, c: cytosine and t: thymine. In the present specification, % means % by mass, unless otherwise specified.

EXAMPLE 1

Preparation of Transformant Containing Amplified/Expressed DNA Encoding Parent Strain-Derived 1,5-AG Dehydrogenase and Confirmation of High Expression of the DNA (A) Extraction of Total DNA from *Pseudomonas* sp. NK-85001

PUREGENE DNA Isolation Kit (manufactured by Gentra Systems, Inc.) was used in genomic DNA extraction from *Pseudomonas* sp. NK-85001. First, Pseudomonas sp. NK-85001 was inoculated into 2 mL of a nutrient medium consisting of 1% polypeptone, 0.2% yeast extracts and 0.1% magnesium sulfate heptahydrate (pH 7.0) and cultured overnight at 28° C. This culture solution was transferred to a 2-mL microtube and centrifuged at 10,000 rpm for 5 minutes. The supernatant was discarded, and the obtained pellet was suspended in 600 μL of Cell Lysis Solution included in the kit. Then, DNA was extracted according to the operation manual of the kit. The obtained DNA was dissolved in 100 μL of DNA Hydration Solution, heat-treated at 65° C. for 1 hour, and then stored at 4° C. or −20° C. The DNA concentration calculated from absorbance at 260 nm was 0.3 μg/μL.

(B) Selection of Primers

Based on the gene sequence of Agrobacterium tumefaciens NT1130 known as a microbe producing 1,5-AG dehydrogenase exhibiting the same effect as that of 1,5-AG dehydrogenase, homology search was carried out to select analogous enzymes of three strains: a *Rhizobium etli* CFN42 strain (Proc. Natl. Acad. Sci. U.S.A., 103 (10), 3834-3839 (2006)), a *Sinorhizobium meliloti* 1021 strain (Proc. Natl. Acad. Sci. U.S.A., 98 (17), 9877-9882 (2001)) and a *Brucella melitensis biovar Abortus* 2308 strain (Infect. Immun., 73 (12), 8353-8361 (2005)). Conservative regions of these 4 kinds of amino acid sequences were studied, and nucleotide sequences represented by SEQ ID NO: 7 or 8 were designed as primer sites based on an amino acid sequence represented by SEQ ID NO: 5 or 6 that seemed to be a common sequence.

(C) PCR Reaction

The primers represented by SEQ ID NO: 7 or 8 were used to perform PCR with the chromosomal DNA prepared in the paragraph (A) as a template. The PCR reaction was performed under the following conditions using a thermal cycler manufactured by PerkinElmer Inc. or Applied Biosystems, Inc. and LA-PCR Kit manufactured by TAMARA BIO INC.:

| Reaction solution: | 2× GC Buffer I: | 25 μL |
| --- | --- | --- |
| | dNTP Mixture (2.5 mM each): | 8 μL |
| | template DNA (0.3 μg/μL): | 0.5 μL |
| | primers (20 pmol/μL): | 0.5 μL each |
| | TaKaRa LA Taq (5 U/μL): | 0.5 μL |
| | distilled water: | 15 μL |
| PCR cycle: | denaturation: | 94° C. for 30 seconds |
| | annealing: | 50° C. for 30 seconds |
| | extension: | 72° C. for 90 seconds |

These steps were involved in one cycle, and a total of 30 cycles were performed.

As a result of electrophoresing the DNA fragment formed by this reaction on a 1% agarose gel for detection, a fragment of approximately 1400 bp could be confirmed.

(D) Sequencing of Amplified Fragment

The band of approximately 1400 bp of the paragraph (C) was excised from the gel, and DNA was purified using QIAquick Gel extraction kit (manufactured by QIAGEN). The DNA concentration calculated from absorbance at 260 nm was 22 ng/μL. As a result of sequencing this purified DNA, it was demonstrated that its nucleotide sequence corresponds to positions 19 to 1434 of a nucleotide sequence represented by SEQ ID NO: 3 and that an amino acid sequence corresponding thereto is a portion corresponding to positions 7 to 480 of an amino acid sequence represented by SEQ ID NO: 4. This sequencing was performed using ABI PRISM 3100-Avant Genetic Analyzer manufactured by Applied Biosystems, Inc.

(E) Genomic/Southern Hybridization

To 0.9 μg of the chromosomal DNA obtained in the paragraph (A), 40 units each of restriction enzymes EcoRI, KpnI, BamHI, HindIII, XbaI, SphI, PstI and NcoI were added and reacted at 37° C. for 21 hours for complete digestion. The digestion product was subjected to agarose gel electrophoresis. Then, the agarose gel was transferred to a nylon membrane (Hybond N+, manufactured by Amersham Biosciences Corp.). The partial fragment of the 1,5-AG dehydrogenase-encoding DNA obtained in the preceding paragraph was labeled with fluorescein using Gene Images random prime labeling module kit manufactured by Amersham Biosciences Corp. and used as a probe to perform southern hybridization. The detection was performed by chemiluminescence detection using CDP-Star Detection Module manufactured by Amersham Biosciences Corp, As a result, the probe strongly hybridized to a position of approximately 4 kb in the HindIII-treated fragment of the chromosomal DNA and to a position of approximately 5 kb in the NcoI-treated fragment thereof.

(F) Inverse PCR 0.9 μg of the HindIII fragment obtained in the paragraph (E) was dissolved in 16 μL of TE (10 mM Tris-HCl, 1 mM EDTA, pH 8.0) and reacted (self-ligated) at 16° C. for 60 minutes by the addition of 8 μL of Ligation high (manufactured by TOYOBO CO., LTD.) to obtain circular DNA. This circular DNA was used as a template to perform PCR using primers represented by SEQ ID NOs: 9 and 10. The primers were designed based on the nucleotide sequence of the DNA fragment determined in the paragraph (D). The PCR reaction was performed under the following conditions using a thermal cycler manufactured by Applied Biosystems, Inc.:

| Reaction solution: | 2X GC Buffer I: | 25 µL |
|---|---|---|
| | dNTP Mixture (2.5 mM each): | 8 µL |
| | template DNA (0.04 µg/µL): | 5 µL |
| | primers (20 pmol/µL): | 1 µL each |
| | TaKaRa LA Taq (5 U/µL): | 0.5 µL |
| | distilled water: | 9.5 µL |
| PCR cycle: | denaturation: | 96° C. for 20 seconds |
| | annealing: | 60° C. for 30 seconds |
| | extension: | 72° C. for 300 seconds |

These steps were involved in one cycle, and a total of 35 cycles were performed.

As a result of electrophoresing the DNA fragment formed by this reaction on a 1% agarose gel for detection, a fragment of approximately 3 kbp could be confirmed.

(G) Determination of Whole Nucleotide Sequence Encoding 1,5-AG Dehydrogenase

The DNA fragment obtained in the paragraph (F) was excised from the gel by the same procedures as in the paragraph (D) and purified using QIAquick Gel extraction kit (manufactured by QIAGEN). The DNA concentration calculated from absorbance at 260 nm was 90 ng/µL.

As a result of sequencing this purified DNA, it was demonstrated that the nucleotide sequence of the HindIII-treated DNA fragment containing the 1,5-AG dehydrogenase-encoding DNA is a nucleotide sequence represented by SEQ ID NO: 11 and that in this sequence, a gene sequence encoding the 1,5-AG dehydrogenase is a sequence corresponding to positions 201 to 1691 of the nucleotide sequence represented by SEQ ID NO: 11. It was also shown that the amino acid sequence of the 1,5-AG dehydrogenase is a polypeptide chain having a linkage of 497 amino acids in total length represented by SEQ ID NO: 11.

(H) Amplification of 1,5-AG Dehydrogenase-Encoding Gene

Primers were synthesized for amplifying the 1,5-AG dehydrogenase-encoding gene by PCR reaction from the *Pseudomonas* sp. NK-85001 chromosomal DNA obtained in the paragraph (A). Specifically, the N-terminal and C-terminal portion-encoding nucleotide sequence of the open reading frame of the 1,5-AG dehydrogenase gene elucidated in the paragraph (G) was used to synthesize a primer represented by SEQ ID NO: 12 adding the sequence of NcoI and EcoRI restriction sites as sequences of restriction sites to upstream of the N-terminus-encoding sequence and a primer represented by SEQ ID NO: 13 adding the sequence of a BamHI restriction site to downstream of the C-terminus-encoding sequence.

These DNA primers were used to amplify the 1,5-AG dehydrogenase gene under the following PCR conditions:

| Reaction solution: | 2X GC Buffer I: | 25 µL |
|---|---|---|
| | dNTP Mixture (2.5 mM each): | 8 µL |
| | template DNA (0.3 µg/µL): | 1 µL |
| | primers (20 pmol/µL): | 0.5 µL each |
| | TaKaRa LA Taq (5 U/µL): | 0.5 µL |
| | distilled water: | 14.5 µL |
| PCR cycle: | denaturation: | 94° C. for 40 seconds |
| | annealing: | 63° C. for 30 seconds |
| | extension: | 72° C. for 120 seconds |

These steps were involved in one cycle, and a total of 35 cycles were performed.

As a result of electrophoresing the DNA fragment formed by this reaction on a 1% agarose gel for detection, a fragment of approximately 1500 by could be confirmed.

(I) Preparation of Recombinant 1,5-AG Dehydrogenase Expression Vector

The 1,5-AG dehydrogenase-encoding gene obtained in the paragraph (H) was cleaved off with restriction enzymes EcoRI and BamHI and inserted to expression vectors pTrc99A (manufactured by Amersham Biosciences Corp.) to thereby cause expression. Specifically, the PCR solution containing the 1,5-AG dehydrogenase-encoding gene fragment amplified by PCR in the paragraph (H) was purified using QIAquick PCR purification kit (manufactured by QIAGEN) and subjected to cleavage reaction at 37° C. for 3 hours using 10 U each of restriction enzymes EcoRI and BamHI. The solution thus reacted was electrophoresed on a 1% agarose gel for separation. A band corresponding to approximately 1500 bp was excised from the gel, and DNA was purified using QIAquick Gel extraction kit (manufactured by QIAGEN).

Next, 1 µg of pTrc99A was left overnight at 37° C. using 10 U each of restriction enzymes EcoRI and BamHI to perform cleavage reaction of the restriction enzyme sites of the pTrc99A. The solution thus reacted was electrophoresed on a 1% agarose gel to confirm cleavage. The cleaved vector was purified using QIAquick PCR purification kit (manufactured by QIAGEN) and dissolved in 50 µL of a Tris-HCl buffer (10 mM, pH 8.5).

8 µL of the solution containing the 1,5-AG dehydrogenase-encoding gene fragment of approximately 1500 bp obtained by cleavage with restriction enzymes EcoRI and BamHI and 8 µL of the solution of the pTrc99A obtained by cleavage with EcoRI and BamHI were mixed with Ligation high to perform ligation reaction at 16° C. for 30 minutes. 2 µL of the solution thus reacted was used to transform *E. coli* JM109.

The solution containing the transformed *E. coli* JM109 was applied onto an LB agar medium containing 100 µg/mL ampicillin, 0.1 mM IPTG (isopropyl-β-thiogalactopyranoside) and 0.004% X-gal and cultured overnight at 37° C. for colony formation. Each positive white colony was selected, inoculated to 3 mL of an LB liquid medium containing 100 µg/mL ampicillin, and cultured overnight at 37° C. The microbial cells were collected by the centrifugation of the culture solution. Then, approximately 2 µg of plasmid DNA was purified using QIAquick plasmid purification kit (manufactured by QIAGEN). Approximately 0.5 µg aliquot of this plasmid DNA was cleaved with EcoRI and BamHI and electrophoresed on a 1% agarose gel to thereby confirm the presence of the insert fragment corresponding to approximately 1500 bp. Furthermore, as a result of confirming the nucleotide sequence of the insert fragment by sequencing reaction, no variation was observed. This expression plasmid was designated as pTrc-PS15DH. A recombinant 1,5-AG dehydrogenase (SEQ ID NO: 4) translated with this expression plasmid differs in N-terminal sequence from the amino acid sequence of the original 1,5-AG dehydrogenase represented by SEQ ID NO: 11. Specifically, the amino acid sequence of the original 1,5-AG dehydrogenase has Val-Thr-Ala-Leu- in its N-terminus, whereas the amino acid sequence of the recombinant 1,5-AG dehydrogenase has Met-Glu-Phe- at its N-terminus.

(J) Expression of Recombinant 1,5-AG Dehydrogenase in *E. Coli* and Activity Determination The *E. coli* JM109 strains transformed with the pTrc-PS15DH vectors confirmed in the paragraph (I) to have the insert fragment were inoculated to 3 mL of an LB medium containing 100 µg/mL ampicillin and cultured at 28° C. for 14 hours. Of this culture solution, a 0.2 mL aliquot was inoculated to 10 mL of an LB medium (containing 100 μg/mL ampicillin). Approximately 3 hours later, the rise of OD600 of the culture solution to 0.4 to 0.7 was confirmed, and 1,5-AG dehydrogenase expression in *E. coli* was then induced by the addition of 0.1 M IPTG (final concentration: 0.1 mM) to the medium. This culture solution was further cultured overnight at 28° C. and centrifuged at 10000×g for 5 minutes to precipitate cells. The supernatant was removed, and the pellet was then washed twice with a 0.85% aqueous NaCl solution. Cells were precipitated by centrifugation. Then, the microbial cells were suspended in 1 mL of a 50 mM sodium phosphate buffer, pH 7.5. Triton X-100 was added thereto at a concentration of 0.25%, and the microbial cells were disrupted using a bead impact-type cell disrupter MINI-BEAD BEATER (30 seconds×4, manufactured by Central Scientific Commerce, Inc.) while cooled in ice. After centrifugation at 20000×g for 10 minutes, the supernatant was examined as a crude enzyme solution for its 1,5-AG dehydrogenase activity. The composition of the reaction solution is as described below. Since the 1,5-AG dehydrogenase also reacts with L-sorbose as its substrate, L-sorbose was used for convenience instead of 1,5-AG in the enzymatic activity determination.

Composition of Reaction Solution:

| | |
|---|---|
| 0.1M potassium phosphate buffer, pH 7.0 | 200 μL |
| 1M L-sorbose | 200 μL |
| 3 mM DCIP (2,6-dichlorophenolindophenol) (manufactured by Merck & Co., Inc.) | 28 μL |
| 3 mM 1-m-PMS (manufactured by DOJINDO LABORATORIES) | 40 μL |
| distilled water | 122 μL |
| crude enzyme solution | 10 μL |

The components other than the crude enzyme solution are mixed and kept at 37° C. for 10 minutes. Then, the crude enzyme solution is added to the reaction solution to initiate reaction. Decrease in absorbance at 600 nm for 1 minute with the temperature kept at 37° C. is determined.

The enzymatic activity can be determined according to the following equation:

Enzymatic activity (U/mL)=(Δ600/min×0.6 (mL)× dilution ratio of crude enzyme solution)/(16.3× 0.01 (mL)).

The activity of the crude enzyme solution was 4.4 U/mL.

EXAMPLE 2

Obtainment of Thermostable 1,5-AG Dehydrogenase

The 1,5-AG dehydrogenase obtained in EXAMPLE 1 was designated as Ver. 0. Variations were introduced thereto as shown in FIG. 1 to obtain thermostable 1,5-AG dehydrogenases (Ver. 1.0 to Ver. 12.0).

[1] Obtainment of Thermostable 1,5-AG Dehydrogenase by Random Mutagenesis

Figure 2:
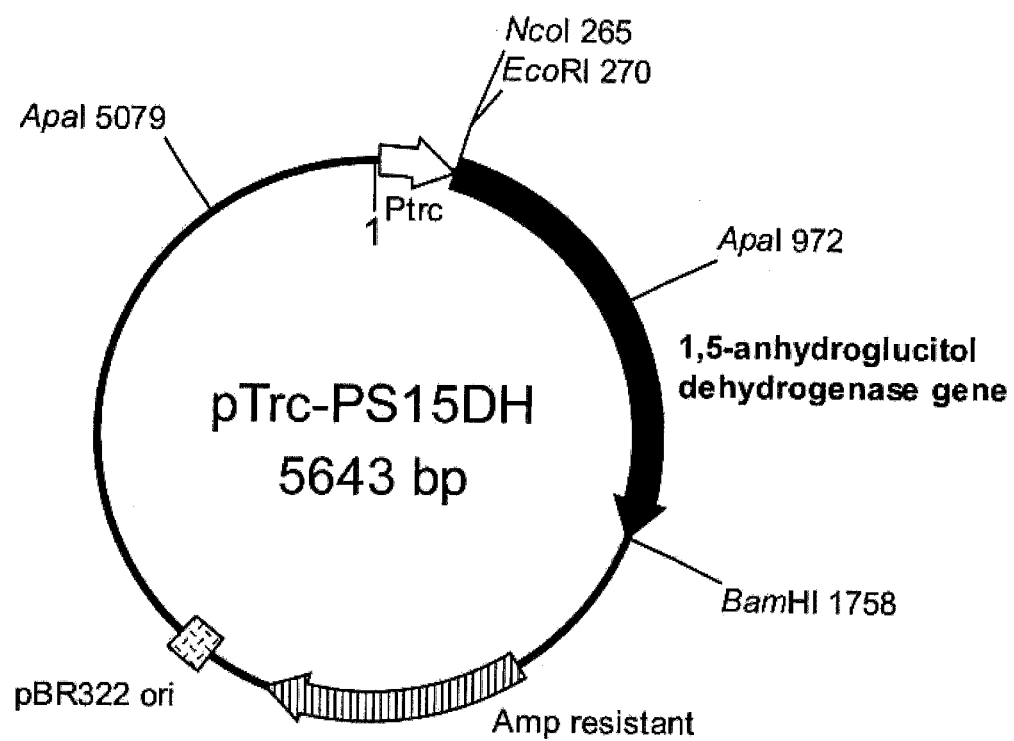
FIG. 2 is a diagram showing a plasmid pTrc-PS15DH constructed in EXAMPLE 1. A 1,5-AG dehydrogenase gene shown in this plasmid encodes the 1,5-AG dehydrogenase Ver. 0. When the 1,5-AG dehydrogenase gene in the plasmid encodes any of 1,5-AG dehydrogenases Ver. 1.0 to Ver. 12.0, these plasmids are referred to as pTrc-PS15DH (Ver. 1.0) to pTrc-PS15DH (Ver. 12.0), respectively.
Figures 1, 3:
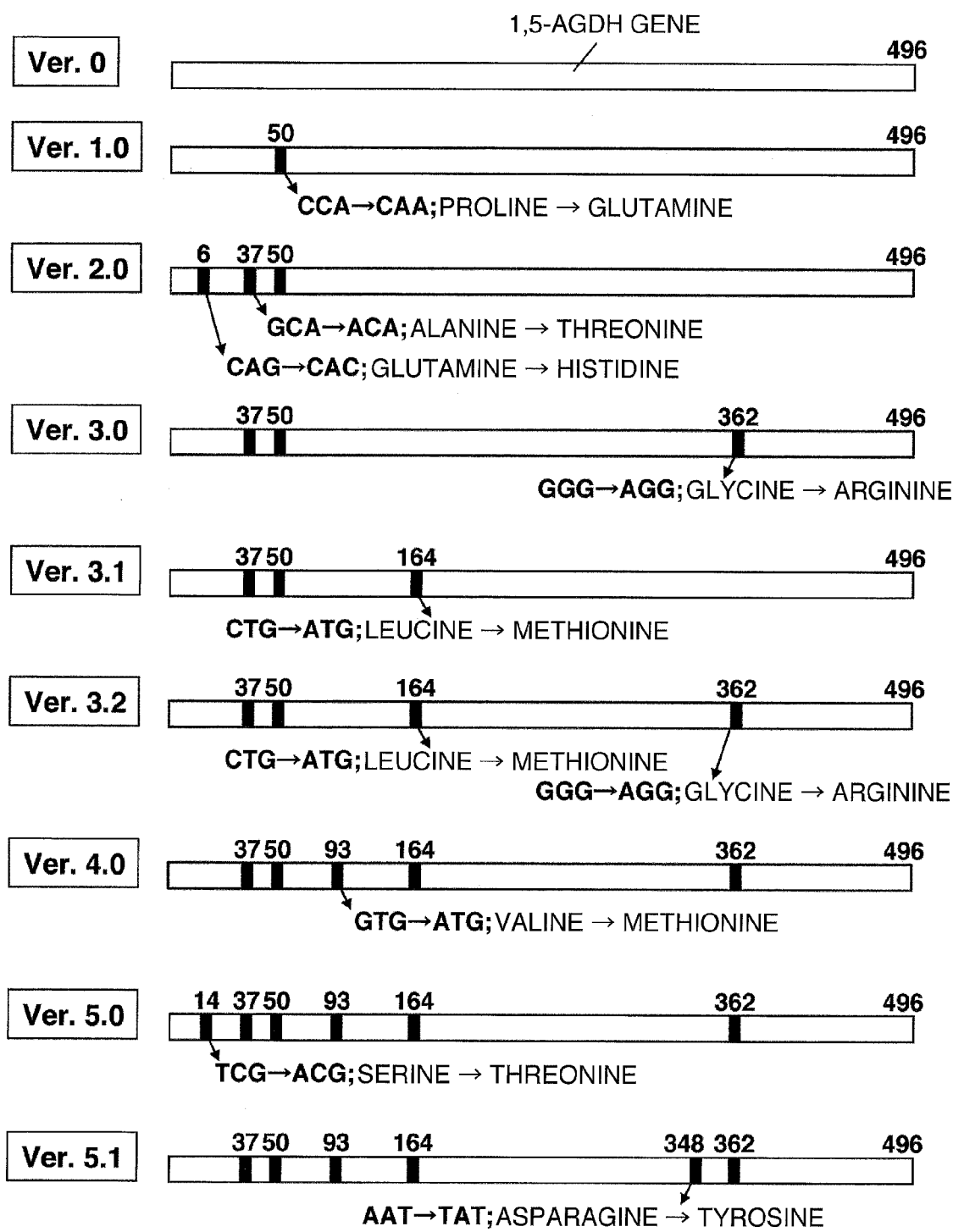
Figures 2, 3:
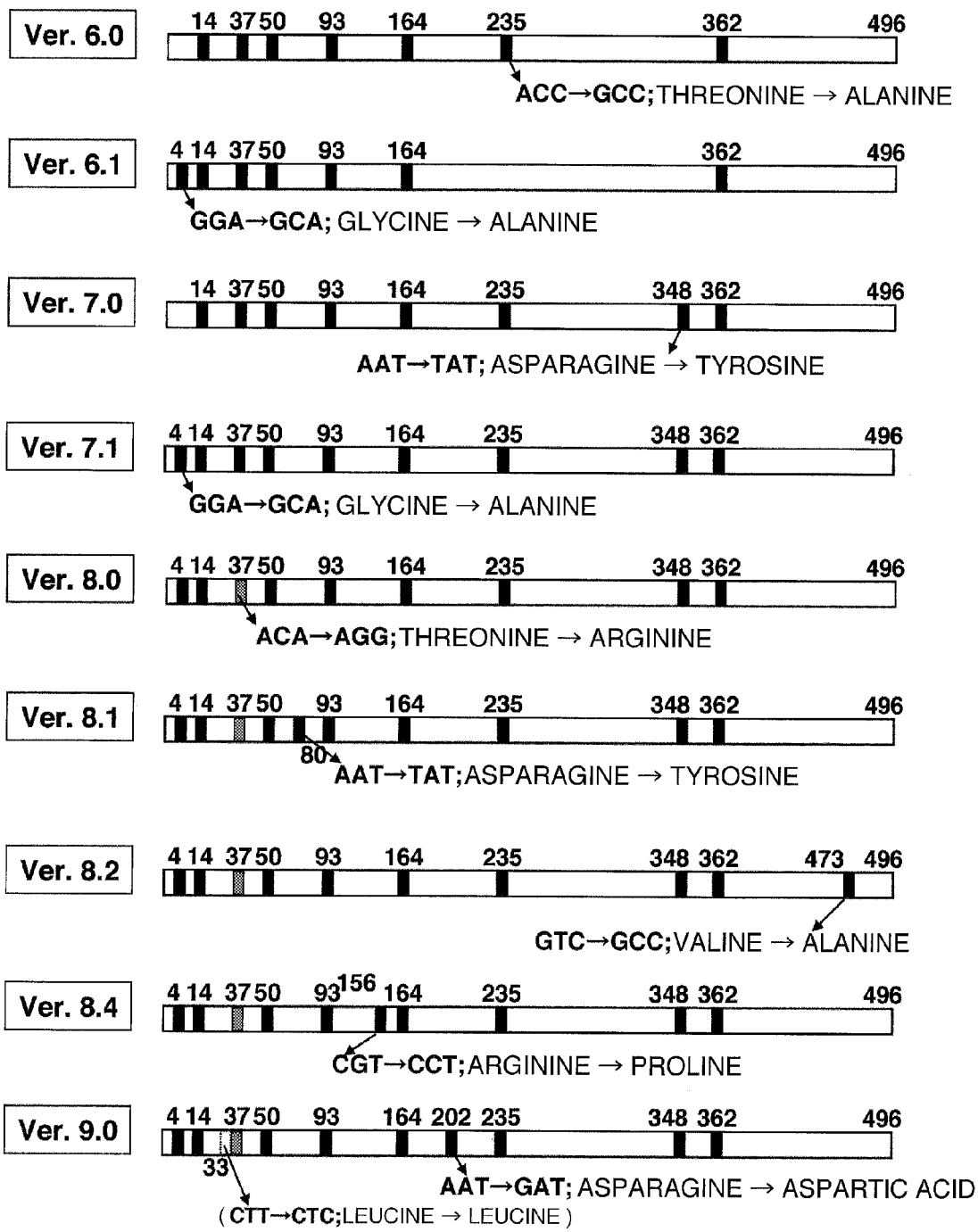
Figure 3:
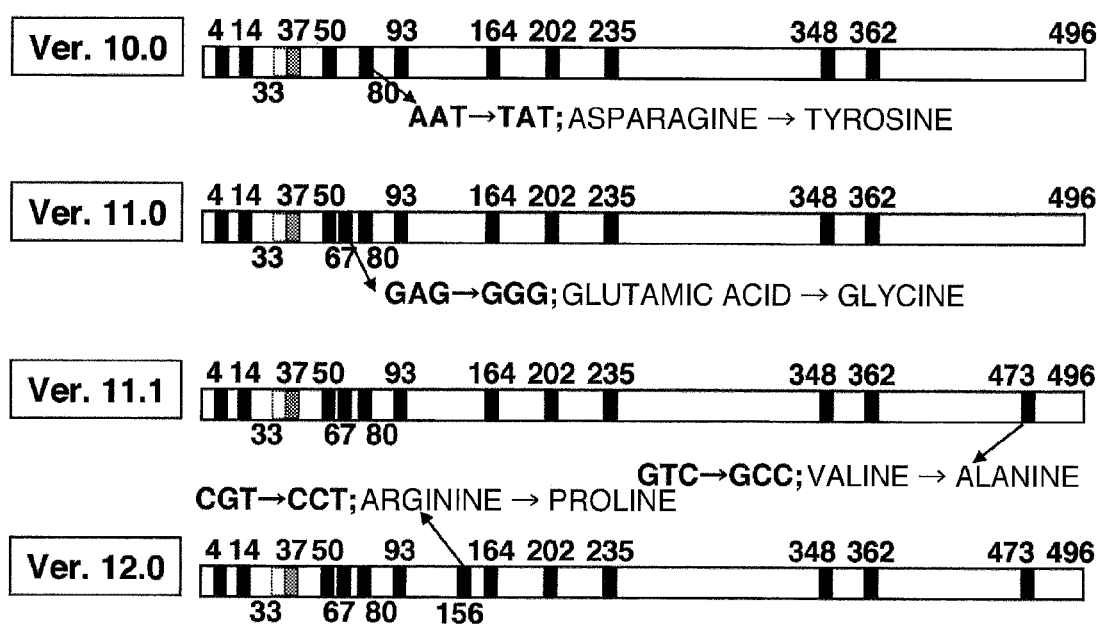

Thermostability improvement steps are shown in FIGS. 1, 3-1, 3-2 and 3-3. When enzymes having improved thermostability were prepared from the 1,5-AG dehydrogenase Ver. 0 to Ver. 1.0, from Ver. 1.0 to Ver. 2.0, from Ver. 2.0 to Ver. 3,0 and Ver. 3.1, from Ver. 4.0 to Ver. 5.0 and Ver. 5.1, from Ver. 5.0 to Ver. 6.0 and Ver. 6,1, from Ver. 7,1 to Ver. 8.1, Ver. 8.2 and Ver. 8.4, from Ver. 8.0 to Ver. 9.0 and from Ver. 10.0 to Ver. 11.0, these enzymes were obtained by: preparing a variation library prepared by random mutagenesis from a gene encoding the enzyme of each version; expressing these enzyme genes; and screening, from among the expressed enzymes, those having improved thermostability.

For example, the obtainment of Ver. 1.0 from the 1,5-AG dehydrogenase Ver. 0 was performed as follows: first, variations were randomly introduced according to the protocol of GeneMorph II Random Mutagenesis Kit (manufactured by Stratagene Corp.) using the pTrc-PS15DH prepared in EXAMPLE 1 to construct a point variant gene library. Mutazyme II DNA polymerase included in this kit can introduce variations with much higher frequency than that of conventional Taq DNA polymerase and can further control the frequency of the introduced variations by controlling initial vector concentrations. Thus, the introduced variations were controlled by performing PCR with the pTrc-PS15DH as a template. This PCR reaction was performed using, as primers, a 5' primer (SEQ ID NO: 12) adding the sequences of NcoI and EcoRI restriction sites to upstream of the N-terminus-encoding sequence and a 3' primer (SEQ ID NO: 13) adding the sequence of a BamHI restriction site to downstream of the C-terminus-encoding sequence, as in cloning. The variation PCR conditions are as follows:

Variation PCR conditions: water was added to a mixture of 2.3 μg of template DNA, 2.5 units of Mutazyme II DNA polymerase, a reaction buffer (1×) included in the GeneMorph II Random Mutagenesis Kit, 0.2 mM dNTP, 320 pmol/mL 5' primer (SEQ ID NO: 12) and 320 pmol/mL 3' primer (SEQ ID NO: 13) to prepare a solution of 50 μL in total, which was then heat-treated at 96° C. for 3 minutes, then amplified using a 30-cycle program involving 96° C. for 1 minute, 63° C. for 1 minute and 72° C. for 100 seconds, and then treated at 72° C. for 10 minutes. As a result of electrophoresing 5 μL of the amplification reaction solution on a 1% agarose gel, it was confirmed that the 1,5-AG dehydrogenase-encoding DNA fragment of approximately 1500 bp of interest was amplified.

Next, the variation PCR product amplified by random mutagenesis was introduced into *E. coli* JM109 to construct a variant gene library. Specifically, the PCR solution containing the gene encoding the variant 1,5-AG dehydrogenase was electrophoresed on a 1% agarose gel for separation. A band corresponding to approximately 1500 bp was excised from the gel, and DNA in the band portion was purified using QIAquick Gel Extraction Kit (manufactured by QIAGEN) and subjected to cleavage reaction overnight at 37° C. using 20 units each of restriction enzymes NcoI and BamHI. Then, the DNA was extracted using phenol/chloroform, subsequently precipitated using ethanol, and then dissolved in 12 μL of a TE buffer. 2 μL of the DNA solution containing the purified NcoI/BamHI-cleaved DNA portion corresponding to approximately 1500 bp and 1 μL of a vector pTrc99A cleaved with NcoI and BamHI were mixed with 2 μL of Ligation High (manufactured by TOYOBO CO., LTD.) to perform ligation reaction at 16° C. for approximately 30 minutes. 1.5 μL of the ligation reaction solution was used in *E. coli* JM109 transformation to prepare a variant gene library.

Approximately 10100 colonies of the variant gene library were randomly picked up using a colony picker (PM-2s, manufactured by Microtec Co., Ltd.) and subjected to primary screening In the primary screening, a 1.2-mL 96-well square deep well plate (manufactured by NALGE NUNC INTERNATIONAL MK.) was used. The colonies were transplanted to 500 μL of an LB liquid medium containing 50 μg/mL ampicillin and cultured (28° C., 900 rpm) overnight in a 96-well square plate shaker (TITRAMAX 100, manufactured by HEIDOLPH). The 96-well square deep well plate was centrifuged at 2000 rpm for 10 minutes to separate microbial cells, which were then treated at −80° C. for 1 hour. The microbial cells were thawed and then treated at 60° C. for 20 minutes. Active variant enzymes were picked up by suspending the microbial cells thus treated at 60° C. by the addition of 200 μL of a 0.1 M potassium phosphate buffer (pH 7.0) containing 0.5% Triton X-100, 30 μL of 6 mM 2,6-dichlorophenolindophenol (DCIP) and 5 μL of 50 mg/mL 1,5-AG. The blue color of DCIP is decolorized for colonies having the enzymatic activity. As a result, it was observed that the blue color of DCIP was decolorized for colonies carrying a 1,5-AG dehydrogenase Ver. 1.0 having improved thermostability compared with the 1,5-AG dehydrogenase Ver. 0.

The obtainment of Ver. 2.0 from the 1,5-AG dehydrogenase Ver. 1.0, Ver. 3.0 and Ver. 3.1 from Ver. 2.0, Ver. 5,0 and Ver. 5.1 from Ver. 4.0, Ver. 6.0 and Ver. 6.1 from Ver. 5.0, Ver. 8.1 and Vet 8.2 and Ver. 8.4 from Ver. 7.1, Ver. 9.0 from Ver. 8.0 and Ver. 11.0 from Ver. 10.0 was also performed in the same way as above.

When Ver. 2.0 was obtained from the 1,5-AG dehydrogenase Ver. 1.0, pTrc-PS15DH (Ver. 1.0) was used as a template in variation PCR; when Ver. 3.0 and Ver. 3.1 were obtained from the 1,5-AG dehydrogenase Ver. 2.0, pTrc-PS15DH (Ver. 2.0) was used as a template in variation PCR; when Ver. 5.0 and Ver. 5.1 were obtained from the 1,5-AG dehydrogenase Ver. 4.0, pTrc-PS15DH (Ver. 4.0) was used as a template in variation PCR; when Ver. 6.0 and Ver. 6.1 were obtained from the 1,5-AG dehydrogenase Ver. 5.0, pTre-PS15DH (Ver. 5.0) was used as a template in variation PCR; when Ver. 8.1, Ver. 8.2 and Ver. 8.4 were obtained from the 1,5-AG dehydrogenase Ver. 7.1, pTrc-PS15DH (Ver. 7.1) was used as a template in variation PCR; when Ver. 9.0 was obtained from the 1,5-AG dehydrogenase Ver. 8.0, pTrc-PS15DH (Ver. 8.0) was used as a template in variation PCR; and when Ver. 11.0 was obtained from the 1,5-AG dehydrogenase Ver. 10.0, pTrc-PS15DH (Ver. 10.0) was used as a template in variation PCR.

Moreover, when Ver. 2.0 was obtained from the 1,5-AG dehydrogenase Ver. 1.0, approximately 3700 colonies randomly picked up for screening were cultured in a 96-well square deep well plate, and the microbial cells were frozen, thawed, and then treated at 60° C. for 21 minutes.

When Ver. 3.0 and Ver. 3.1 were obtained from the 1,5-AG dehydrogenase Ver. 2.0, approximately 12200 colonies randomly picked up for screening were cultured in a 96-well square deep well plate, and the microbial cells were frozen, thawed, and then treated at 60° C. for 22 minutes.

When Ver. 5.0 and Ver, 5.1 were obtained from the 1,5-AG dehydrogenase Ver. 4.0, approximately 22000 colonies randomly picked up for screening were cultured in a 96-well square deep well plate, and the microbial cells were frozen, thawed, and then treated at 60° C. for 23 minutes.

When Ver. 6.0 and Ver. 6.1 were obtained from the 1,5-AG dehydrogenase Ver. 5.0, approximately 3600 colonies randomly picked up for screening were cultured in a 96-well square deep well plate, and the microbial cells were frozen, thawed, and then treated at 60° C. for 24 minutes.

When Ver. 8.1, Ver. 8.2 and Ver. 8.4 were obtained from the 1,5-AG dehydrogenase Ver. 7.1, approximately 15000 colonies randomly picked up for screening were cultured in a 96-well square deep well plate, and the microbial cells were frozen, thawed, and then treated at 60° C. for 28 minutes.

When Ver. 9.0 was obtained from the 1,5-AG dehydrogenase Ver. 8.0, approximately 700 colonies randomly picked up for screening were cultured in a 96-well square deep well plate, and the microbial cells were frozen, thawed, and then treated at 60° C. for 38 minutes.

When Ver. 11.0 was obtained from the 1,5-AG dehydrogenase Ver. 10.0, approximately 200 colonies randomly picked up for screening were cultured in a 96-well square deep well plate, and the microbial cells were frozen, thawed, and then treated at 60° C. for 45 minutes.

[2] Obtainment of Thermostable 1,5-AG Dehydrogenase by Site-Directed Mutagenesis In FIGS. 1, 3-1, 3-2 and 3-3, site-directed mutagenesis was used in the preparation of Ver. 4.0 from Ver. 3.2, Ver. 8.0 from Ver. 7.1, Ver. 10.0 from Ver. 9.0 and Ver. 12.0 from Ver. 11.1.

For example, the obtainment of Ver. 4.0 from the 1,5-AG dehydrogenase Ver. 3.2 was performed as follows: first, the pTrc-PS15DH (Ver. 3.2) prepared in EXAMPLE 1 was used as a template to perform PCR. This PCR reaction was performed using, as primers, a 5' primer (SEQ ID NO: 14) designed based on the upstream region of the 1,5-AG dehydrogenase gene in the pTrc-PS15DH (Ver. 3.2) and a 3' primer (SEQ ID NO: 15) designed to delete the BamHI site of the pTrc-PS15DH (Ver. 3.2) and using, aside from them, a 5' primer (SEQ ID NO: 16) designed to substitute methionine for valine as an amino acid residue at position 93 of the 1,5-AG dehydrogenase and a 3' primer (SEQ ID NO: 17) designed based on the downstream region of the 1,5-AG dehydrogenase gene in the pTrc-PS15DH (Ver. 3.2). The PCR conditions are as follows:

PCR conditions: water was added to a mixture of 0.02 ng of template DNA, 2.5 units of LA Taq, EX Taq buffer (1×), 0.25 mM dNTP, 64 pmol/mL 5' primer (SEQ ID NO: 14) and 64 pmol/mL 3' primer (SEQ ID NO: 15) or 64 pmol/mL 5' primer (SEQ ID NO: 16) and 64 pmol/mL 3' primer (SEQ ID NO: 17) to prepare a solution of 50 μL in total, which was then heat-treated at 94° C. for 5 minutes, then amplified using a 25-cycle program involving 94° C. for 30 seconds, 55° C. for 2 minutes and 72° C. for 100 seconds, and then treated at 72° C. for 5 minutes.

After the amplification reaction, each PCR product was purified using QIAquick PCR Purification Kit (manufactured by QIAGEN). Water was added to a mixture of 0.5 μL each solution of this PCR product, EX Taq buffer (1×) and 0.25 mM dNTP to prepare a solution of 47.5 μL in total, which was then heat-treated at 94° C. for 10 minutes, then cooled to 37° C. over 60 minutes, and treated at 37° C. for 15 minutes. Then, 2.5 units of LA Taq were added thereto, and the mixture was treated at 72° C. for 3 minutes. Then, 64 pmol/mL 5' primer (SEQ ID NO: 14) and 64 pmol/mL 3' primer (SEQ ID NO: 17) were added thereto, and the mixture was heat-treated at 94° C. for 5 minutes, then amplified using a 10-cycle program involving 94° C. for 30 seconds, 55° C. for 2 minutes and 72° C. for 100 seconds, and then treated at 72° C. for 5 minutes. As a result of electrophoresing 5 μL of the amplification reaction solution on a 1% agarose gel, it was confirmed that the 1,5-AG dehydrogenase-encoding DNA fragment of approximately 1500 bp of interest was amplified.

The PCR solution containing the amplified gene encoding the variant 1,5-AG dehydrogenase was electrophoresed on a 1% agarose gel for separation. A band corresponding to approximately 1500 bp was excised from the gel, and DNA in the band portion was purified using QIAquick Gel Extraction Kit (manufactured by QIAGEN) and subjected to cleavage reaction overnight at 37° C. using 20 U each of restriction enzymes NcoI and BamHI. Then, the DNA was extracted using phenol/chloroform, subsequently precipitated using ethanol, and then dissolved in 12 mL of a TE buffer. 2 mL of the DNA solution containing the purified NcoI/BamHI-cleaved DNA portion corresponding to approximately 1500 bp and 1 mL of a vector pTrc99A cleaved with NcoI and BamHI were mixed with 2 mL of Ligation High (manufactured by TOYOBO CO., LTD.) to perform ligation reaction at 16° C. for approximately 30 minutes. 1.5 mL of the ligation reaction solution was used in E. coli JM109 transformation to obtain E. coli JM109 containing a gene encoding a 1,5-AG dehydrogenase Ver. 4.0 having improved thermostability compared with the 1,5-AG dehydrogenase Ver. 3.2.

The preparation of Ver. 8.0 from the 1,5-AG dehydrogenase Ver. 7.1, Ver. 10.0 from Ver. 9.0 and Ver. 12.0 from Ver. 11.1 was also performed in the same way as above.

When Ver. 8.0 was obtained from the 1,5-AG dehydrogenase Ver. 7.1, PCR was performed using pTre-PS15DH (Ver. 7.1) as a template and using, as primers, the 5' primer (SEQ ID NO: 14) and the 3' primer (SEQ ID NO: 15) and using, aside from them, a 5' primer (SEQ ID NO: 18) designed to substitute another amino acid residue for threonine as an amino acid residue at position 37 of the 1,5-AG dehydrogenase and the 3' primer (SEQ ID NO: 17). As a result, E. coli JM109 was obtained which contained a gene encoding a 1,5-AG dehydrogenase Ver. 8.0 having arginine substituted for threonine as an amino acid residue at position 37 of the 1,5-AG dehydrogenase Ver. 7.1.

When Ver. 10.0 was obtained from the 1,5-AG dehydrogenase Ver. 9.0, PCR was performed using pTrc-PS15DH (Ver. 9.0) as a template and using, as primers, the 5' primer (SEQ ID NO: 14) and the 3' primer (SEQ ID NO: 15) and using, aside from them, a 5' primer (SEQ ID NO: 19) designed to substitute tyrosine for asparagine as an amino acid residue at position 80 of the 1,5-AG dehydrogenase and the 3' primer (SEQ ID NO: 17).

When Ver. 12.0 was obtained from the 1,5-AG dehydrogenase Ver. 11.1, PCR was performed using pTrc-PS15DH (Ver. 11.1) as a template and using, as primers, the 5' primer (SEQ ID NO: 14) and the 3' primer (SEQ ID NO: 15) and using, aside from them, a 5' primer (SEQ ID NO: 20) designed to substitute proline for arginine as an amino acid residue at position 156 of the 1,5-AG dehydrogenase and the 3' primer (SEQ ID NO: 17).

[3] Obtainment of Thermostable 1,5-AG Dehydrogenase by Ligation of Two Plasmid DNAs In FIGS. 1, 3-1, 3-2 and 3-3, the method of ligation of two plasmid DNAs was used in the preparation of Ver. 3.2 from Ver. 3.0 and Ver. 3.1, Ver. 7.0 from Ver. 5.1 and Ver. 6.0 and Ver. 11.1 from Ver. 8,2 and Ver. 11.0.

When Ver. 3.2 was obtained from Ver. 3.0 and Ver. 3.1, pTrc-PS15DH (Ver. 3.0) and pTrc-PS15DH (Ver. 3.1) were separately subjected to cleavage reaction at 37° C. using 45 U of a restriction enzyme ApaI and then electrophoresed on a 1% agarose gel for separation. A band corresponding to approximately 4100 bp cleaved from the pTrc-PS15DH (Ver. 3.0) and a band corresponding to approximately 1500 bp from the pTrc-PS15DH (Ver. 3.1) were excised from the gel, and DNA in the band portions was purified using QIAquick Gel Extraction Kit (manufactured by QIAGEN). The DNA in the band portion corresponding to approximately 4100 bp cleaved from the pTrc-PS15DH (Ver. 3.0) was subjected to dephosphorylation treatment with calf small intestine-derived alkaline phosphatase. Then, the DNA was extracted using phenol/chloroform, subsequently precipitated using ethanol, and then dissolved in 12 mL of a TE buffer. 1 mL of the DNA solution containing this ApaI-cleaved pTrc-PS15DH (Ver. 3.0) DNA portion corresponding to approximately 4100 bp and 2 mL of the DNA solution containing the ApaI-cleaved pTrc-PS15DH (Ver. 3.1) DNA portion corresponding to approximately 1500 bp were mixed with 2 mL of Ligation High (manufactured by TOYOBO CO., LTD.) to perform ligation reaction at 16° C. for approximately 30 minutes. 1.5 mL of the ligation reaction solution was used in E. coli JM109 transformation to obtain E. coli JM109 containing a gene encoding a 1,5-AG dehydrogenase Ver. 3.2 having improved thermostability compared with the 1,5-AG dehydrogenases Ver. 3.0 and Ver. 3.1.

The preparation of Ver. 7.0 from the 1,5-AG dehydrogenases Ver. 5.1 and Ver. 6.0 and Ver. 11.1 from Ver. 8.2 and Ver. 11.0 was also performed in the same way as above. For Ver. 7.0, a DNA portion corresponding to approximately 4100 bp from pTrc-PS15DH (Ver. 5.1) and a DNA portion corresponding to approximately 1500 bp from pTrc-PS15DH (Ver. 6.0) were used. For Ver. 11.0, a DNA portion corresponding to approximately 4100 bp from pTrc-PS15DH (Ver. 8.2) and a DNA portion corresponding to approximately 1500 bp from pTrc-PS15DH (Ver. 11.0) were used.

[4] Obtainment of Thermostable 1,5-AG Dehydrogenase by PCR

In FIGS. 1, 3-1, 3-2 and 3-3, PCR was used in the preparation of Ver. 7.1 from the 1,5-AG dehydrogenases Ver. 6.1 and Ver. 7.0.

PCR was performed using pTrc-PS15DH (Ver. 7.0) as a template and using, as primers, a 5' primer (SEQ ID NO: 20) designed to add the sequence of NcoI and EcoRI restriction sites to upstream of the N-terminus-encoding sequence and further substitute alanine for glycine as an amino acid residue at position 4 of the 1,5-AG dehydrogenase and a 3' primer (SEQ ID NO: 13) adding the sequence of a BamHI restriction site to downstream of the C-terminus-encoding sequence. The PCR conditions are as follows:

PCR conditions: water was added to a mixture of 1.25 ng of template DNA, 1.5 units of EX Tag, EX Tag buffer (1×), 0.2 mM dNTP, 384 pmol/mL 5' primer (SEQ ID NO: 21) and 384 pmol/mL 3' primer (SEQ ID NO: 13) to prepare a solution of 50 mL in total, which was then heat-treated at 96° C. for 5 minutes, then amplified using a 30-cycle program involving 96° C. for 1 minute, 63° C. for 1 minute and 72° C. for 100 seconds, and then treated at 72° C. for 5 minutes. As a result of electrophoresing 5 mL of the amplification reaction solution on a 1% agarose gel, it was confirmed that the 1,5-AG dehydrogenase-encoding DNA fragment of approximately 1500 bp of interest was amplified.

The PCR solution thus amplified was electrophoresed on a 1% agarose gel for separation. A band corresponding to approximately 1500 bp was excised from the gel, and DNA in the band portion was purified using QIAquick Gel Extraction Kit (manufactured by QIAGEN) and subjected to cleavage reaction overnight at 37° C. using 20 U each of restriction enzymes NcoI and BamHI. Then, the DNA was extracted using phenol/chloroform, subsequently precipitated using ethanol, and then dissolved in 12 mL of a TE buffer. 2 mL of the DNA solution containing the purified NcoI/BamHI-cleaved DNA portion corresponding to approximately 1500bp and 1 mL of a vector pTrc99A cleaved with NcoI and BamHI were mixed with 2 mL of Ligation High (manufactured by TOYOBO CO., LTD.) to perform ligation reaction at 16° C. for approximately 30 minutes. 1.5 mL of the ligation reaction solution was used in E. coli JM109 transformation to obtain E. coli JM109 containing a gene encoding a 1,5-AG dehydrogenase Ver. 7.1.

EXAMPLE 3

Stability of Thermostable 1,5-AG Dehydrogenase at Heat Treatment Temperature and Confirmation of Variations by Nucleotide Sequence Analysis The *E. coli* JM109 containing the gene encoding each thermostable 1,5-AG dehydrogenase obtained in the paragraphs [1] to [4] of EXAMPLE 2 was transplanted to 10 mL of an LB liquid medium containing 50 μg/mL ampicillin and 0.1 mM IPTG and shake-cultured at 30° C. for 16 hours. 10 mL of the shake-culture solution was centrifuged at 10000 rpm for 5 minutes. The culture supernatant was removed, and the pellet was then washed twice with a 0.85% aqueous NaCl solution. These microbial cells were suspended in 1 mL of a 50 mM sodium phosphate buffer (pH 7.5) containing 0.25% Triton X-100. The microbial cells were disrupted using a bead impact-type cell disrupter MINI-BEAD BEATER (30 seconds×4, manufactured by Central Scientific Commerce, Inc.) while cooled in ice. After centrifugation at 15000 rpm for 10 minutes, the supernatant was used as a crude enzyme solution. When the crude enzyme solution was heat-treated, the treatment was performed for 10 minutes in a water bath of 45° C., 50° C., 55° C. or 60° C.

The enzymatic activity of the 1,5-AG dehydrogenase was calculated by measurement by the same approach as that described in the paragraph (J) of EXAMPLE 1.

A specific activity that represents the enzymatic activity of the 1,5-AG dehydrogenase per mg of the crude enzyme solution was calculated according to the following equation:

Specific activity (U/mg)=enzymatic activity (U/mL)/protein concentration of crude enzyme solution (mg/mL). Moreover, the rate of residual activity was calculated according to the following equation:

Rate of residual activity (%)=(specific activity of crude enzyme solution after heat treatment/specific activity of crude enzyme solution before heat treatment)×100.

The specific activity of each thermostable 1,5-AG dehydrogenase and the rate of residual activity after 10-minute treatment at each temperature are shown in Table 1.

TABLE 1

|  | Ver. 0 | Ver. 1.0 | Ver. 2.0 | Ver. 3.0 | Ver. 3.1 | Ver. 3.2 |
|---|---|---|---|---|---|---|
| Specific activity (U/mg) | 1.2 | 1.7 | 1.4 | 2.8 | 1.2 | 2.0 |
| Rate of residual activity after 10-minute treatment at 45° C. (%) | 3.0 | 8.3 | 31.0 | 40.0 | 54.0 | 68.0 |
| Rate of residual activity after 10-minute treatment at 50° C. (%) | — | — | — | — | — | 14.0 |
| Rate of residual activity after 10-minute treatment at 55° C. (%) | — | — | — | — | — | — |

|  | Ver. 4.0 | Ver. 5.0 | Ver. 5.1 | Ver. 6.0 | Ver. 6.1 | Ver. 7.0 |
|---|---|---|---|---|---|---|
| Specific activity (U/mg) | 2.9 | 1.6 | 2.6 | 2.2 | 3.6 | 1.9 |
| Rate of residual activity after 10-minute treatment at 45° C. (%) | 73.0 | 77.0 | 84.0 | 76.0 | 67.0 | 78.0 |
| Rate of residual activity after 10-minute treatment at 50° C. (%) | 18.0 | 35.0 | 37.0 | 40.0 | 37.0 | 63.0 |
| Rate of residual activity after 10-minute treatment at 55° C. (%) | — | — | — | — | — | — |

|  | Ver. 7.1 | Ver. 8.0 | Ver. 8.1 | Ver. 9.0 |
|---|---|---|---|---|
| Specific activity (U/mg) | 2.8 | 4.0 | 2.0 | 3.0 |
| Rate of residual activity after 10-minute treatment at 45° C. (%) | 89.0 | 91.0 | 89.0 | 98.0 |
| Rate of residual activity after 10-minute treatment at 50° C. (%) | 61.0 | 81.0 | 84.0 | 90.0 |
| Rate of residual activity after 10-minute treatment at 55° C. (%) | 10.0 | 34.0 | 74.0 | 64.0 |
| Rate of residual activity after 10-minute treatment at 60° C. (%) | — | — | — | — |

|  | Ver. 10.0 | Ver. 11.0 | Ver. 11.1 | Ver. 12.0 |
|---|---|---|---|---|
| Specific activity (U/mg) | 1.7 | 3.4 | 0.8 | 1.2 |
| Rate of residual activity after 10-minute treatment at 45° C. (%) | 97.0 | 97.0 | — | — |
| Rate of residual activity after 10-minute treatment at 50° C. (%) | 91.0 | 97.0 | — | — |
| Rate of residual activity after 10-minute treatment at 55° C. (%) | 86.0 | 81.0 | — | — |
| Rate of residual activity after 10-minute treatment at 60° C. (%) | 46.0 | — | 73.0 | 76.0 |

As a result, the rate of residual activity of the 1,5-AG dehydrogenase Ver. 10.0 exhibiting high thermostability was 97%, 91%, 86% and 46% after 10-minute treatment at 45° C., 50° C., 55° C. and 60° C., respectively. The rates of residual activities of the 1,5-AG dehydrogenases Ver. 1.0 to Ver. 11.0 were 8% or more after 10-minute treatment at 45° C. The rates of residual activities of the 1,5-AG dehydrogenases Ver. 2.0 to Ver. 11.0 were 30% or more after 10-minute treatment at 45° C. The rates of residual activities of the 1,5-AG dehydrogenases Ver. 11.1 and Ver. 12.0 exhibiting the highest thermostability were 73% and 76%, respectively, after 10-minute treatment at 60° C.

Moreover, the amino acid residue substitution site in each thermostable 1,5-AG dehydrogenase and the introduced variation sites in the gene encoding each thermostable 1,5-AG dehydrogenase are as shown in FIGS. 3-1, 3-2 and 3-3. Of them, the amino acid sequence of the 1,5-AG dehydrogenase Ver. 2.0 and the nucleotide sequence encoding it are shown in SEQ ID NO: 22; the amino acid sequence of the 1,5-AG dehydrogenase Ver. 7.1 and the nucleotide sequence encoding it are shown in SEQ ID NO: 23; and the amino acid sequence of the 1,5-AG dehydrogenase Ver. 12.0 and the nucleotide sequence encoding it are shown in SEQ ID NOs: 1 and 2, respectively.

The nucleotide sequence of the gene encoding each thermostable 1,5-AG dehydrogenase was analyzed using a fully automatic DNA sequencer ABI PRISM 3100-Avant (manufactured by Applied Biosystems, Inc.).

As a result, it could be confirmed that the amino acid sequence of the 1,5-AG dehydrogenase Ver. 12.0 represented by SEQ ID NO: 1 has a position 4 converted to an alanine residue, a position 14 converted to a threonine residue, a position 37 converted to an arginine residue, a position 50 converted to a glutamine residue, a position 67 converted to a glycine residue, a position 80 converted to a tyrosine residue, a position 93 converted to a methionine residue, a position 156 converted to a proline residue, a position 164 converted to a methionine residue, a position 202 converted to an aspartic acid residue, a position 235 converted to an alanine residue, a position 348 converted to a tyrosine residue, a position 362 converted to an arginine residue, and a position 473 converted to an alanine residue, compared with the 1,5-AG dehydrogenase Ver. 0 of the parent strain.

EXAMPLE 4

Production of Thermostable 1,5-AG Dehydrogenase (Ver. 2.0)
(A) Culture of Recombinant (pTrc-PS-AGDH-ver2.0/JM109)
Seed Culture:

50 mL of an LB medium was added to a 500-mL Erlenmeyer flask and sterilized in an autoclave. Ampicillin sodium (final concentration: 100 μg/mL) was further added thereto immediately before use. To this LB medium, a genetic recombinant pTrc-PS-AGDH-ver2.0/JM109 was inoculated and shake-cultured (120 rpm) at 25° C. After 16 hours into the culture, the culture solution was used as an inoculum for main culture.

Main Culture:

100 mL of an LB medium was added to a 500-mL Erlenmeyer flask and sterilized in an autoclave. Ampicillin sodium (final concentration: 100 μg/mL) was further added thereto immediately before use. Such media were prepared corresponding to 40 flasks. To each medium, 1 mL of the prepared inoculum was transplanted and shake-cultured (120 rpm) at 25° C. for 3 hours. To the culture solution, 0.1 mM filter-sterilized IPTG was added, and the mixture was further shake-cultured at 25° C. for 21 hours. After the completion of the culture, microbial cells were collected using a centrifuge.

(B) Purification of Recombinant 1,5-AG Dehydrogenase

From the microbial cells thus obtained by culture, the thermostable 1,5-AG dehydrogenase (Ver. 2.0) was separated and purified through each purification step described below. The results are shown in Table 2.

The 1,5-AG dehydrogenase activity was determined based on the method described in EXAMPLE 1, and its specific activity was determined according to the equation described in EXAMPLE 3.

TABLE 2

| Purification step | Total activity (U) | Specific activity (U/mg) | Yield (%) | Purity (fold) |
|---|---|---|---|---|
| CFE | 9871 | 4.39 | 100 | 1.00 |
| Ammonium sulfate precipitation | 5082 | 13.8 | 51.5 | 3.15 |
| Weak anion-exchange chromatography (DEAE FF) | 2893 | 13.5 | 29.3 | 3.08 |
| Desalting and concentration | 3222 | 13.5 | 32.6 | 3.10 |

Preparation of Cell-Free Extracts (CFE):

To the microbial cells collected in the main culture of the paragraph (A), 360 mL of a 50 mM sodium phosphate buffer, pH 7.5 was added to prepare a bacterial cell suspension. Triton X-100 (final concentration: 0.25%) was further added thereto. This bacterial cell suspension was divided to 4 portions, each of which was disrupted at an output of 180 W for 30 minutes using an ultrasonicator (manufactured by KUBOTA Corp., INSONATOR 201M). These bacterial cell disruption solutions were combined and centrifuged (11000× g, 4° C., 30 minutes), and 360 mL of CFE was collected.

Ammonium Sulfate Fractionation:

To the CFE, 51.84 g of ammonium sulfate was added in small portions under ice cooling while dissolved, resulting in a saturated concentration of 25%. After the dissolution of ammonium sulfate, the mixture was further stirred for 30 minutes. This lysate was centrifuged (11000×g, 4° C., 30 minutes), and 380 mL of the supernatant was collected. Next, to this supernatant, 35.34 g of ammonium sulfate was added in small portions under ice cooling while dissolved, resulting in a saturated concentration of 40%. After the dissolution of ammonium sulfate, the mixture was further stirred for 30 minutes and then left standing overnight at 4° C.

Dialysis:

From the ammonium sulfate-treated solution, ammonium sulfate precipitates were collected by centrifugation (11000× g, 4° C., 30 minutes). The ammonium sulfate precipitates were dissolved in 10 mL of a 50 mM sodium phosphate buffer, pH 7.5. The solution was placed in a dialysis tube and dialyzed against a dialysis buffer (20 mM Tris-HCl, pH 7.5, 20% glycerin).

Centrifugation:

Insoluble matter was formed in the dialysis tube and therefore was removed by centrifugation (27000×g, 4° C., 15 minutes) to obtain 14 mL of a supernatant.

Weak Anion-Exchange Chromatography (DEAE Sepharose Fast Flow):

The supernatant was charged onto 320 mL of a weak anion-exchange resin DEAE Sepharose Fast Flow (manufactured by GE Healthcare Biosciences) (column size: 2.6 cm×60 cm high) equilibrated with an equilibration buffer (20 mM Tris-HCl, pH 7.5, 20% glycerin). After the completion of the charge, the column was washed with a washing buffer (20 mM Tris-HCl, pH 7.5, 20% glycerin) in an amount 3 times the bed volume of the resin. Then, the protein of interest was eluted on a gradient using an elution buffer (1:20 mM Tris-HCl, pH 7.5, 20% glycerin, 2:20 mM Tris-HCl, pH 7.5, 20% glycerin, 1 M NaCl) in an amount 5 times the bed volume of the resin to obtain 396 mL of an active fraction.

Desalting and Concentration:

The active fraction was concentrated into 17.5 mL using an ultrafiltration apparatus model 8200 (manufactured by Amicon, ultrafiltration membrane molecular weight cutoff: 100,000) to obtain 3,222 U of a thermostable 1,5-AG dehydrogenase (Ver. 2.0).

REFERENCE EXAMPLE 1

Substrate Specificity of Parent Strain-Derived 1,5-AG Dehydrogenase

The variation-free 1,5-AG dehydrogenase (Ver. 0) was used in the same purification method as in EXAMPLE 4. A precipitate fraction of 40%-saturated ammonium sulfate was collected by centrifugation and dissolved in a 50 mM sodium phosphate buffer, pH 7.5. The enzymatic activity of this enzyme solution was determined for several kinds of sugars or sugar alcohols and shown in Table 3 as a relative activity with the activity for 1,5-AG as 100%. The enzymatic activity was determined by the method described in the paragraph (J) of EXAMPLE 1.

TABLE 3

| Substrate | Relative activity (%) |
|---|---|
| 1,5-AG | 100 |
| Glucose | 3 |
| L-sorbose | 54 |
| Maltose | 0.2 |
| Galactose | 0 |
| Xylose | 0 |
| Xylitol | 0 |

EXAMPLE 5

Assay of 1,5-AG by Colorimetry

A first reagent with composition shown in Table 4 and a second reagent containing the thermostable 1,5-AG dehydrogenase (Ver. 7.1) of the present invention were used to conduct assay in clinical samples using a fully automatic biochemical test analyzer HITACHI 7020 routinely used in clinical tests. Specifically, 180 µL of the first reagent is added to 4.5 µL of samples and reacted at 37° C. for 5 minutes. Next, 60 µL of the second reagent is added thereto and reacted at 37° C. for 5 minutes. Absorbance was measured by a two-point end method from 17 points to 35 points with a dominant wavelength of 450 nm and a subwavelength of 570 nm as photometric wavelengths.

The clinical samples used in this EXAMPLE were serum collected from healthy individuals and diabetes mellitus patients.

TABLE 4

| First reagent | | Second reagent | |
|---|---|---|---|
| Tris buffer | 25 mM | Phosphate buffer | 25 mM |
| WST-1 | 0.83 mM | 1,5-AG dehydrogenase | 0.2 U/mL |
| Glucokinase | 4 U/mL | Sodium azide | 0.1% |
| Adenosine-5'-triphosphate | 10.4 mM | | |
| Magnesium chloride | 7.38 mM | | |
| Sodium azide | 0.1% | | |
| (pH 8.2) | | (pH 7.0) | |

Preparation of Calibration Curve

Standard solutions of 0 or 50 µg/mL 1,5-AG were prepared using saline. The standard solutions were subjected to assay by the 1,5-AG assay method to prepare a calibration curve. The amount of increase in absorbance in the calibration curve is shown in Table 5.

TABLE 5

| 1,5-AG (µg/mL) | 0 | 50 |
|---|---|---|
| Increase in absorbance | 0.0025 | 0.146 |

Assay in Samples 50 serum samples derived from healthy individuals and diabetes mellitus patients were subjected to assay according to the 1,5-AG assay method (method of the present invention), and their 1,5-AG assay values were determined by calculation from the calibration curve.

Figure 4:
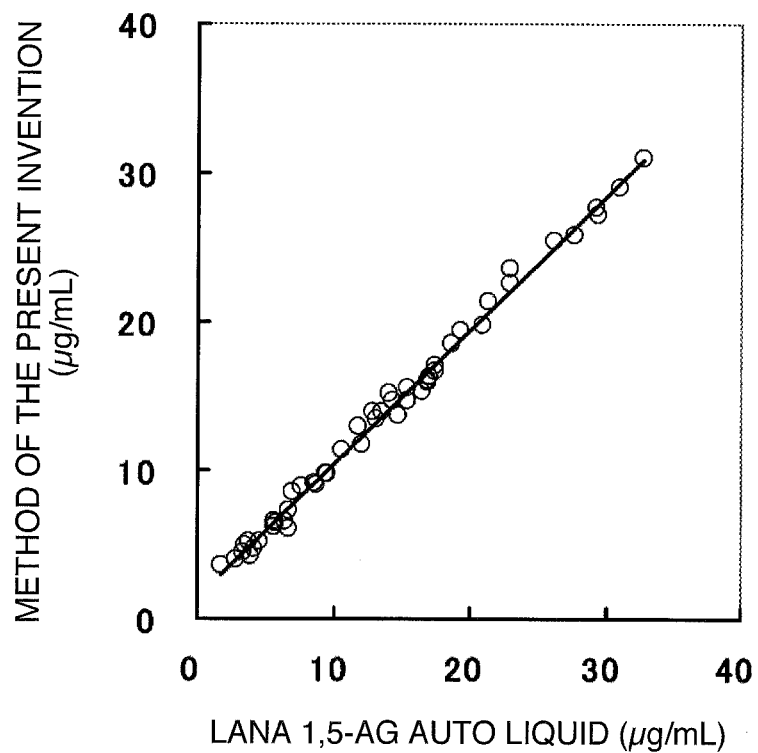
FIG. 4 is a diagram plotting 1,5-AG assay values obtained using an assay method of the present invention based on absorptiometry (using the thermostable 1,5-AG dehydrogenase Ver. 7.1) and 1,5-AG assay values obtained using a commercially available 1,5-AG assay reagent "LANA 1,5-AG Auto Liquid" for 50 serum samples.

On the other hand, results obtained by assay in the same samples as above using "LANA 1,5-AG Auto Liquid" manufactured by NIPPON KAYAKU Co., Ltd, were compared with the results obtained by the method of the present invention, and the comparison results are shown in FIG. 4.

As shown in the graph of FIG. 4, favorable correlation with a correlation equation: Y=0.9017X+1.3794 and a correlation coefficient: 0.9936 was confirmed between the assay values obtained by these methods.

EXAMPLE 6

Assay of 1,5-AG by Colorimetry

A first reagent with composition shown in Table 5 and a second reagent containing the thermostable 1,5-AG dehydrogenase (Ver. 10.0) of the present invention were used to conduct assay in clinical samples using a fully automatic biochemical test analyzer HITACHI 7020 routinely used in clinical tests. Specifically, 180 µL of the first reagent is added to 4.5 µL of samples and reacted at 37° C. for 5 minutes. Next, 60 µL of the second reagent is added thereto and reacted at 37° C. for 5 minutes. Absorbance was measured by a two-point end method from 17 points to 35 points with a dominant wavelength of 450 nm and a subwavelength of 570 nm as photometric wavelengths.

The clinical samples used in this EXAMPLE were serum collected from healthy individuals and diabetes mellitus patients.

TABLE 6

| First reagent | | Second reagent | |
|---|---|---|---|
| Tris buffer | 25 mM | Phosphate buffer | 25 mM |
| WST-1 | 0.83 mM | 1,5-AG dehydrogenase | 0.2 U/mL |
| Glucokinase | 4 U/mL | Bovine albumin | 1% |
| Adenosine-5'-triphosphate | 10.4 mM | Sodium azide | 0.1% |
| Magnesium chloride | 7.38 mM | | |
| Sodium azide | 0.1% | | |
| (pH 8.2) | | (pH 7.0) | |

Preparation of Calibration Curve

Standard solutions of 0 or 50 µg/mL 1,5-AG were prepared using saline. The standard solutions were subjected to assay by the 1,5-AG assay method to prepare a calibration curve. The amount of increase in absorbance in the calibration curve is shown in Table 7.

TABLE 7

| 1,5-AG (µg/mL) | 0 | 50 |
|---|---|---|
| Increase in absorbance | 0.0082 | 0.1413 |

Assay in Samples 50 serum samples derived from healthy individuals and diabetes mellitus patients were subjected to assay according to the 1,5-AG assay method (method of the present invention), and their 1,5-AG assay values were determined by calculation from the calibration curve.

Figure 5:
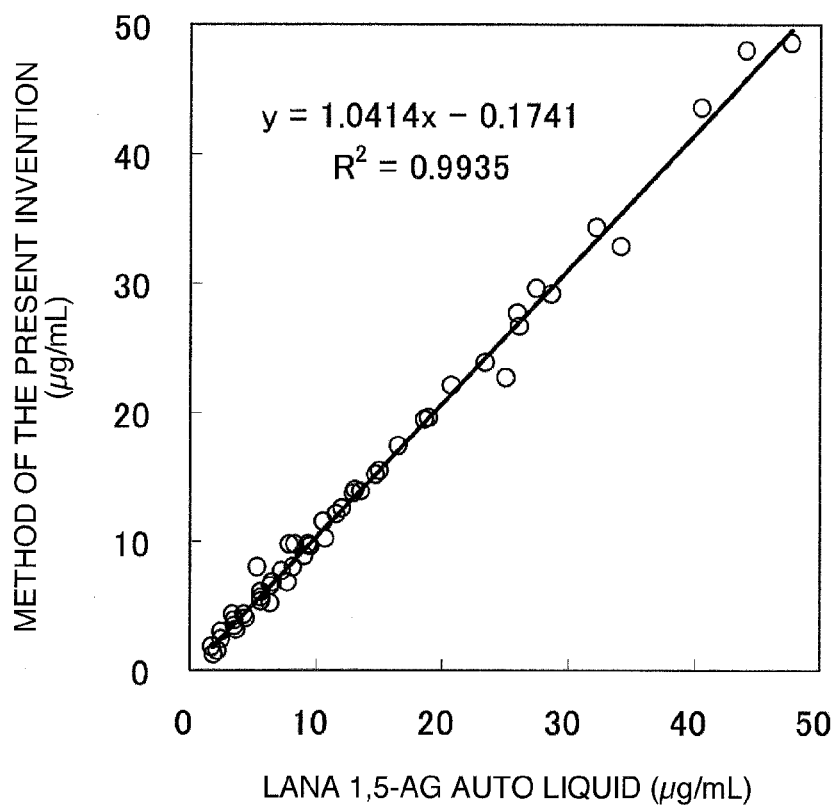
FIG. 5 is a diagram plotting 1,5-AG assay values obtained using the assay method of the present invention based on absorptiometry (using the thermostable 1,5-AG dehydrogenase Ver. 10.0) and 1,5-AG assay values obtained using "LANA 1,5-AG Auto Liquid" for 50 serum samples.

On the other hand, results obtained by assay in the same samples as above using "LANA 1,5-AG Auto Liquid" manufactured by NIPPON KAYAKU Co., Ltd. were compared with the results obtained by the method of the present invention, and the comparison results are shown in FIG. 5.

As shown in the graph of FIG. 5, favorable correlation with a correlation equation: Y=1.0414X−0.1741 and a correlation coefficient: 0.9935 was confirmed between the assay values obtained by these methods.

EXAMPLE 7

Assay of 1,5-AG by Colorimetry of Albumin

A first reagent shown in Table 7 and a second reagent containing the 1,5-AG dehydrogenase Ver. 7.1 with albumin were used to conduct continuous and repetitive assay using, as samples, standard solutions of 0 or 50 µg/mL 1,5-AG prepared using saline and using a fully automatic biochemical test analyzer HITACHI 7020 routinely used in clinical tests.

In the assay method, 180 µL of the first reagent is added to 4.5 µL of samples and reacted at 37° C. for 5 minutes. Next, 60 µL of the second reagent is added thereto and reacted at 37° C. for 5 minutes. Absorbance was measured by a two-point end method from 17 points to 35 points with a dominant wavelength of 450 nm and a subwavelength of 570 nm as photometric wavelengths. The assay in the standard 1,5-AG solutions was performed by repetitively and continuously conducting the assay four times for the standard solutions of 0 or 50 µg/mL 1,5-AG.

TABLE 8

| First reagent | | Second reagent | |
|---|---|---|---|
| Tris buffer | 25 mM | Phosphate buffer | 25 mM |
| WST-1 | 0.83 mM | 1,5-AG dehydrogenase | 0.2 U/mL |
| Sodium azide | 0.1% | Bovine albumin | 1% |
| | | Sodium azide | 0.1% |
| (pH 8.2) | | (pH 7.0) | |

COMPARATIVE EXAMPLE 1

Continuous assay was conducted in the same way as in EXAMPLE 7 using a first reagent of Table 8 and a second reagent containing the variation-free 1,5-AG dehydrogenase.

TABLE 9

| First reagent | | Second reagent | |
|---|---|---|---|
| Tris buffer | 25 mM | Phosphate buffer | 25 mM |
| WST-1 | 0.83 mM | 1,5-AG dehydrogenase | 0.2 U/mL |
| Sodium azide | 0.1% | Sodium azide | 0.1% |
| (pH 8.2) | | (pH 7.0) | |

Results of repetitively measuring the absorbance of the standard 1,5-AG solutions using the assay reagents of EXAMPLE 7 and COMPARATIVE EXAMPLE 1 are shown in Table 9.

TABLE 10

| | | The number of use of the same cell | | | |
|---|---|---|---|---|---|
| | Standard 1,5-AG solution | 1st run | 2nd run | 3rd run | 4th run |
| EXAMPLE 7 | Absorbance at 0 µg/mL | 0.009 | 0.009 | 0.008 | 0.009 |
| | Absorbance at 50 µg/mL | 0.149 | 0.148 | 0.149 | 0.149 |
| COMPARATIVE EXAMPLE 1 | Absorbance at 0 µg/mL | 0.002 | 0.002 | 0.002 | 0.002 |
| | Absorbance at 50 µg/mL | 0.136 | 0.147 | 0.153 | 0.155 |

As seen from Table 9, the absorbance of the standard solution of 50 µg/mL 1,5-AG of COMPARATIVE EXAMPLE 1 was increased with increase in the number of use of the same cell in repetitive assay, whereas increase in the absorbance of the standard solution of 50 µg/mL 1,5-AG of EXAMPLE 7 was not observed, regardless of the number of use of the same cell. As is evident from this result, the coexistence of albumin in 1,5-AG assay achieves stable repetitive assay of 1,5-AG.

EXAMPLE 8

Assay of 1,5-AG by Electrochemical Measurement Method
[1] Method for Determining 1,5-AG Dehydrogenase Activity Using 1,5-AG as Substrate In an electrochemical measurement method, the activity value of the 1,5-AG dehydrogenase was determined by the following method using 1,5-AG as a substrate:
Composition of Reaction Solution:

| (1) 0.1M N-Tris(hydroxymethyl)methyl-3-aminopropanesulfonic acid buffer pH 8.0 | 0.14 mL |
|---|---|
| (2) 20 mM WST-1 (dissolved in (1)) | 0.12 mL |
| (3) distilled water | 0.13 mL |
| (4) 1M aqueous 1,5-AG solution | 0.20 mL |
| (5) enzyme solution | 0.01 mL |
| (6) enzyme dilution (same as (1)) | 0.01 mL |

Procedures:

The temperatures of a constant-temperature water bath and a cell holder of a spectrophotometer are set to 37° C.

1) A quartz cell (optical path length: 1 cm, optical path width: 2 mm) is placed in the cell holder of 37° C. and kept at this temperature for 5 minutes.

2) The reagents (1) to (4) are placed in a 4-mL glass test tube, mixed, and kept at 37° C. in the constant-temperature water bath for 5 minutes.

3) The enzyme solution (5) is added to the test tube of 2) and mixed, and the mixture is immediately transferred to the quartz cell of 1), which is then loaded to a cell holder. The amount of change in absorbance at OD 438 nm is measured.

4) The amount of change in absorbance for 1 minute after 30 seconds into the measurement at OD 438 nm is defined as ΔOD/min.

5) That for a solution supplemented with the enzyme dilution (6) instead of the enzyme solution (5) is defined as a blank value ΔOD blank/min.
Calculation Equation:

Activity (U/mL)={(ΔOD/min-ΔOD blank/min)×0.6 (mL)×dilution ratio}/{1.0 (cm)×37 (cm$^2$/µmol)*×0.01 (mL)}.

The amount of the enzyme reducing 1 µmol WST-1 for 1 minute under the above-described conditions is defined as 1 U.

*37 (cm$^2$/µmol): mmol molecular extinction coefficient (cm$^2$/µmol) of WST-1.
[2] Glucose Conversion Reagent Each component was added to a 10.0 mM HEPES buffer such that the composition after adjustment to pH 7.7 using a 1 N aqueous sodium hydroxide solution was 17.6 mM MgCl$_2$, 17.6 mM KCl, 175.7 mM phosphoenolpyruvic acid (PEP), 17.6 mM ATP, 123 U/mL pyruvate kinase (PK), 75 U/mL glucokinase, 200 U/mL ascorbic acid oxidase, 100 mM sodium chloride, 0.1% NaN$_3$, 0.1 mM EDTA and 0.06% BSA (bovine serum albumin) to prepare a glucose conversion reagent.
[3] Sensor Chip On a polyethylene terephthalate substrate, a working electrode and a lead portion and a counter electrode and a lead portion were screen-printed at a thickness of 10 µm using a carbon ink (manufactured by Asahi Chemical Research Laboratory Co., Ltd., product name: Carbon Paste TU15ST), and a reference electrode and a lead portion were screen-printed at a thickness of 10 μm using a silver-silver chloride ink (manufactured by Acheson Japan Ltd, product name: Electrodag PE-409). After quenching at 150° C. for 40 minutes, a resist ink (manufactured by Asahi Chemical Research Laboratory Co., Ltd., product name: CR18G-KF) was screen-printed at a thickness of 20 μm in a portion except for the electrode portions and a portion connected with a measurement apparatus and quenched at 130° C. for 15 minutes to prepare electrodes shown in FIG. 6.

Next, each component was dissolved in purified water such that the composition was 120 μM thionine acetate (manufactured by Sigma-Aldrich Inc.) and 2.16 U/mL 1,5-AG dehydrogenase (Ver. 2.0) of the present invention to prepare an electrode reagent solution. 2 μL of this reagent solution was applied onto the working electrode in the electrodes and dried at 50° C. for 5 minutes to prepare a sensor chip.

[4] Preparation of Calibration Curve

To prepare a 1,5-AG calibration curve, a 1,5-AG preparation having a known concentration was added to sheep serum (manufactured by NIPPON BIOTEST LABO.) to prepare 6 samples (1,5-AG concentration of each sample was 0.6, 2.8, 5.0, 10.0, 24.7 or 50.2 μg/mL), 10 μL each of which was then mixed with 5 μL of the glucose conversion reagent in an Eppendorf tube and left for 5 minutes. Then, 10 μL of the reaction solution was added dropwise to a sample addition position 1 (FIG. 6) of the sensor chip prepared in the preceding paragraph. −0.1 V for 10 seconds and subsequently 0 V for 110 seconds were applied thereto with respect to the reference electrode (silver-silver chloride). The amount of coulomb for 100 seconds from the initiation of 0 V application was measured using an electrochemical detector (8-CH multipotentiostat MODEL PS-08 equipped with GPIB RS232C; TOHO TECHNICAL RESEARCH CO., LTD.). A calibration curve was prepared from the amount of coulomb and the 1,5-AG concentrations. The calibration curve that exhibited favorable linearity is shown in FIG. 7.

[5] Procedures of Assaying 1,5-AG in Total Blood Sample

10 μL each of 23 total blood samples including samples-derived from diabetes mellitus patients was mixed with 5 μL of the glucose conversion reagent in an Eppendorf tube and left for 5 minutes. Then, 10 μL of the reaction solution was added dropwise to a sample addition position 1 (FIG. 6) of the sensor chip prepared in the above paragraph. −0.1 V for 10 seconds and subsequently 0 V for 110 seconds were applied thereto with respect to the reference electrode (silver-silver chloride). The amount of coulomb for 100 seconds from the initiation of 0 V application was measured using an electrochemical detector. The amount of 1,5-AG in the total blood of these 23 samples was determined by comparison with the calibration curve. The results are indicated in a mean from four measurements.

The amount of 1,5-AG in each plasma obtained by centrifugation procedures from the total blood samples used in assay in this EXAMPLE was measured using "LANA 1,5-AG Auto Liquid" manufactured by NIPPON KAYAKU Co., Ltd.

Figure 8:
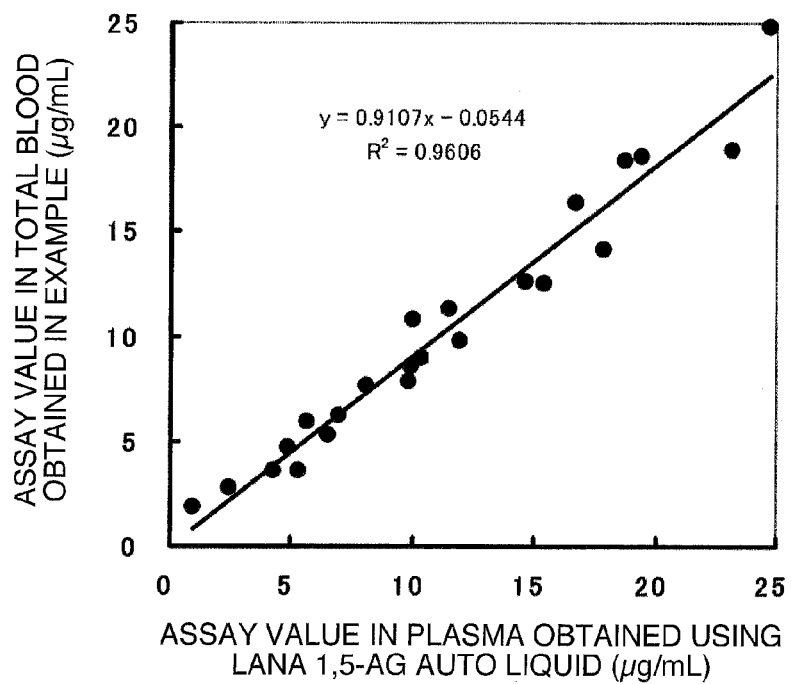
FIG. 8 is a diagram plotting 1,5-AG assay values in 23 total blood samples obtained using the electrochemical measurement method of the present invention and 1,5-AG assay values in serum samples obtained using "LANA 1,5-AG Auto Liquid"

A graph plotting the assay values obtained in this EXAMPLE and the assay values obtained using LANA 1,5-AG Auto Liquid is shown in FIG. 8. Favorable correlation with a correlation coefficient of 0.9606 was obtained between them. This result indicates that the present invention achieves assay of 1,5-AG in the total blood of diabetes mellitus patients.

EXAMPLE 9

Comparison of Stability of Each Thermostable 1,5-AG Dehydrogenase by Electrochemical Measurement Method

[1] Glucose Conversion Reagent

A glucose conversion reagent was prepared in the same way as in EXAMPLE 8.

[2] Sensor Chip

Figure 6:
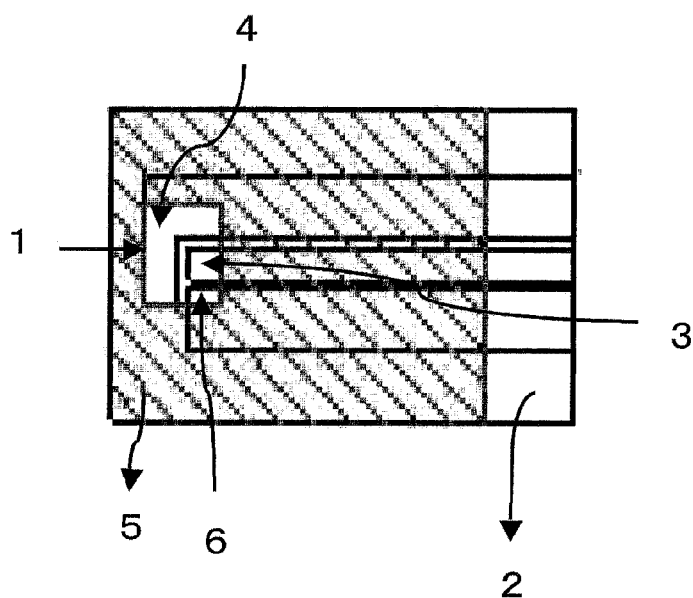
FIG. 6 is a diagram schematically showing electrodes used in the electrochemical measurement of 1,5-AG of the present invention.
Figure 7:
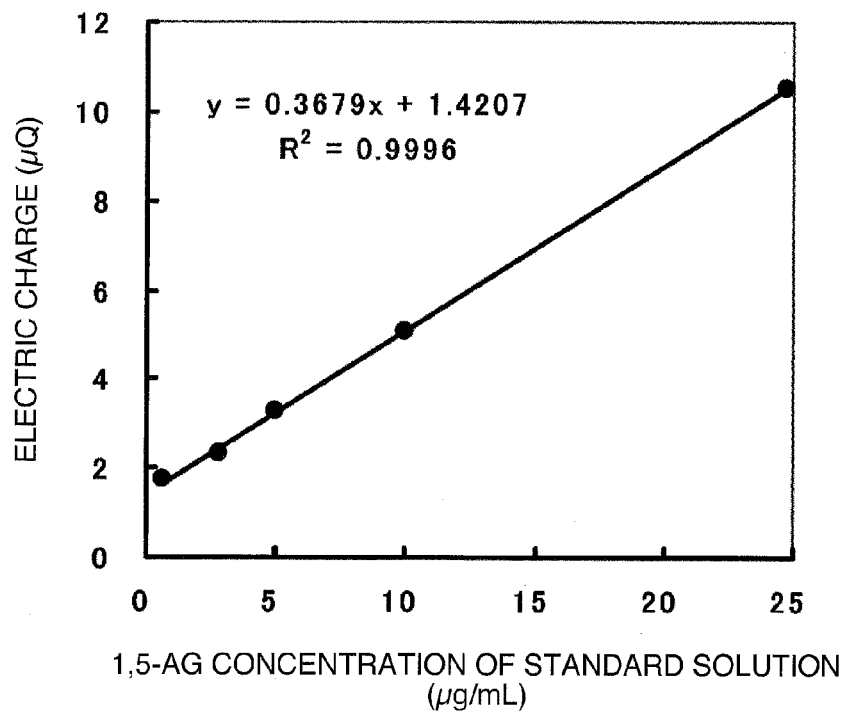
FIG. 7 is a diagram showing a calibration curve of electric charge vs. the amount of 1,5-AG in the electrochemical measurement of 1,5-AG.

Electrodes shown in FIG. 6 were prepared in the same way as in EXAMPLE 8.

Next, each component was dissolved in purified water such that the composition was 120 μM thionine acetate (manufactured by Sigma-Aldrich Inc.), 3.26 U/mL 1,5-AG dehydrogenase (Vet 2.0) of the present invention, and 50 mM piperazine-1,4-bis(2-ethanesulfonic acid) (PIPES) (pH 7.0) to prepare an electrode reagent solution. 2 μL of this reagent solution was applied onto the working electrode in the electrodes and dried at 50° C. for 5 minutes to prepare a sensor chip. Hereinafter, this sensor chip is also referred to as a Ver. 2.0 chip.

Likewise, each component was dissolved in purified water such that the composition was 120 μM thionine acetate (manufactured by Sigma-Aldrich Inc.), 3.26 U/mL 1,5-AG dehydrogenase (Ver. 3.2) of the present invention, and 50 mM piperazine-1,4-bis(2-ethanesulfonic acid) (PIPES) (pH 7.0) to prepare an electrode reagent solution. 2 μL of this reagent solution was applied onto the working electrode in the electrodes and dried at 50° C. for 5 minutes to prepare a sensor chip. Hereinafter, this sensor chip is also referred to as a Ver. 3.2 chip.

Moreover, likewise, each component was dissolved in purified water such that the composition was 120 μM thionine acetate (manufactured by Sigma-Aldrich Inc.), 3.26 U/mL 1,5-AG dehydrogenase (Ver. 10.0) of the present invention, and 50 mM piperazine-1,4-bis(2-ethanesulfonic acid) (PIPES) (pH 7.0) to prepare an electrode reagent solution. 2 μL of this reagent solution was applied onto the working electrode in the electrodes and dried at 50° C. for 5 minutes to prepare a sensor chip. Hereinafter, this sensor chip is also referred to as a Ver. 10.0 chip.

[3] Storage Stability Test

Each sensor chip thus prepared was placed in a sealed container together with a silica gel in the shade and stored for 53 days in an incubator of 55° C.

[4] Evaluation by Electrochemical Measurement

Electrochemical measurement was performed using the chips thus stored for the predetermined period. The degree of degeneration was evaluated, and the stability of each thermostable 1,5-AG dehydrogenase was evaluated and compared with one another.

A 1,5-AG preparation was added to a 0.38% aqueous sodium citrate solution to prepare a standard 1,5-AG solution (1,5-AG concentration of the standard solution was 50.4 μg/mL) 10 μL of this standard solution was mixed with 5 μL of the glucose conversion reagent in an Eppendorf tube and left for 5 minutes. Then, 10 μL of the reaction solution was added dropwise to a sample addition position 1 (FIG. 6) of the sensor chip prepared in the above paragraph. −0.1 V for 10 seconds and subsequently 0 V for 110 seconds were applied thereto with respect to the reference electrode (silver-silver chloride). The amount of coulomb for 100 seconds from the initiation of 0 V application was measured using an electrochemical detector (8-CH multipotentiostat MODEL PS-08 equipped with GPIB RS232C; TOHO TECHNICAL RESEARCH CO., LTD.). Each relative rate of change (%) was determined from the amount of coulomb after a lapse of 7 days, 14 days, 31 days, 35 days, 46 days and 53 days with the amount of coulomb after 3-day storage as 100%.

Figure 9:
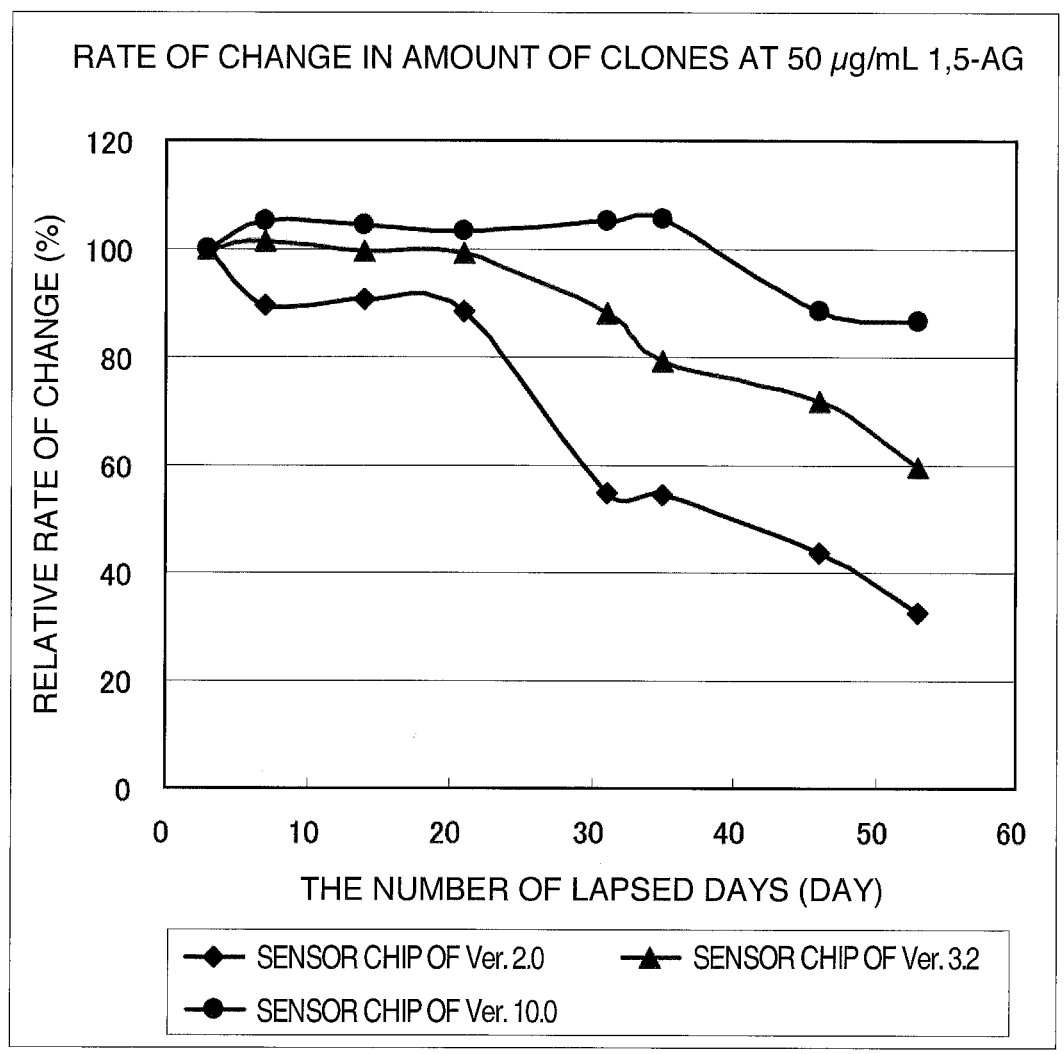
FIG. 9 is a diagram showing storage stability, wherein in the ordinate electrochemical responses were relatively plotted, which were obtained by storing, at 55° C. for 53 days, sensor chips prepared using the thermostable 1,5-AG dehydrogenases Ver. 2.0, 3.2 or 10.0.

The results of this EXAMPLE is shown in FIG. 9. It was demonstrated that stability as a sensor chip was significantly improved according to improvement in the thermostability of the 1,5-AG dehydrogenase.

INDUSTRIAL APPLICABILITY

A thermostable 1,5-AG dehydrogenase of the present invention is an enzyme that specifically acts on 1,5-AG, exhibits excellent storage stability because of having thermostability, and is exceedingly useful in 1,5-AG quantification reagents or convenient and practical 1,5-AG assay using an enzyme sensor introduced commercially. Moreover, a method for assaying 1,5-AG using the thermostable 1,5-AG dehydrogenase is a highly sensitive and stable method and can be put in practical use. Furthermore, a kit for assaying 1,5-AG containing the thermostable 1,5-AG dehydrogenase has enhanced storage stability and can be used in clinical practice.

| DESCRIPTION OF REFERENCE NUMERALS | |
|---|---|
| 1 | sample addition position |
| 2 | support |
| 3 | working electrode |
| 4 | counter electrode |
| 5 | resist |
| 6 | reference electrode (silver-silver chloride ink) |

The invention claimed is:

1. An isolated thermostable 1,5-anhydroglucitol dehydrogenase protein comprising (A) or (B):
   wherein (A) is the amino acid sequence of SEQ ID NO: 4 having at least one variation selected from variations consisting of an amino acid residue at position 4 changed from a glycine residue to an alanine residue, an amino acid residue at position 6 changed from a glutamine residue to a histidine residue, an amino acid residue at position 14 changed from a serine residue to a threonine residue, an amino acid residue at position 37 changed from an alanine residue to a threonine residue or an arginine residue, an amino acid residue at position 50 changed from a proline residue to a glutamine residue, an amino acid residue at position 67 changed from a glutamic acid residue to a glycine residue, an amino acid residue at position 80 changed from an asparagine residue to a tyrosine residue, an amino acid residue at position 93 changed from a valine residue to a methionine residue, an amino acid residue at position 156 changed from an arginine residue to a proline residue, an amino acid residue at position 164 changed from a leucine residue to a methionine residue, an amino acid residue at position 202 changed from an asparagine residue to an aspartic acid residue, an amino acid residue at position 235 changed from a threonine residue to an alanine residue, an amino acid residue at position 348 changed from an asparagine residue to a tyrosine residue, an amino acid residue at position 362 changed from a glycine residue to an arginine residue, and an amino acid residue at position 473 changed from a valine residue to an alanine residue; and
   wherein (B) is the amino acid sequence of (A) in which 1 to 10 amino acid residues are deleted, substituted, or added in addition to the variations found in the amino acid sequence of (A), wherein
   the isolated thermostable 1,5-anhydroglucitol dehydrogenase protein has 1,5-anhydroglucitol dehydrogenase activity and maintains 8% or more of its 1,5-anhydroglucitol dehydrogenase activity after heating at 45° C. for 10 minutes.

2. An isolated thermostable 1,5-anhydroglucitol dehydrogenase protein selected from the following proteins:
   I) a protein comprising the amino acid sequence of SEQ ID NO: 1 which has all the variations described in (A) of claim 1 except for the variation at position 6, wherein the variation of the amino acid residue at position 37 is to an arginine residue;
   II) a protein comprising the amino acid sequence of SEQ ID NO: 1 having an arginine residue in place of a praline residue at position 156;
   III) a protein comprising the amino acid sequence of SEQ ID NO: 1 having an arginine residue in place of a proline residue at position 156 and a valine residue in place of an alanine residue at position 473;
   IV) a protein comprising the amino acid sequence of SEQ ID NO: 1 having a glutamic acid residue in place of a glycine residue at position 67, an arginine residue in place of a proline residue at position 156, and a valine residue in place of an alanine residue at position 473;
   V) a protein comprising the amino acid sequence of SEQ ID NO: 1 having a glutamic acid residue in place of a glycine residue at position 67, an asparagine residue in place of a tyrosine residue at position 80, an arginine residue in place of a proline residue at position 156, and a valine residue in place of an alanine residue at position 473;
   VI) a protein comprising the amino acid sequence of SEQ ID NO: 1 having a glutamic acid residue in place of a glycine residue at position 67, an asparagine residue in place of a tyrosine residue at position 80, an asparagine residue in place of an aspartic acid residue at position 202, and a valine residue in place of an alanine residue at position 473;
   VII) a protein comprising the amino acid sequence of SEQ ID NO: 1 having a glutamic acid residue in place of a glycine residue at position 67, an asparagine residue in place of a tyrosine residue at position 80, an arginine residue in place of a proline residue at position 156, and an asparagine residue in place of an aspartic acid residue at position 202;
   VIII) a protein comprising the amino acid sequence of SEQ ID NO: 1 having a glutamic acid residue in place of a glycine residue at position 67, an arginine residue in place of a proline residue at position 156, an asparagine residue in place of an aspartic acid residue at position 202, and a valine residue in place of an alanine residue at position 473;
   IX) a protein comprising the amino acid sequence of SEQ ID NO: 1 having a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473;

X) a protein comprising the amino acid sequence of SEQ ID NO: 1 having a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, and a valine residue in place of an alanine residue at position 473;

XI) a protein comprising the amino acid sequence of SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a praline residue at position 156, an asparagine residue in place of an aspartic acid residue at position 202, and a valine residue in place of an alanine residue at position 473;

XII) a protein comprising the amino acid sequence of SEQ ID NO: 1 having a threonine residue in place of an arginine residue at position 37, a glutamic acid residue in place of a glycine residue at position 67, an asparagine residue in place of a tyrosine residue at position 80, an arginine residue in place of a proline residue at position 156, an asparaginc residue in place of an aspartic acid residue at position 202, a threonine residue in place of an alanine residue at position 235, an asparagine residue in place of a tyrosine residue at position 348, and a valine residue in place of an alanine residue at position 473;

XIII) a protein comprising the amino acid sequence of SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, an asparagine residue in place of a tyrosine residue at position 348, and a valine residue in place of an alanine residue at position 473;

XIV) a protein comprising the amino acid sequence of SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, and a valine residue in place of an alanine residue at position 473;

XV) a protein comprising the amino acid sequence of SEQ ID NO: 1 having a glycine residue in place of an alanine residue at position 4, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

XVI) a protein comprising the amino acid sequence of SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

XVII) a protein comprising the amino acid sequence of SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, an asparagine residue in place of an aspartic acid residue at position 202, a threonine residue in place of an alanine residue at position 235, an asparagine residue in place of a tyrosine residue at position 348, and a valine residue in place of an alanine residue at position 473;

XVIII) a protein comprising the amino acid sequence of SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473;

XIX) a protein comprising the amino acid sequence of SEQ ID NO: 1 having a glycine residue in place of an alanine residue at position 4, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, and a valine residue in place of an alanine residue at position 473;

XX) a protein comprising the amino acid sequence of SEQ ID NO: 1 having a glycine residue in place of an alanine residue at position 4, a histidine residue in place of a glutamine residue at position 6, a serine residue in place of a threonine residue at position 14, a threonine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473; and XXI) a protein comprising the amino acid sequence of SEQ ID NO: 1 having a glycine residue in place of an alanine residue at position 4, a serine residue in place of a threonine residue at position 14, an alanine residue in place of an arginine residue at position 37, a glutamic acid residue in place of a glycine residue at position 67, an asparagine residue in place of a tyrosine residue at position 80, a valine residue in place of a methionine residue at position 93, an arginine residue in place of a proline residue at position 156, a leucine residue in place of a methionine residue at position 164, an asparagine residue in place of an aspartic acid residue at position 202, a threonine residue in place of an alanine residue at position 235, an asparagine residue in place of a tyrosine residue at position 348, a glycine residue in place of an arginine residue at position 362, and a valine residue in place of an alanine residue at position 473, wherein the isolated thermostable 1,5-anhydroglucitol dehydrogenase protein has 1,5-anhydroglucitol dehydrogenase activity and maintains 8% or more of its 1,5-anhydroglucitol dehydrogenase activity after heating at 45° C. for 10 minutes.

3. An isolated gene comprising a DNA sequence (a) or (b):
wherein (a) is the DNA sequence encoding the protein according to claims 1; and
a wherein (b) is the DNA sequence which hybridizes to the sequence of (a) in 0.1 to 2 SSC solution at 65° C.

4. A recombinant vector containing the DNA sequence according to claim 3.

5. An isolated transformant host cell comprising the recombinant vector according to claim 4.

6. The isolated transformant host cell according to claim 5, wherein a host for the transformant is *E. coli*.

7. A method for producing a thermostable 1,5-anhydroglucitol dehydrogenase, comprising culturing the transformant cell according to claim 5 and collecting the protein according to claim 1 from the cultures.

8. A method for assaying 1,5-anhydroglucitol using the isolated thermostable 1,5-anhydroglucitol dehydrogenase protein according to claim 1.

9. The method for assaying 1,5-anhydroglucitol according to claim 8, wherein the assay of 1,5-anhydroglucitol is performed in the presence of albumin.

10. The method for assaying 1,5-anhydroglucitol according to claim 8, wherein the assay method is an electrochemical measurement method using a phenothiazine compound as a redox mediator and a silver-silver chloride electrode as a reference electrode or a counter electrode.

11. A kit for assaying 1,5-anhydroglucitol, comprising the protein according to claim 1.

\* \* \* \* \*

SEQUENCE LISTING

```
<160> NUMBER OF SEQ ID NOS: 23

<210> SEQ ID NO 1
<211> LENGTH: 496
<212> TYPE: PRT
<213> ORGANISM: Artificial Sequence
<220> FEATURE:
<223> OTHER INFORMATION: Protein expressed by mutated
      1,5-anhydroglucitol dehydrogenase gene

<400> SEQUENCE: 1

Met Glu Phe Ala Gly Gln Pro Asp Ile Val Ile Ile Gly Thr Gly Ile
1               5                   10                  15

Gly Gly Ala Ser Ile Ala Ala Gly Leu Ser Ala Ser Gly Ala Asp Ile
            20                  25                  30

Leu Ile Leu Glu Arg Gly Glu Ser Leu Pro Asp Arg Pro Glu Asn Arg
        35                  40                  45

Asp Gln His Ala Ile Phe Gln Arg Gly Phe Phe Arg Pro Lys Glu Phe
    50                  55                  60

Trp Tyr Gly Thr Asp Gly Thr Pro Phe Asn Pro Gly Asn Tyr Tyr Tyr
65                  70                  75                  80

Val Gly Gly Asn Ser Lys Phe Tyr Gly Ala Val Leu Met Arg Tyr Arg
                85                  90                  95

Arg Glu Asp Phe Glu Glu Leu Ala His Leu Glu Gly Val Ser Pro Ala
            100                 105                 110

Trp Pro Phe Ala Tyr Asp Glu Leu Glu Pro Trp Tyr Cys Lys Ala Glu
        115                 120                 125

Glu Leu Phe Gln Val Arg Gly Glu Leu Gly Asp Asp Pro Thr Glu Pro
    130                 135                 140

Tyr His Ser Lys Pro Tyr Ser Tyr Pro Ala Ile Pro Asp Glu Ser Pro
145                 150                 155                 160

Ile Ala Asp Met Arg Ala Arg Leu Lys Lys Ala Gly Leu His Pro Ala
                165                 170                 175

Ser Leu Pro Leu Gly Val Asp Ile Glu Arg Trp Leu Ala Lys Ala Lys
            180                 185                 190

Thr Pro Trp Asp Ala His Pro Asn Ser Asp Asp Gly Lys Met Asp Ala
        195                 200                 205

Glu Thr Cys Pro Leu Ala Leu Ala Leu Lys His Pro Asn Val Gly Leu
    210                 215                 220

Glu Thr Ser Ala Arg Val Thr Lys Leu Glu Ala Gly Pro Asp Gly Lys
225                 230                 235                 240
```

```
Thr Ile Val Ala Val His Tyr Val Lys Asn Gly Glu Ala Leu Val Leu
            245                 250                 255

Arg Pro Lys Leu Val Ile Leu Ser Ala Gly Ala Val Gln Ser Ala Ala
            260                 265                 270

Leu Leu Leu Arg Ser Gly Leu Ala Asn Arg Ser Asp Gln Val Gly Arg
        275                 280                 285

Asn Phe Met Asn His Asn Ala Ser Ala Val Ile Gly Phe Asp Pro Arg
    290                 295                 300

Tyr Arg Asn Asp Ser Val Tyr Gln Lys Thr Phe Gly Phe Asn Asp Tyr
305                 310                 315                 320

Tyr Leu Ser Asp Gly Ala Gly Pro Pro Leu Gly Asn Val Gln Leu
            325                 330                 335

Leu Gly Arg Val Ser Gly Ala Ile Leu Lys Ser Tyr Met Arg Gln Val
            340                 345                 350

Pro Glu Trp Phe Leu Asn Arg Ile Ala Arg His Thr Ile Asp Phe Tyr
            355                 360                 365

Ala Met Ser Glu Asp Leu Pro Ser Pro Glu Ser Arg Val Ser Val Asp
            370                 375                 380

Gly Asp Arg Ile Ile Leu His Trp Val Arg Ser Asn Trp Lys Ala His
385                 390                 395                 400

Leu Met Leu Val Asp Lys Leu Lys Ser Ala Leu Arg Ala Ala Gly Phe
            405                 410                 415

Pro Val Val Leu Ser Arg Ala Phe Asp Arg Arg Thr Pro Ser His Gln
            420                 425                 430

Cys Gly Thr Val Arg Ile Gly Asp Asn Pro Ala Thr Ala Pro Leu Asp
            435                 440                 445

Pro Tyr Cys Arg Ala Tyr Asp His Pro Asn Leu Tyr Val Val Asp Ala
450                 455                 460

Ser Phe Leu Pro Thr Ser Ala Ala Ala Asn Pro Ala Leu Thr Ile Ala
465                 470                 475                 480

Ala Gln Ala Leu Arg Val Ala Asp His Leu Asn Arg Glu Val Leu Ala
            485                 490                 495

<210> SEQ ID NO 2
<211> LENGTH: 1488
<212> TYPE: DNA
<213> ORGANISM: Artificial Sequence
<220> FEATURE:
<223> OTHER INFORMATION: Mutated 1,5-anhydroglucitol dehydrogenase gene

<400> SEQUENCE: 2
atggaattcg caggacagcc ggatatcgtc attatcggaa cgggtatcgg cggcgcgagc      60
atagccgccg gcctgagcgc atcaggtgcg gacattctca ttctggagag gggcgagagc     120
ctgccggaca gaccggaaaa ccgcgatcaa cacgccattt ccagcgtgg tttctttcgc      180 ccgaaagagt tctggtatgg acgatggc acgccgttta atcccggaaa ttattactat      240
gtcggcggca attccaaatt ctatggcgca gtgctgatgc gctatcggcg cgaggatttt     300
gaggagcttg cgcatcttga aggcgtgtct ccggcgtggc ccttcgccta tgatgagctt     360
gagccctggt attgcaaggc ggaagagctt tttcaggtgc gcggtgaatt gggcgatgac     420
ccgaccgagc cgtatcattc taagcccttat tcctatccgg ctatccctga tgaaagcccg     480
attgccgata tgcgtgcacg gctgaagaag gcagggctgc atccggcttc cttgccattg     540
ggtgttgata ttgagcgctg gctggcgaag gccaaaacgc cgtgggacgc gcatcccaac     600
agcgatgacg gcaagatgga tgcggagact tgtccgttag cacttgcgct caaacatcca     660
```

-continued

```
aatgtcgggc ttgaaacctc cgcgcgggta acgaagctgg aagccgggcc cgatggtaaa       720
accattgtgg cagttcatta tgtgaagaat ggcgaagcgc tggtcctgcg tcctaagctc       780
gttattctgt cagcgggagc cgtgcagtcg gcagcgcttt tgctgcgttc gggactggcg       840
aaccgttccg atcaggtcgg tcgcaatttc atgaaccaca atgccagtgc ggttatcggg       900
tttgatccgc gctatcgcaa tgacagcgtc taccagaaga cctttggctt taacgattat       960
tatctcagcg atggggctgg cgggccgccg cttggcaatg tgcaattgct ggggcgggtg      1020
tcgggcgcga tcctgaaatc ctatatgcgt caggtgccgg aatggttttt aaaccgcatt      1080
gccaggcata cgattgattt ttacgcgatg agcgaagatc tgccatcgcc ggaaagtcgc      1140
gtgagcgtgg atggtgatcg catcattctg cattgggtgc gttccaactg gaaggcgcat      1200
ctgatgctgg tcgacaagct caaatccgca ttgcgagcgg cggggtttcc ggtggttctg      1260
tcgcgggcct tcgacaggcg aacaccatcg catcaatgcg gcacggtgcg tatcggcgat      1320
aatccagcaa cagcgccgct tgatccttat tgccgtgctt atgaccaccc caatctctat      1380
gtggtcgatg catcgttcct accgacttcg gctgcggcca atcctgcgct gacgattgcg      1440
gcacaggcgt tgcgcgtggc ggaccatttg aaccgggagg tgctggca                   1488
```

<210> SEQ ID NO 3
<211> LENGTH: 1488
<212> TYPE: DNA
<213> ORGANISM: Pseudomonas sp. NK-85001

<400> SEQUENCE: 3

```
atggaattcg gaggacagcc ggatatcgtc attatcggat cgggtatcgg cggcgcgagc        60
atagccgccg gcctgagcgc atcaggtgcg gacattctta ttctggaggc aggcgagagc       120
ctgccggaca gaccggaaaa ccgcgatcca cacgccattt ccagcgtggg tttctttcgc       180
ccgaaagagt tctggtatga gacggatggc acgccgttta atcccggaaa ttattacaat       240
gtcggcggca attccaaatt ctatggcgca gtgctggtgc gctatcggcg cgaggatttt       300
gaggagcttg cgcatcttga aggcgtgtct ccggcgtggc ccttcgccta tgatgagctt       360
gagccctggt attgcaaggc ggaagagctt tttcaggtgc gcggtgaatt gggcgatgac       420
ccgaccgagc cgtatcattc taagccctat tcctatccgg ctatccgtga tgaaagcccg       480
attgccgatc tgccgtgcac ggctgaagaa gcagggctgc atccggcttc cttgccattg       540
ggtgttgata ttgagcgctg gctggcgaag gccaaaacgc cgtgggacgc gcatcccaac       600
agcaatgacg gcaagatgga tgcggagact tgtccgttag cacttgcgct caaacatcca       660
aatgtcgggc ttgaaacctc cgcgcgggta acgaagctgg aaaccgggcc cgatggtaaa       720
accattgtgg cagttcatta tgtgaagaat ggcgaagcgc tggtcctgcg tcctaagctc       780
gttattctgt cagcgggagc cgtgcagtcg gcagcgcttt tgctgcgttc gggactggcg       840
aaccgttccg atcaggtcgg tcgcaatttc atgaaccaca atgccagtgc ggttatcggg       900
tttgatccgc gctatcgcaa tgacagcgtc taccagaaga cctttggctt taacgattat       960
tatctcagcg atggggctgg cgggccgccg cttggcaatg tgcaattgct ggggcgggtg      1020
tcgggcgcga tcctgaaatc caatatgcgt caggtgccgg aatggttttt aaaccgcatt      1080
gccgggcata cgattgattt ttacgcgatg agcgaagatc tgccatcgcc ggaaagtcgc      1140
gtgagcgtgg atggtgatcg catcattctg cattgggtgc gttccaactg gaaggcgcat      1200
ctgatgctgg tcgacaagct caaatccgca ttgcgagcgg cggggtttcc ggtggttctg      1260
tcgcgggcct tcgacaggcg aacaccatcg catcaatgcg gcacggtgcg tatcggcgat      1320
```

-continued

```
aatccagcaa cagcgccgct tgatccttat tgccgtgctt atgaccaccc caatctctat    1380
gtggtcgatg catcgttcct accgacttcg gctgcggtca atcctgcgct gacgattgcg    1440
gcacaggcgt tgcgcgtggc ggaccatttg aaccgggagg tgctggca                 1488
```

<210> SEQ ID NO 4
<211> LENGTH: 496
<212> TYPE: PRT
<213> ORGANISM: Pseudomonas sp. NK-85001

<400> SEQUENCE: 4

```
Met Glu Phe Gly Gly Gln Pro Asp Ile Val Ile Gly Ser Gly Ile
1               5                   10                  15

Gly Gly Ala Ser Ile Ala Ala Gly Leu Ser Ala Ser Gly Ala Asp Ile
            20                  25                  30

Leu Ile Leu Glu Ala Gly Glu Ser Leu Pro Asp Arg Pro Glu Asn Arg
        35                  40                  45

Asp Pro His Ala Ile Phe Gln Arg Gly Phe Phe Arg Pro Lys Glu Phe
    50                  55                  60

Trp Tyr Glu Thr Asp Gly Thr Pro Phe Asn Pro Gly Asn Tyr Tyr Asn
65                  70                  75                  80

Val Gly Gly Asn Ser Lys Phe Tyr Gly Ala Val Leu Val Arg Tyr Arg
                85                  90                  95

Arg Glu Asp Phe Glu Glu Leu Ala His Leu Gly Val Ser Pro Ala
            100                 105                 110

Trp Pro Phe Ala Tyr Asp Glu Leu Gly Pro Trp Tyr Cys Lys Ala Glu
        115                 120                 125

Glu Leu Phe Gln Val Arg Gly Glu Leu Gly Asp Asp Pro Thr Glu Pro
    130                 135                 140

Tyr His Ser Lys Pro Tyr Ser Tyr Pro Ala Ile Arg Asp Glu Ser Pro
145                 150                 155                 160

Ile Ala Asp Leu Arg Ala Arg Leu Lys Lys Ala Gly Leu His Pro Ala
                165                 170                 175

Ser Leu Pro Leu Gly Val Asp Ile Glu Arg Trp Leu Ala Lys Ala Lys
            180                 185                 190

Thr Pro Trp Asp Ala His Pro Asn Ser Asn Asp Gly Lys Met Asp Ala
        195                 200                 205

Glu Thr Cys Pro Leu Ala Leu Ala Lys His Pro Asn Val Gly Leu
    210                 215                 220

Glu Thr Ser Ala Arg Val Thr Lys Leu Glu Thr Gly Pro Asp Gly Lys
225                 230                 235                 240

Thr Ile Val Ala Val His Tyr Val Lys Asn Gly Glu Ala Leu Val Leu
                245                 250                 255

Arg Pro Lys Leu Val Ile Leu Ser Ala Gly Ala Val Gln Ser Ala Ala
            260                 265                 270

Leu Leu Leu Arg Ser Gly Leu Ala Asn Arg Ser Asp Gln Val Gly Arg
        275                 280                 285

Asn Phe Met Asn His Asn Ala Ser Ala Val Ile Gly Phe Asp Pro Arg
    290                 295                 300

Tyr Arg Asn Asp Ser Val Tyr Gln Lys Thr Phe Gly Phe Asn Asp Tyr
305                 310                 315                 320

Tyr Leu Ser Asp Gly Ala Gly Pro Pro Leu Gly Asn Val Gln Leu
                325                 330                 335

Leu Gly Arg Val Ser Gly Ala Ile Leu Lys Ser Asn Met Arg Gln Val
            340                 345                 350
```

-continued

Pro Glu Trp Phe Leu Asn Arg Ile Ala Gly His Thr Ile Asp Phe Tyr
        355                 360                 365

Ala Met Ser Glu Asp Leu Pro Ser Pro Glu Ser Arg Val Ser Val Asp
    370                 375                 380

Gly Asp Arg Ile Ile Leu His Trp Val Arg Ser Asn Trp Lys Ala His
385                 390                 395                 400

Leu Met Leu Val Asp Lys Leu Lys Ser Ala Leu Arg Ala Ala Gly Phe
            405                 410                 415

Pro Val Val Leu Ser Arg Ala Phe Asp Arg Arg Thr Pro Ser His Gln
        420                 425                 430

Cys Gly Thr Val Arg Ile Gly Asp Asn Pro Ala Thr Ala Pro Leu Asp
            435                 440                 445

Pro Tyr Cys Arg Ala Tyr Asp His Pro Asn Leu Tyr Val Val Asp Ala
        450                 455                 460

Ser Phe Leu Pro Thr Ser Ala Ala Val Asn Pro Ala Leu Thr Ile Ala
465                 470                 475                 480

Ala Gln Ala Leu Arg Val Ala Asp His Leu Asn Arg Glu Val Leu Ala
            485                 490                 495

<210> SEQ ID NO 5
<211> LENGTH: 9
<212> TYPE: PRT
<213> ORGANISM: Pseudomonas sp. NK-85001

<400> SEQUENCE: 5

Pro Asp Ile Val Ile Ile Gly Ser Gly
1               5

<210> SEQ ID NO 6
<211> LENGTH: 10
<212> TYPE: PRT
<213> ORGANISM: Pseudomonas sp. NK-85001

<400> SEQUENCE: 6

Phe Leu Pro Thr Ser Ala Ala Val Asn Pro
1               5                   10

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ccrgayatyg tyatyatcgg                                              20

<210> SEQ ID NO 8
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: n stands for any base
<220> FEATURE:
<221> NAME/KEY: misc_feature
<222> LOCATION: (7)..(7)
<223> OTHER INFORMATION: n stands for any base
<220> FEATURE:
<221> NAME/KEY: misc_feature
<222> LOCATION: (10)..(10)
<223> OTHER INFORMATION: n stands for any base

```
<220> FEATURE:
<221> NAME/KEY: misc_feature
<222> LOCATION: (19)..(19)
<223> OTHER INFORMATION: n stands for any base

<400> SEQUENCE: 8
ggtnagngcn ggattgacng c                                              21

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gaaaatggcg tgtggatcgc gg                                             22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
catcgcatca atgcggcacg gt                                             22

<210> SEQ ID NO 11
<211> LENGTH: 1821
<212> TYPE: DNA
<213> ORGANISM: Pseudomonas sp. NK-85001
<220> FEATURE:
<221> NAME/KEY: CDS
<222> LOCATION: (201)..(1691)

<400> SEQUENCE: 11
gggcgcaagg tgcgcgccgg tacagtctgg atgaacactt tcatggatgg cacaccagaa    60
ctgccttttg gcggttatcg ccagtcgggt ctgggtcgcg agctgggccg tcatgcggtg   120
gaggattata ccgaaaccaa gacgctcaac atgcatatcg tgcgcgcac cggctggtgg   180 atgccgcaag gaaaatagga gtg acg gct ttg gga gga cag ccg gat atc gtc   233
                      Val Thr Ala Leu Gly Gly Gln Pro Asp Ile Val
                       1               5                  10 att atc gga tcg ggt atc ggc ggc gcg agc ata gcc gcc ggc ctg agc     281
Ile Ile Gly Ser Gly Ile Gly Gly Ala Ser Ile Ala Ala Gly Leu Ser
             15                  20                  25 gca tca ggt gcg gac att ctt att ctg gag gca ggc gag agc ctg ccg     329
Ala Ser Gly Ala Asp Ile Leu Ile Leu Glu Ala Gly Glu Ser Leu Pro
         30                  35                  40 gac aga ccg gaa aac cgc gat cca cac gcc att ttc cag cgt ggt ttc     377
Asp Arg Pro Glu Asn Arg Asp Pro His Ala Ile Phe Gln Arg Gly Phe
     45                  50                  55 ttt cgc ccg aaa gag ttc tgg tat gag acg gat ggc acg ccg ttt aat     425
Phe Arg Pro Lys Glu Phe Trp Tyr Glu Thr Asp Gly Thr Pro Phe Asn
60                   65                  70                  75 ccc gga aat tat tac aat gtc ggc ggc aat tcc aaa ttc tat ggc gca     473
Pro Gly Asn Tyr Tyr Asn Val Gly Gly Asn Ser Lys Phe Tyr Gly Ala
                 80                  85                  90 gtg ctg gtg cgc tat cgg cgc gag gat ttt gag gag ctt gcg cat ctt     521
Val Leu Val Arg Tyr Arg Arg Glu Asp Phe Glu Glu Leu Ala His Leu
             95                 100                 105 gaa ggc gtg tct ccg gcg tgg ccc ttc gcc tat gat gag ctt gag ccc     569
Glu Gly Val Ser Pro Ala Trp Pro Phe Ala Tyr Asp Glu Leu Glu Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 110 |     |     |     |     | 115 |     |     |     |     | 120 |     |     |      |
| tgg | tat | tgc | aag | gcg | gaa | gag | ctt | ttt | cag | gtg | cgc | ggt | gaa | ttg | ggc | 617  |
| Trp | Tyr | Cys | Lys | Ala | Glu | Glu | Leu | Phe | Gln | Val | Arg | Gly | Glu | Leu | Gly |      |
|     |     | 125 |     |     |     |     | 130 |     |     |     |     | 135 |     |     |     |      |
| gat | gac | ccg | acc | gag | ccg | tat | cat | tct | aag | ccc | tat | tcc | tat | ccg | gct | 665  |
| Asp | Asp | Pro | Thr | Glu | Pro | Tyr | His | Ser | Lys | Pro | Tyr | Ser | Tyr | Pro | Ala |      |
| 140 |     |     |     |     | 145 |     |     |     |     | 150 |     |     |     |     | 155 |      |
| atc | cgt | gat | gaa | agc | ccg | att | gcc | gat | ctg | cgt | gca | cgg | ctg | aag | aag | 713  |
| Ile | Arg | Asp | Glu | Ser | Pro | Ile | Ala | Asp | Leu | Arg | Ala | Arg | Leu | Lys | Lys |      |
|     |     |     |     | 160 |     |     |     |     | 165 |     |     |     |     | 170 |     |      |
| gca | ggg | ctg | cat | ccg | gct | tcc | ttg | cca | ttg | ggt | gtt | gat | att | gag | cgc | 761  |
| Ala | Gly | Leu | His | Pro | Ala | Ser | Leu | Pro | Leu | Gly | Val | Asp | Ile | Glu | Arg |      |
|     |     |     | 175 |     |     |     |     | 180 |     |     |     |     | 185 |     |     |      |
| tgg | ctg | gcg | aag | gcc | aaa | acg | ccg | tgg | gac | gcg | cat | ccc | aac | agc | aat | 809  |
| Trp | Leu | Ala | Lys | Ala | Lys | Thr | Pro | Trp | Asp | Ala | His | Pro | Asn | Ser | Asn |      |
|     |     | 190 |     |     |     |     | 195 |     |     |     |     | 200 |     |     |     |      |
| gac | ggc | aag | atg | gat | gcg | gag | act | tgt | ccg | tta | gca | ctt | gcg | ctc | aaa | 857  |
| Asp | Gly | Lys | Met | Asp | Ala | Glu | Thr | Cys | Pro | Leu | Ala | Leu | Ala | Leu | Lys |      |
| 205 |     |     |     |     | 210 |     |     |     |     | 215 |     |     |     |     |     |      |
| cat | cca | aat | gtc | ggg | ctt | gaa | acc | tcc | gcg | cgg | gta | acg | aag | ctg | gaa | 905  |
| His | Pro | Asn | Val | Gly | Leu | Glu | Thr | Ser | Ala | Arg | Val | Thr | Lys | Leu | Glu |      |
| 220 |     |     |     |     | 225 |     |     |     |     | 230 |     |     |     |     | 235 |      |
| acc | ggg | ccc | gat | ggt | aaa | acc | att | gtg | gca | gtt | cat | tat | gtg | aag | aat | 953  |
| Thr | Gly | Pro | Asp | Gly | Lys | Thr | Ile | Val | Ala | Val | His | Tyr | Val | Lys | Asn |      |
|     |     |     |     | 240 |     |     |     |     | 245 |     |     |     |     | 250 |     |      |
| ggc | gaa | gcg | ctg | gtc | ctg | cgt | cct | aag | ctc | gtt | att | ctg | tca | gcg | gga | 1001 |
| Gly | Glu | Ala | Leu | Val | Leu | Arg | Pro | Lys | Leu | Val | Ile | Leu | Ser | Ala | Gly |      |
|     |     |     | 255 |     |     |     |     | 260 |     |     |     |     | 265 |     |     |      |
| gcc | gtg | cag | tcg | gca | gcg | ctt | ttg | ctg | cgt | tcg | gga | ctg | gcg | aac | cgt | 1049 |
| Ala | Val | Gln | Ser | Ala | Ala | Leu | Leu | Leu | Arg | Ser | Gly | Leu | Ala | Asn | Arg |      |
|     |     | 270 |     |     |     |     | 275 |     |     |     |     | 280 |     |     |     |      |
| tcc | gat | cag | gtc | ggt | cgc | aat | ttc | atg | aac | cac | aat | gcc | agt | gcg | gtt | 1097 |
| Ser | Asp | Gln | Val | Gly | Arg | Asn | Phe | Met | Asn | His | Asn | Ala | Ser | Ala | Val |      |
| 285 |     |     |     |     | 290 |     |     |     |     | 295 |     |     |     |     |     |      |
| atc | ggg | ttt | gat | ccg | cgc | tat | cgc | aat | gac | agc | gtc | tac | cag | aag | acc | 1145 |
| Ile | Gly | Phe | Asp | Pro | Arg | Tyr | Arg | Asn | Asp | Ser | Val | Tyr | Gln | Lys | Thr |      |
| 300 |     |     |     |     | 305 |     |     |     |     | 310 |     |     |     |     | 315 |      |
| ttt | ggc | ttt | aac | gat | tat | tat | ctc | agc | gat | ggg | gct | ggc | ggg | ccg | ccg | 1193 |
| Phe | Gly | Phe | Asn | Asp | Tyr | Tyr | Leu | Ser | Asp | Gly | Ala | Gly | Gly | Pro | Pro |      |
|     |     |     |     | 320 |     |     |     |     | 325 |     |     |     |     | 330 |     |      |
| ctt | ggc | aat | gtg | caa | ttg | ctg | ggg | cgg | gtg | tcg | ggc | gcg | atc | ctg | aaa | 1241 |
| Leu | Gly | Asn | Val | Gln | Leu | Leu | Gly | Arg | Val | Ser | Gly | Ala | Ile | Leu | Lys |      |
|     |     |     | 335 |     |     |     |     | 340 |     |     |     |     | 345 |     |     |      |
| tcc | aat | atg | cgt | cag | gtg | ccg | gaa | tgg | ttt | tta | aac | cgc | att | gcc | ggg | 1289 |
| Ser | Asn | Met | Arg | Gln | Val | Pro | Glu | Trp | Phe | Leu | Asn | Arg | Ile | Ala | Gly |      |
|     |     | 350 |     |     |     |     | 355 |     |     |     |     | 360 |     |     |     |      |
| cat | acg | att | gat | ttt | tac | gcg | atg | agc | gaa | gat | ctg | cca | tcg | ccg | gaa | 1337 |
| His | Thr | Ile | Asp | Phe | Tyr | Ala | Met | Ser | Glu | Asp | Leu | Pro | Ser | Pro | Glu |      |
| 365 |     |     |     |     | 370 |     |     |     |     | 375 |     |     |     |     |     |      |
| agt | cgc | gtg | agc | gtg | gat | ggt | gat | cgc | atc | att | ctg | cat | tgg | gtg | cgt | 1385 |
| Ser | Arg | Val | Ser | Val | Asp | Gly | Asp | Arg | Ile | Ile | Leu | His | Trp | Val | Arg |      |
| 380 |     |     |     |     | 385 |     |     |     |     | 390 |     |     |     |     | 395 |      |
| tcc | aac | tgg | aag | gcg | cat | ctg | atg | ctg | gtc | gac | aag | ctc | aaa | tcc | gca | 1433 |
| Ser | Asn | Trp | Lys | Ala | His | Leu | Met | Leu | Val | Asp | Lys | Leu | Lys | Ser | Ala |      |
|     |     |     |     | 400 |     |     |     |     | 405 |     |     |     |     | 410 |     |      |
| ttg | cga | gcg | gcg | ggg | ttt | ccg | gtg | gtt | ctg | tcg | cgg | gcc | ttc | gac | agg | 1481 |
| Leu | Arg | Ala | Ala | Gly | Phe | Pro | Val | Val | Leu | Ser | Arg | Ala | Phe | Asp | Arg |      |
|     |     |     | 415 |     |     |     |     | 420 |     |     |     |     | 425 |     |     |      |
| cga | aca | cca | tcg | cat | caa | tgc | ggc | acg | gtg | cgt | atc | ggc | gat | aat | cca | 1529 |
| Arg | Thr | Pro | Ser | His | Gln | Cys | Gly | Thr | Val | Arg | Ile | Gly | Asp | Asn | Pro |      |

```
                    430                 435                 440
gca aca gcg ccg ctt gat cct tat tgc cgt gct tat gac cac ccc aat    1577
Ala Thr Ala Pro Leu Asp Pro Tyr Cys Arg Ala Tyr Asp His Pro Asn
445                 450                 455 ctc tat gtg gtc gat gca tcg ttc cta ccg act tcg gct gcg gtc aat    1625
Leu Tyr Val Val Asp Ala Ser Phe Leu Pro Thr Ser Ala Ala Val Asn
460                 465                 470                 475 cct gcg ctg acg att gcg gca cag gcg ttg cgc gtg gcg gac cat ttg    1673
Pro Ala Leu Thr Ile Ala Ala Gln Ala Leu Arg Val Ala Asp His Leu
                480                 485                 490 aac cgg gag gtg ctg gca tgagccgtca aagacctgtg cactggtga ctggcggg   1729
Asn Arg Glu Val Leu Ala
                495 cggcgtggta tcgggcttgg catagcgcgc gctttagccg ccaaagggtt tgatctggcg   1789 attaccgacc gtgaacgtga tgaggcggtc at                                 1821

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12 ataccatg gaattcggag gacagccgga tatcg                                35

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
atctagagga tcctcatcat gccagcacct cccgg                              35

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gataatgttt tttgcgccga c                                             21

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
tctagatgat cctcatcatg cc                                            22

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
```
gcagtgctga tgcgctatcg g							21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tttcacttct gagttcggca							20

<210> SEQ ID NO 18
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (10)..(10)
<223> OTHER INFORMATION: n stands for any base
<220> FEATURE:
<221> NAME/KEY: misc_feature
<222> LOCATION: (11)..(11)
<223> OTHER INFORMATION: n stands for any base

<400> SEQUENCE: 18
attctggagn nkggcgagag c							21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
aattattact atgtcggcgg c							21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ccggctatcc ctgatgaaag c							21

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
atataccatg gaattcgcag gacagccgga t					31

<210> SEQ ID NO 22
<211> LENGTH: 1491
<212> TYPE: DNA
<213> ORGANISM: Artificial Sequence
<220> FEATURE:
<223> OTHER INFORMATION: Mutated 1,5-anhydroglucitol dehydrogenase gene

<400> SEQUENCE: 22

```
atg gaa ttc gga gga cac ccg gat atc gtc att atc gga tcg ggt atc        48
Met Glu Phe Gly Gly His Pro Asp Ile Val Ile Ile Gly Ser Gly Ile
1               5                   10                  15 ggc ggc gcg agc ata gcc gcc ggc ctg agc gca tca ggt gcg gac att        96
Gly Gly Ala Ser Ile Ala Ala Gly Leu Ser Ala Ser Gly Ala Asp Ile
            20                  25                  30 ctt att ctg gag aca ggc gag agc ctg ccg gac aga ccg gaa aac cgc       144
Leu Ile Leu Glu Thr Gly Glu Ser Leu Pro Asp Arg Pro Glu Asn Arg
        35                  40                  45 gat caa cac gcc att ttc cag cgt ggt ttc ttt cgc ccg aaa gag ttc       192
Asp Gln His Ala Ile Phe Gln Arg Gly Phe Phe Arg Pro Lys Glu Phe
    50                  55                  60 tgg tat gag acg gat ggc acg ccg ttt aat ccc gga aat tat tac aat       240
Trp Tyr Glu Thr Asp Gly Thr Pro Phe Asn Pro Gly Asn Tyr Tyr Asn
65                  70                  75                  80 gtc ggc ggc aat tcc aaa ttc tat ggc gca gtg ctg gtg cgc tat cgg       288
Val Gly Gly Asn Ser Lys Phe Tyr Gly Ala Val Leu Val Arg Tyr Arg
                85                  90                  95 cgc gag gat ttt gag gag ctt gcg cat ctt gaa ggc gtg tct ccg gcg       336
Arg Glu Asp Phe Glu Glu Leu Ala His Leu Glu Gly Val Ser Pro Ala
            100                 105                 110 tgg ccc ttc gcc tat gat gag ctt gag ccc tgg tat tgc aag gcg gaa       384
Trp Pro Phe Ala Tyr Asp Glu Leu Glu Pro Trp Tyr Cys Lys Ala Glu
        115                 120                 125 gag ctt ttt cag gtg cgc ggt gaa ttg ggc gat gac ccg acc gag ccg       432
Glu Leu Phe Gln Val Arg Gly Glu Leu Gly Asp Asp Pro Thr Glu Pro
    130                 135                 140 tat cat tct aag ccc tat tcc tat ccg gct atc cgt gat gaa agc ccg       480
Tyr His Ser Lys Pro Tyr Ser Tyr Pro Ala Ile Arg Asp Glu Ser Pro
145                 150                 155                 160 att gcc gat ctg cgt gca cgg ctg aag aag gca ggg ctg cat ccg gct       528
Ile Ala Asp Leu Arg Ala Arg Leu Lys Lys Ala Gly Leu His Pro Ala
                165                 170                 175 tcc ttg cca ttg ggt gtt gat att gag cgc tgg ctg gcg aag gcc aaa       576
Ser Leu Pro Leu Gly Val Asp Ile Glu Arg Trp Leu Ala Lys Ala Lys
            180                 185                 190 acg ccg tgg gac gcg cat ccc aac agc aat gac ggc aag atg gat gcg       624
Thr Pro Trp Asp Ala His Pro Asn Ser Asn Asp Gly Lys Met Asp Ala
        195                 200                 205 gag act tgt ccg tta gca ctt gcg ctc aaa cat cca aat gtc ggg ctt       672
Glu Thr Cys Pro Leu Ala Leu Ala Leu Lys His Pro Asn Val Gly Leu
    210                 215                 220 gaa acc tcc gcg cgg gta acg aag ctg gaa acc ggg ccc gat ggt aaa       720
Glu Thr Ser Ala Arg Val Thr Lys Leu Glu Thr Gly Pro Asp Gly Lys
225                 230                 235                 240 acc att gtg gca gtt cat tat gtg aag aat ggc gaa gcg ctg gtc ctg       768
Thr Ile Val Ala Val His Tyr Val Lys Asn Gly Glu Ala Leu Val Leu
                245                 250                 255 cgt cct aag ctc gtt att ctg tca gcg gga gcc gtg cag tcg gca gcg       816
Arg Pro Lys Leu Val Ile Leu Ser Ala Gly Ala Val Gln Ser Ala Ala
            260                 265                 270 ctt ttg ctg cgt tcg gga ctg gcg aac cgt tcc gat cag gtc ggt cgc       864
Leu Leu Leu Arg Ser Gly Leu Ala Asn Arg Ser Asp Gln Val Gly Arg
        275                 280                 285 aat ttc atg aac cac aat gcc agt gcg gtt atc ggg ttt gat ccg cgc       912
Asn Phe Met Asn His Asn Ala Ser Ala Val Ile Gly Phe Asp Pro Arg
    290                 295                 300 tat cgc aat gac agc gtc tac cag aag acc ttt ggc ttt aac gat tat       960
Tyr Arg Asn Asp Ser Val Tyr Gln Lys Thr Phe Gly Phe Asn Asp Tyr
305                 310                 315                 320
```

| | | | | | | | | | | | | | | | | |
|---|---|---|---|---|---|---|---|---|---|---|---|---|---|---|---|---|
| tat | ctc | agc | gat | ggg | gct | ggc | ggg | ccg | ccg | ctt | ggc | aat | gtg | caa | ttg | 1008 |
| Tyr | Leu | Ser | Asp | Gly | Ala | Gly | Gly | Pro | Pro | Leu | Gly | Asn | Val | Gln | Leu | |
| | | | 325 | | | | | 330 | | | | | 335 | | | |
| ctg | ggg | cgg | gtg | tcg | ggc | gcg | atc | ctg | aaa | tcc | aat | atg | cgt | cag | gtg | 1056 |
| Leu | Gly | Arg | Val | Ser | Gly | Ala | Ile | Leu | Lys | Ser | Asn | Met | Arg | Gln | Val | |
| | | | 340 | | | | | 345 | | | | | 350 | | | |
| ccg | gaa | tgg | ttt | tta | aac | cgc | att | gcc | ggg | cat | acg | att | gat | ttt | tac | 1104 |
| Pro | Glu | Trp | Phe | Leu | Asn | Arg | Ile | Ala | Gly | His | Thr | Ile | Asp | Phe | Tyr | |
| | | | 355 | | | | | 360 | | | | | 365 | | | |
| gcg | atg | agc | gaa | gat | ctg | cca | tcg | ccg | gaa | agt | cgc | gtg | agc | gtg | gat | 1152 |
| Ala | Met | Ser | Glu | Asp | Leu | Pro | Ser | Pro | Glu | Ser | Arg | Val | Ser | Val | Asp | |
| | | 370 | | | | | 375 | | | | | 380 | | | | |
| ggt | gat | cgc | atc | att | ctg | cat | tgg | gtg | cgt | tcc | aac | tgg | aag | gcg | cat | 1200 |
| Gly | Asp | Arg | Ile | Ile | Leu | His | Trp | Val | Arg | Ser | Asn | Trp | Lys | Ala | His | |
| 385 | | | | | 390 | | | | | 395 | | | | | 400 | |
| ctg | atg | ctg | gtc | gac | aag | ctc | aaa | tcc | gca | ttg | cga | gcg | gcg | ggg | ttt | 1248 |
| Leu | Met | Leu | Val | Asp | Lys | Leu | Lys | Ser | Ala | Leu | Arg | Ala | Ala | Gly | Phe | |
| | | | | 405 | | | | | 410 | | | | | 415 | | |
| ccg | gtg | gtt | ctg | tcg | cgg | gcc | ttc | gac | agg | cga | aca | cca | tcg | cat | caa | 1296 |
| Pro | Val | Val | Leu | Ser | Arg | Ala | Phe | Asp | Arg | Arg | Thr | Pro | Ser | His | Gln | |
| | | | 420 | | | | | 425 | | | | | 430 | | | |
| tgc | ggc | acg | gtg | cgt | atc | ggc | gat | aat | cca | gca | aca | gcg | ccg | ctt | gat | 1344 |
| Cys | Gly | Thr | Val | Arg | Ile | Gly | Asp | Asn | Pro | Ala | Thr | Ala | Pro | Leu | Asp | |
| | | | 435 | | | | | 440 | | | | | 445 | | | |
| cct | tat | tgc | cgt | gct | tat | gac | cac | ccc | aat | ctc | tat | gtg | gtc | gat | gca | 1392 |
| Pro | Tyr | Cys | Arg | Ala | Tyr | Asp | His | Pro | Asn | Leu | Tyr | Val | Val | Asp | Ala | |
| | | 450 | | | | | 455 | | | | | 460 | | | | |
| tcg | ttc | cta | ccg | act | tcg | gct | gcg | gtc | aat | cct | gcg | ctg | acg | att | gcg | 1440 |
| Ser | Phe | Leu | Pro | Thr | Ser | Ala | Ala | Val | Asn | Pro | Ala | Leu | Thr | Ile | Ala | |
| 465 | | | | | 470 | | | | | 475 | | | | | 480 | |
| gca | cag | gcg | ttg | cgc | gtg | gcg | gac | cat | ttg | aac | cgg | gag | gtg | ctg | gca | 1488 |
| Ala | Gln | Ala | Leu | Arg | Val | Ala | Asp | His | Leu | Asn | Arg | Glu | Val | Leu | Ala | |
| | | | | 485 | | | | | 490 | | | | | 495 | | |
| tga | | | | | | | | | | | | | | | | 1491 |

```
<210> SEQ ID NO 23
<211> LENGTH: 1491
<212> TYPE: DNA
<213> ORGANISM: Artificial Sequence
<220> FEATURE:
<223> OTHER INFORMATION: Mutated 1,5-anhydroglucitol dehydrogenase gene

<400> SEQUENCE: 23
```

| | | | | | | | | | | | | | | | | |
|---|---|---|---|---|---|---|---|---|---|---|---|---|---|---|---|---|
| atg | gaa | ttc | gca | gga | cag | ccg | gat | atc | gtc | att | atc | gga | acg | ggt | atc | 48 |
| Met | Glu | Phe | Ala | Gly | Gln | Pro | Asp | Ile | Val | Ile | Ile | Gly | Thr | Gly | Ile | |
| 1 | | | | 5 | | | | | 10 | | | | | 15 | | |
| ggc | ggc | gcg | agc | ata | gcc | gcc | ggc | ctg | agc | gca | tca | ggt | gcg | gac | att | 96 |
| Gly | Gly | Ala | Ser | Ile | Ala | Ala | Gly | Leu | Ser | Ala | Ser | Gly | Ala | Asp | Ile | |
| | | | 20 | | | | | 25 | | | | | 30 | | | |
| ctt | att | ctg | gag | aca | ggc | gag | agc | ctg | ccg | gac | aga | ccg | gaa | aac | cgc | 144 |
| Leu | Ile | Leu | Glu | Thr | Gly | Glu | Ser | Leu | Pro | Asp | Arg | Pro | Glu | Asn | Arg | |
| | | 35 | | | | | 40 | | | | | 45 | | | | |
| gat | caa | cac | gcc | att | ttc | cag | cgt | ggt | ttc | ttt | cgc | ccg | aaa | gag | ttc | 192 |
| Asp | Gln | His | Ala | Ile | Phe | Gln | Arg | Gly | Phe | Phe | Arg | Pro | Lys | Glu | Phe | |
| 50 | | | | | 55 | | | | | 60 | | | | | | |
| tgg | tat | gag | acg | gat | ggc | acg | ccg | ttt | aat | ccc | gga | aat | tat | tac | aat | 240 |
| Trp | Tyr | Glu | Thr | Asp | Gly | Thr | Pro | Phe | Asn | Pro | Gly | Asn | Tyr | Tyr | Asn | |
| 65 | | | | | 70 | | | | | 75 | | | | | 80 | |
| gtc | ggc | ggc | aat | tcc | aaa | ttc | tat | ggc | gca | gtg | ctg | atg | cgc | tat | cgg | 288 |
| Val | Gly | Gly | Asn | Ser | Lys | Phe | Tyr | Gly | Ala | Val | Leu | Met | Arg | Tyr | Arg | |
| | | | | 85 | | | | | 90 | | | | | 95 | | |

| | | |
|---|---|---|
| cgc gag gat ttt gag gag ctt gcg cat ctt gaa ggc gtg tct ccg gcg<br>Arg Glu Asp Phe Glu Glu Leu Ala His Leu Glu Gly Val Ser Pro Ala<br>100                            105                         110 | 336 |
| tgg ccc ttc gcc tat gat gag ctt gag ccc tgg tat tgc aag gcg gaa<br>Trp Pro Phe Ala Tyr Asp Glu Leu Glu Pro Trp Tyr Cys Lys Ala Glu<br>               115                            120                         125 | 384 |
| gag ctt ttt cag gtg cgc ggt gaa ttg ggc gat gac ccg acc gag ccg<br>Glu Leu Phe Gln Val Arg Gly Glu Leu Gly Asp Asp Pro Thr Glu Pro<br>130                           135                         140 | 432 |
| tat cat tct aag ccc tat tcc tat ccg gct atc cgt gat gaa agc ccg<br>Tyr His Ser Lys Pro Tyr Ser Tyr Pro Ala Ile Arg Asp Glu Ser Pro<br>145                         150                         155                         160 | 480 |
| att gcc gat atg cgt gca cgg ctg aag aag gca ggg ctg cat ccg gct<br>Ile Ala Asp Met Arg Ala Arg Leu Lys Lys Ala Gly Leu His Pro Ala<br>                    165                         170                         175 | 528 |
| tcc ttg cca ttg ggt gtt gat att gag cgc tgg ctg gcg aag gcc aaa<br>Ser Leu Pro Leu Gly Val Asp Ile Glu Arg Trp Leu Ala Lys Ala Lys<br>         180                            185                         190 | 576 |
| acg ccg tgg gac gcg cat ccc aac agc aat gac ggc aag atg gat gcg<br>Thr Pro Trp Asp Ala His Pro Asn Ser Asn Asp Gly Lys Met Asp Ala<br>               195                           200                         205 | 624 |
| gag act tgt ccg tta gca ctt gcg ctc aaa cat cca aat gtc ggg ctt<br>Glu Thr Cys Pro Leu Ala Leu Ala Leu Lys His Pro Asn Val Gly Leu<br>210                           215                         220 | 672 |
| gaa acc tcc gcg cgg gta acg aag ctg gaa gcc ggg ccc gat ggt aaa<br>Glu Thr Ser Ala Arg Val Thr Lys Leu Glu Ala Gly Pro Asp Gly Lys<br>225                         230                         235                         240 | 720 |
| acc att gtg gca gtt cat tat gtg aag aat ggc gaa gcg ctg gtc ctg<br>Thr Ile Val Ala Val His Tyr Val Lys Asn Gly Glu Ala Leu Val Leu<br>                        245                         250                         255 | 768 |
| cgt cct aag ctc gtt att ctg tca gcg gga gcc gtg cag tcg gca gcg<br>Arg Pro Lys Leu Val Ile Leu Ser Ala Gly Ala Val Gln Ser Ala Ala<br>                260                          265                         270 | 816 |
| ctt ttg ctg cgt tcg gga ctg gcg aac cgt tcc gat cag gtc ggt cgc<br>Leu Leu Leu Arg Ser Gly Leu Ala Asn Arg Ser Asp Gln Val Gly Arg<br>                   275                         280                         285 | 864 |
| aat ttc atg aac cac aat gcc agt gcg gtt atc ggg ttt gat ccg cgc<br>Asn Phe Met Asn His Asn Ala Ser Ala Val Ile Gly Phe Asp Pro Arg<br>290                           295                         300 | 912 |
| tat cgc aat gac agc gtc tac cag aag acc ttt ggc ttt aac gat tat<br>Tyr Arg Asn Asp Ser Val Tyr Gln Lys Thr Phe Gly Phe Asn Asp Tyr<br>305                         310                         315                         320 | 960 |
| tat ctc agc gat ggg gct ggc ggg ccg ccg ctt ggc aat gtg caa ttg<br>Tyr Leu Ser Asp Gly Ala Gly Gly Pro Pro Leu Gly Asn Val Gln Leu<br>                         325                         330                         335 | 1008 |
| ctg ggg cgg gtg tcg ggc gcg atc ctg aaa tcc tat atg cgt cag gtg<br>Leu Gly Arg Val Ser Gly Ala Ile Leu Lys Ser Tyr Met Arg Gln Val<br>               340                           345                         350 | 1056 |
| ccg gaa tgg ttt tta aac cgc att gcc agg cat acg att gat ttt tac<br>Pro Glu Trp Phe Leu Asn Arg Ile Ala Arg His Thr Ile Asp Phe Tyr<br>                    355                         360                         365 | 1104 |
| gcg atg agc gaa gat ctg cca tcg ccg gaa agt cgc gtg agc gtg gat<br>Ala Met Ser Glu Asp Leu Pro Ser Pro Glu Ser Arg Val Ser Val Asp<br>370                           375                         380 | 1152 |
| ggt gat cgc atc att ctg cat tgg gtg cgt tcc aac tgg aag gcg cat<br>Gly Asp Arg Ile Ile Leu His Trp Val Arg Ser Asn Trp Lys Ala His<br>385                         390                         395                         400 | 1200 |
| ctg atg ctg gtc gac aag ctc aaa tcc gca ttg cga gcg gcg ggg ttt<br>Leu Met Leu Val Asp Lys Leu Lys Ser Ala Leu Arg Ala Ala Gly Phe<br>                    405                         410                         415 | 1248 |

```
ccg gtg gtt ctg tcg cgg gcc ttc gac agg cga aca cca tcg cat caa    1296
Pro Val Val Leu Ser Arg Ala Phe Asp Arg Arg Thr Pro Ser His Gln
            420                 425                 430 tgc ggc acg gtg cgt atc ggc gat aat cca gca aca gcg ccg ctt gat    1344
Cys Gly Thr Val Arg Ile Gly Asp Asn Pro Ala Thr Ala Pro Leu Asp
        435                 440                 445 cct tat tgc cgt gct tat gac cac ccc aat ctc tat gtg gtc gat gca    1392
Pro Tyr Cys Arg Ala Tyr Asp His Pro Asn Leu Tyr Val Val Asp Ala
        450                 455                 460 tcg ttc cta ccg act tcg gct gcg gtc aat cct gcg ctg acg att gcg    1440
Ser Phe Leu Pro Thr Ser Ala Ala Val Asn Pro Ala Leu Thr Ile Ala
465             470                 475                 480 gca cag gcg ttg cgc gtg gcg gac cat ttg aac cgg gag gtg ctg gca    1488
Ala Gln Ala Leu Arg Val Ala Asp His Leu Asn Arg Glu Val Leu Ala
                485                 490                 495 tga                                                                1491
```